United States Patent [19]
Fukushima et al.

[11] Patent Number: 6,120,290
[45] Date of Patent: Sep. 19, 2000

[54] JAW MOVEMENT SIMULATOR, JAW MOVEMENT SIMULATION SYSTEM, AND JAW MOVEMENT SIMULATION METHOD

[75] Inventors: Susumu Fukushima; Masanao Ohashi; Akio Takamura, all of Yokohama, Japan

[73] Assignee: Ono Sokki Co., LTD., Kanagawa, Japan

[21] Appl. No.: 09/173,187

[22] Filed: Oct. 15, 1998

[30] Foreign Application Priority Data

Oct. 22, 1997 [JP] Japan ................................ 9-289996
Oct. 7, 1998 [JP] Japan ................................ 10-285351

[51] Int. Cl.$^7$ .................................................. A61C 19/04
[52] U.S. Cl. ........................ 433/69; 433/54; 433/64; 600/590
[58] Field of Search ........................ 433/54, 56, 64, 433/65, 68, 69; 600/590

[56] References Cited

U.S. PATENT DOCUMENTS

| | | | |
|---|---|---|---|
| 4,354,836 | 10/1982 | Santoni | 433/54 |
| 4,443,191 | 4/1984 | Gutierrez | 433/56 |
| 4,468,198 | 8/1984 | Kataoka et al. | 433/54 |
| 4,836,778 | 6/1989 | Baumrind et al. | 433/69 |
| 4,859,181 | 8/1989 | Neumeyer | 433/69 |
| 5,006,065 | 4/1991 | Waysenson | 433/54 |
| 5,340,309 | 8/1994 | Robertson | 433/69 |

*Primary Examiner*—John J. Wilson
*Attorney, Agent, or Firm*—Oliff & Berridge, PLC

[57] ABSTRACT

In a jaw movement simulator in which an upper jaw model patterned after an upper jaw and a lower jaw model patterned after a lower jaw are mounted, and the lower jaw model is relatively moved with respect to the upper jaw model. A jaw movement simulation system causes the jaw movement simulator to reproduce a movement of the jaw of a test subject in accordance with data obtained through imaging a movement of the jaw of the test subject. The lower jaw model is fixed on an operating plate having 6 degree of freedom by parallel mechanism, and is moved on the basis of data obtained through a movement of the jaw of the human body, thereby simulating a movement of the jaw with great accuracy.

13 Claims, 34 Drawing Sheets

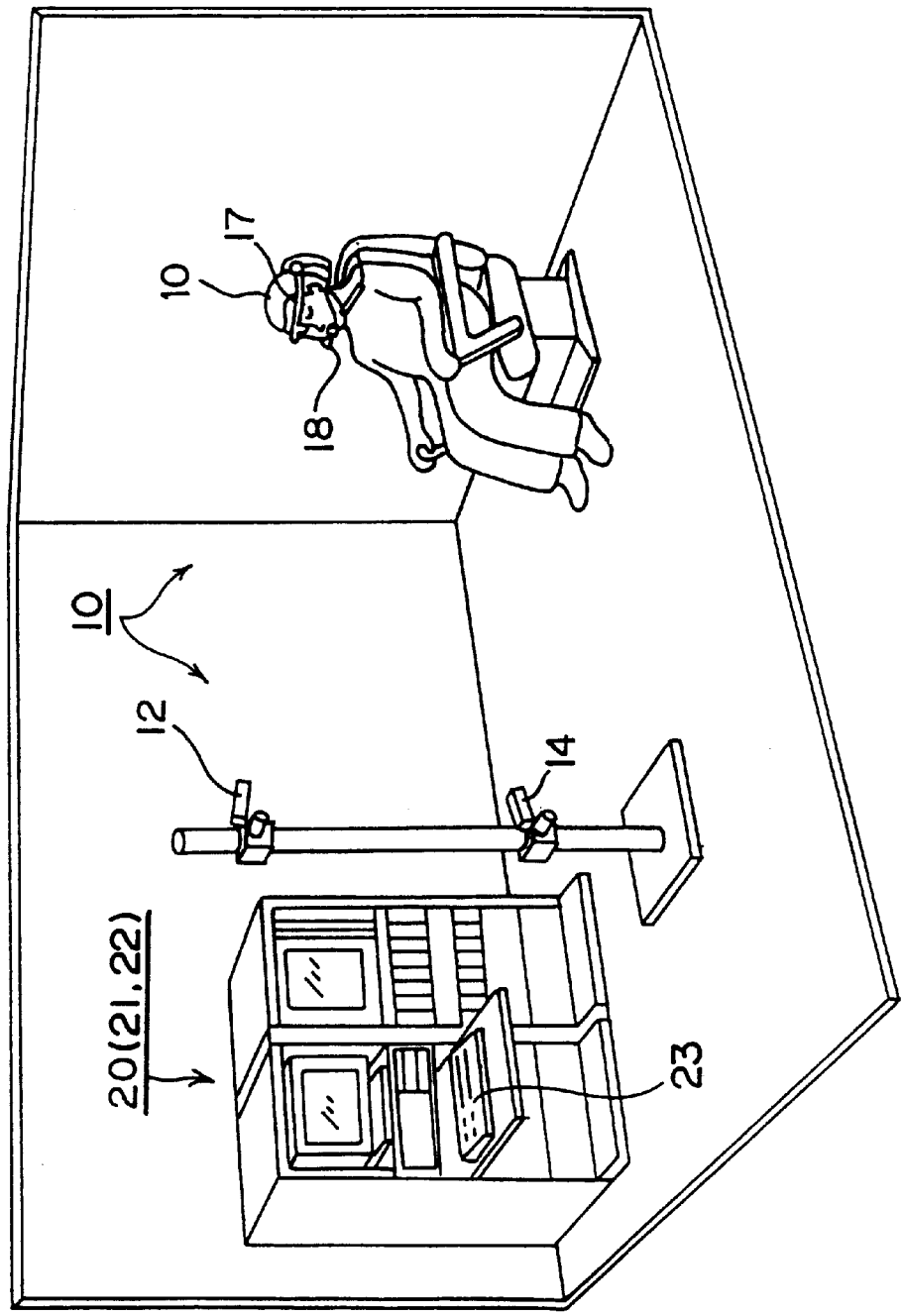

JAW MOVEMENT SIMULATOR, JAW MOVEMENT SIMULATION SYSTEM, AND JAW MOVEMENT SIMULATION METHOD

BACKGROUND OF THE INVENTION

1. Field of the Invention

The present invention relates to a jaw movement simulator in which an upper jaw model patterned after an upper jaw and a lower jaw model patterned after a lower jaw are mounted, and the lower jaw model is relatively moved with respect to the upper jaw model, a jaw movement simulation system for causing the jaw movement simulator to reproduce a movement of the jaw of a test subject in accordance with data obtained through imaging a movement of the jaw of the test subject, and a jaw movement simulation method using the jaw movement simulation system.

2. Description of the Related Art

In the field of dentistry, and more particularly in the field of the dental prosthesis, there is performed such an investigation that models patterned after the upper teeth (upper jaw) and the lower teeth (lower jaw) are formed (such models are referred to as the upper jaw model and the lower jaw model, respectively), and those models are mounted on an articulator device for a simulation of a movement of the jaw, so that the state of occlusion of the upper teeth and the lower teeth is investigated. Thus, there is produced a dental prosthesis (e.g. denture) having a suitable shape according to the state of occlusion.

FIG. 1 is a typical illustration of part of the jaw of the human body.

An upper jaw 2 and a lower jaw 3 are coupled with each other taking a condyle 4 as a joint. The lower jaw 3 is able to perform not only a simple motion of opening and closing one's mouth upward and downward with respect to the upper jaw 2, but also various motions such as moving it back and forth and left and right with respect to the upper jaw 2, and opening one's mouth at a slant. The condyle 4 serves as a complicated joint capable of implementing those various motions. A shape of the condyle and its movement are varied for each person.

Hitherto, as articulators for observing the state of occlusion of the upper jaw model and the lower jaw model mounted thereon, there have been proposed various articulators, for example, a plane line articulator capable of performing only a simple motion of opening and closing for one's mouth; a full adjusted articulator in which a skeleton of the upper jaw 2 and the lower jaw 3 including the condyle 4 is modeled, and a portion corresponding to the condyle of the human body is given with the same freedom as that of the condyle of the human body; and an articulator provided with the mid freedom as compared to that of the condyle of the human body. It is possible to reproduce the more similar motion to that of the human's jaw with larger freedom. However, an adjustment for implementing a high reproduction of movement is a very hard task. Usually, such an adjustment is performed in accordance with intuition of dentists and dental technicians. This often brings about the reproduction of an average movement of jaws of a large number of persons, and thus it is very difficult to exactly reproduce a movement of the jaw of the respective person. Thus, even if such an articulator is used to reproduce a movement of the jaw, there will remain a part which does not match a movement of the jaw of the respective person. Accordingly, on the occasion of making a dental prosthesis, it is obliged to draw on dentist's or dental technician's experience.

It may happen that something wrong in a movement of the jaw or in an occlusion of teeth causes symptoms of stiff shoulders, headache and giddiness to be developed. Recently, it becomes a subject how to grasp that those symptoms are caused by a movement of the jaw, etc. In order to solve this subject, there is a need to provide an apparatus capable of exactly reproducing a movement of the jaw of an individual.

SUMMARY OF THE INVENTION

In view of the foregoing, it is therefore an object of the present invention to provide a jaw movement simulator capable of exactly simulating a jaw movement, a jaw movement simulation system capable of exactly reproducing a movement of the jaw of a test subject, using the jaw movement simulator, and a jaw movement simulation method of exactly reproducing a movement of the jaw.

To accomplish the above-mentioned object, according to the present invention, there is provided a jaw movement simulator in which an upper jaw model patterned after at least part of an upper jaw and a lower jaw model patterned after at least part of a lower jaw are mounted, and the lower jaw model is relatively moved with respect to the upper jaw model, said jaw movement simulator comprising:

(1-1) a substrate;

(1-2) a lower jaw fixing unit on which the lower jaw model is fixed;

(1-3) a lower jaw fixing unit supporting parts for supporting said lower jaw fixing unit in such a manner that a position and a posture of said lower jaw fixing unit in a three-dimensional space are changeable with respect to said substrate;

(1-4) lower jaw driving means for moving said lower jaw fixing unit supporting parts to alter the position and the posture of said lower jaw fixing unit;

(1-5) an upper jaw fixing unit on which the upper jaw model is fixed in a predetermined positional relation with respect to the lower jaw model fixed on said lower jaw fixing unit in a predetermined initial position and a predetermined initial posture; and (1-6) lower jaw control means for controlling said lower jaw driving means in accordance with data representative of relative position and posture of the lower jaw with respect to the upper jaw so that the lower jaw model fixed on said lower jaw fixing unit offers its position and posture according to said data.

In the jaw movement simulator according to the present invention as mentioned above, it is preferable that said lower jaw fixing unit supporting parts has 6 links for supporting said lower jaw fixing unit at mutually different six places, and said lower jaw driving means drives said 6 links independent of one another.

In this case, it is preferable that each of said 6 links is coupled with said lower jaw fixing unit through an associated ball joint, and said lower jaw driving means comprises 6 lower jaw driving apparatuses, corresponding to said 6 links, respectively, each having a motor and a rotating member fixed on a rotating shaft of the motor and connected to an associated link through a ball joint, said rotating member rotating as the rotating shaft rotates.

In the jaw movement simulator according to the present invention as mentioned above, it is preferable that the jaw movement simulator further comprises a lower jaw model fixing position arithmetic means for determining a fixing position of the lower jaw model for said lower jaw fixing unit, and said lower jaw control means controls said lower jaw driving means in accordance with said data and in addition data representative of a fixing position of the lower jaw model, determined by said lower jaw model fixing position arithmetic means.

In this case, it is preferable that the jaw movement simulator further comprises a contact detection probe for detecting that the lower jaw model fixed on said lower jaw fixing unit is in contact with said contact detection probe, and a sensor for detecting a position and an attitude of said lower jaw fixing unit at time when the lower jaw model is in contact with said contact detection probe, and said lower jaw model fixing position arithmetic means determines the fixing position of the lower jaw model for said lower jaw fixing unit in accordance with the position and the posture detected by said sensor.

Alternatively, it is also preferable that the jaw movement simulator further comprises a contact detection probe for detecting that the lower jaw model fixed on said lower jaw fixing unit is in contact with said contact detection probe, and a handler for moving the lower jaw model fixed on said lower jaw fixing unit, and said lower jaw control means controls said lower jaw driving means under operation of said handler, and said lower jaw model fixing position arithmetic means determines the fixing position of the lower jaw model for said lower jaw fixing unit in accordance with the position and the posture of said lower jaw fixing unit at time when the lower jaw model is in contact with said contact detection probe.

In the jaw movement simulator according to the present invention as mentioned above, it is preferable that said lower jaw fixing unit has a first portion supported by said lower jaw fixing unit supporting parts, and a second portion on which the lower jaw model is fixed, said second portion being different from the first portion in position.

Alternatively, it is also preferable that said lower jaw fixing unit has a first member supported by said lower jaw fixing unit supporting parts, a second member on which the lower jaw model is fixed, and a rotating joint for rotatably moving said second member in up and down directions with respect to said first member.

In case of the jaw movement simulator in which the 6 links are provided, the jaw movement simulator further comprises linear actuators each corresponding to an associated one of said 6 links for causing the associated link to expand and contract in a longitudinal direction of the link.

In the jaw movement simulator according to the present invention as mentioned above, it is preferable that the jaw movement simulator further comprises a tension spring adapted for eliminating or reducing backlash of said lower jaw fixing unit.

Further, in the jaw movement simulator according to the present invention as mentioned above, it is preferable that the jaw movement simulator further comprises a plurality of load sensors for measuring at at least three points loads by force due to a first contact of the upper jaw model with the lower jaw model when the upper jaw model fixed on said upper jaw fixing unit and the lower jaw model fixed on said lower jaw fixing unit occlude, and contact point arithmetic means for determining a first contact point at time of occlusion of the upper jaw model and the lower jaw model in accordance with loads measured by said plurality of load sensors.

To accomplish the above-mentioned object, according to the present invention, there is provided a jaw movement simulation system comprising:

(2-1) a jaw movement image pick-up apparatus for imaging a movement of a jaw of a subject, said jaw movement image pick-up apparatus comprising a plurality of cameras for imaging the subject from mutually different directions, a head frame to be mounted on a head of the subject or on a portion moving in one united body together with the head, said head frame having at mutually different at least three points, which are not located on a same straight line, targets visually recognized by the plurality of cameras, said targets being indexes for a coordinate measurement on images through imaging, and a lower jaw frame to be mounted on a lower jaw of the subject, said lower jaw frame having at mutually different at least three points, which are not located on a same straight line, targets visually recognized by the plurality of cameras, said targets being indexes for a coordinate measurement on images through imaging;

(2-2) a jaw movement arithmetic unit for detecting the targets on the images obtained when the subject, on whose head said head frame is fixed and on whose lower jaw said lower jaw frame is fixed, is photographed by said plurality of cameras, to determine data representative of position and posture of the lower jaw of the subject when the head of the subject is referred, in accordance with positions of the targets on the images;

(2-3) a jaw movement reproducing unit in which an upper jaw model patterned after at least part of an upper jaw and a lower jaw model patterned after at least part of a lower jaw are mounted, and the lower jaw model is relatively moved with respect to the upper jaw model, said jaw movement simulator comprising: a substrate; a lower jaw fixing unit on which the lower jaw model is fixed; a lower jaw fixing unit supporting parts for supporting said lower jaw fixing unit in such a manner that a position and a posture of said lower jaw fixing unit in a three-dimensional space are changeable with respect to said substrate; lower jaw driving means for moving said lower jaw fixing unit supporting parts to alter the position and the posture of said lower jaw fixing unit; and an upper jaw fixing unit on which the upper jaw model is fixed in a predetermined positional relation with respect to the lower jaw model fixed on said lower jaw fixing unit in a predetermined initial position and a predetermined initial posture; and (2-4) a jaw movement reproducing control unit for controlling said lower jaw driving means of said jaw movement reproducing unit in accordance with data determined by said jaw movement arithmetic unit so that the lower jaw model fixed on said lower jaw fixing unit of said jaw movement reproducing unit reproduces a movement of the lower jaw of the subject.

To accomplish the above-mentioned object, of jaw movement simulation methods according to the present invention, as a first jaw movement simulation method, there is provided a jaw movement simulation method of reproducing a movement of a jaw of a subject using a jaw movement simulation system comprising:

a jaw movement image pick-up apparatus for imaging a movement of a jaw of a subject, said jaw movement image pick-up apparatus comprising a plurality of cameras for imaging the subject from mutually different directions, a head frame to be mounted on a head of the subject or on a portion moving in one united body together with the head, said head frame having at mutually different at least three points, which are not located on a same straight line, targets visually recognized by the plurality of cameras, said targets being indexes for a coordinate measurement on images through imaging, and a lower jaw frame to be mounted on a lower jaw of the subject, said lower jaw frame having at mutually different at least three points, which are not located on a same straight line, targets visually recognized by the plurality of cameras, said targets being indexes for a coordinate measurement on images through imaging;

a jaw movement arithmetic unit for detecting the targets on the images obtained when the subject, on whose head said head frame is fixed and on whose lower jaw said lower jaw frame is fixed, is photographed by said plurality of cameras, to determine data representative of position and posture of the lower jaw of the subject when the head of the subject is referred, in accordance with positions of the targets on the images;

a jaw movement reproducing unit in which an upper jaw model patterned after at least part of an upper jaw and a lower jaw model patterned after at least part of a lower jaw are mounted, and the lower jaw model is relatively moved with respect to the upper jaw model, said jaw movement simulator comprising: a substrate; a lower jaw fixing unit on which the lower jaw model is fixed; a lower jaw fixing unit supporting parts for supporting said lower jaw fixing unit in such a manner that a position and a posture of said lower jaw fixing unit in a three-dimensional space are changeable with respect to said substrate; lower jaw driving means for moving said lower jaw fixing unit supporting parts to alter the position and the posture of said lower jaw fixing unit; and an upper jaw fixing unit on which the upper jaw model is fixed in a predetermined positional relation with respect to the lower jaw model fixed on said lower jaw fixing unit in a predetermined initial position and a-predetermined initial posture; and a jaw movement reproducing control unit for controlling said lower jaw driving means of said jaw movement reproducing unit in accordance with the first data determined by said jaw movement arithmetic unit so that the lower jaw model fixed on said lower jaw fixing unit of said jaw movement reproducing unit reproduces a movement of the lower jaw of the subject, said jaw movement simulation method is characterized in that in a case where the lower jaw model patterned after at least part of the lower jaw of the subject is mounted on said jaw movement reproducing unit, a reference jig, which has positioning means with respect to said lower jaw fixing unit and at mutually different at least three points, which are not located on a same straight line, targets, said targets being indexes for a coordinate measurement, is fixed on the lower jaw model, the reference jig fixed on the lower jaw model is fixed at a position determined by said positioning means, of said lower jaw fixing unit to fix the lower jaw model on said lower jaw fixing unit, and said lower jaw frame is fixed on the lower jaw model in such a manner that position and posture as to the lower jaw model are substantially the same as those as to the lower jaw of the subject in a case where said lower jaw frame is fixed on the lower jaw of the subject, the lower jaw model is photographed by a plurality of cameras from mutually different directions so that said jaw movement simulation system determines a second data representative of relative position and posture between the lower jaw model and the reference jig fixed on the lower jaw model, as well as the first data, and said jaw movement reproducing control unit controls said lower jaw driving means of said jaw movement reproducing unit in accordance with the first data and the second data, so that the lower jaw model fixed on said lower jaw fixing unit of said jaw movement reproducing unit reproduces a movement of the lower jaw of the subject.

In the first jaw movement simulation method as mentioned above, it is acceptable that the targets of said head frame and the targets of said lower jaw frame are light-emitting elements, and that in a case where the lower jaw model, with which said reference jig is integrated, is fixed on said lower jaw fixing unit and said lower jaw frame is fixed on the lower jaw model, and then the lower jaw model is photographed by a plurality of cameras, a pointer having a plurality of light-emitting elements, in which a positional relationship between the plurality of light-emitting elements and a tip to be in contact with a desired coordinate measurement point is known, is prepared, and said jaw movement simulation system recognizes positions of the light-emitting elements of said lower jaw frame, recognizes positions of the targets of said reference jig by recognition of positions of the light-emitting elements of said pointer by bringing the tip of said pointer into contact with the targets of said reference jig to provide position information of the light-emitting elements of said pointer in form of a parameter, and determines the second data in accordance with positional information as to those recognized positions of the light-emitting elements of said lower jaw frame and positions of the targets of said reference jig.

In the first jaw movement simulation method as mentioned above, it is preferable that the targets of said head frame, the targets of said lower jaw frame, and the targets of said reference jig are light-emitting elements, and that the lower jaw model, with which said reference jig is integrated, is fixed on said lower jaw fixing unit and said lower jaw frame is fixed on the lower jaw model, and then the lower jaw model is photographed by a plurality of cameras, whereby said jaw movement simulation system recognizes positions of the light-emitting elements of said lower jaw frame and positions of the light-emitting elements of said reference jig, and determines the second data in accordance with positional information as to those recognized positions of the light-emitting elements of said lower jaw frame and positions of the light-emitting elements of said reference jig.

To accomplish the above-mentioned object, of jaw movement simulation methods according to the present invention, as a second jaw movement simulation method, there is provided a jaw movement simulation method of reproducing a movement of a jaw of a subject using a jaw movement simulation system comprising:

a jaw movement image pick-up apparatus for imaging a movement of a jaw of a subject, said jaw movement image pick-up apparatus comprising a plurality of cameras for imaging the subject from mutually different directions, a head frame to be mounted on a head of the subject or on a portion moving in one united body together with the head, said head frame having at mutually different at least three points, which are not located on a same straight line, targets visually recognized by the plurality of cameras, said targets being indexes for a coordinate measurement on images through imaging, a lower jaw frame to be fixed on a lower jaw of the subject, said lower jaw frame having at mutually different at least three points, which are not located on a same straight line, targets visually recognized by the plurality of cameras, said targets being indexes for a coordinate measurement on images through imaging, and a pointer having a plurality of targets, in which a positional relationship between the plurality of targets and a tip to be in contact with lower teeth is known;

a jaw movement arithmetic unit for detecting the targets on the images obtained when the subject, on whose head said head frame is fixed and on whose lower jaw said lower jaw frame is fixed, is photographed by said plurality of cameras, to determine a first data representative of position and attitude of the lower jaw of the subject when the head of the subject is referred, in accordance with positions of the targets on the images, and in addition determine contact point position information representative of a contact point of said pointer with respect to the lower jaw in accordance with positions of the targets on the images when the tip of said pointer is in contact with lower teeth;

a jaw movement reproducing unit in which an upper jaw model patterned after at least part of an upper jaw and a lower jaw model patterned after at least part of a lower jaw are mounted, and the lower jaw model is relatively moved with respect to the upper jaw model, said jaw movement simulator comprising: a substrate; a lower jaw fixing unit on which the lower jaw model is fixed; a lower jaw fixing unit supporting parts for supporting said lower jaw fixing unit in such a manner that a position and an posture of said lower jaw fixing unit in a three-dimensional space are changeable with respect to said substrate; lower jaw driving means for moving said lower jaw fixing unit supporting parts to alter the position and the posture of said lower jaw fixing unit; an upper jaw fixing unit on which the upper jaw model is fixed in a predetermined positional relation with respect to the lower jaw model fixed on said lower jaw fixing unit in a predetermined initial position and a predetermined initial posture; and a detachable contact detection probe for detecting a contact of the lower jaw model fixed on the lower jaw fixing unit, in which a positional relationship with said upper jaw fixing unit is defined; and a jaw movement reproducing control unit for controlling said lower jaw driving means of said jaw movement reproducing unit in accordance with the first data determined by said jaw movement arithmetic unit so that the lower jaw model fixed on said lower jaw fixing unit of said jaw movement reproducing unit reproduces a movement of the lower jaw of the subject, said jaw movement simulation method is characterized in that in a case where the lower jaw model patterned after at least part of the lower jaw of the subject is mounted on said jaw movement reproducing unit, said lower jaw fixing unit is moved in such a manner that points on denture of the lower jaw model, which points correspond to contact points of lower teeth of the subject with which said pointer is in contact when a lower jaw movement of the subject is photographed, is in contact with said contact detection probe attached in a state that a positional relationship with said upper jaw fixing unit is defined, so that an operation for causing said jaw movement simulation system to recognize a position and an posture of said lower jaw fixing unit in a contacting state of said contact detection probe is repeated as to at least three denture of the lower jaw model; and said jaw movement simulation system determines a second data representative of a position and an posture of the lower jaw model fixed on said lower jaw fixing unit with respect to said lower jaw fixing unit in accordance with information representative of the position and the posture of the lower jaw model obtained through said operations and said contact point position information; and said jaw movement reproducing control unit controls said lower jaw driving means of said jaw movement reproducing unit in accordance with the first data and the second data, so that the lower jaw model fixed on said lower jaw fixing unit of said jaw movement reproducing unit reproduces a movement of the lower jaw of the subject.

In the second jaw movement simulation method as mentioned above, it is preferable that the targets of said head frame, the targets of said lower jaw frame, and the targets of said pointer are light-emitting elements.

To accomplish the above-mentioned object, of jaw movement simulation methods according to the present invention, as a third jaw movement simulation method, there is provided a jaw movement simulation method of reproducing a movement of a jaw of a subject using a jaw movement simulation system comprising:

a jaw movement image pick-up apparatus for imaging a movement of a jaw of a subject, said jaw movement image pick-up apparatus comprising a plurality of cameras for imaging the subject from mutually different directions, a head frame to be mounted on a head of the subject, said head frame having at mutually different at least three points, which are not located on a same straight line, targets visually recognized by the plurality of cameras, said targets being indexes for a coordinate measurement on images through imaging, a lower jaw frame to be fixed on a front portion of front teeth of a lower jaw of the subject, said lower jaw frame having at mutually different at least three points, which are not located on a same straight line, targets visually recognized by the plurality of cameras, said targets being indexes for a coordinate measurement on images through imaging, and a transfer frame to be fixed on a portion including an upper portion of teeth of the lower jaw of the subject, said transfer frame having at mutually different at least three points, which are not located on a same straight line, targets visually recognized by the plurality of cameras, said targets being indexes for a coordinate measurement on images through imaging;

a jaw movement arithmetic unit for detecting the targets on a first image obtained when the subject, on whose head said head frame is fixed and on whose lower jaw said lower jaw frame is fixed, is photographed by said plurality of cameras, and also detecting the targets on a second image obtained when the subject, on whose lower jaw said lower jaw frame and said transfer frame are fixed, is photographed by said plurality of cameras, to determine a first data representative of position and posture of the lower jaw of the subject when the head of the subject is referred, in accordance with positions of the targets on the first and second images;

a jaw movement reproducing unit in which an upper jaw model patterned after at least part of an upper jaw and a lower jaw model patterned after at least part of a lower jaw are mounted, and the lower jaw model is relatively moved with respect to the upper jaw model, said jaw movement simulator comprising: a substrate; a lower jaw fixing unit on which the lower jaw model is fixed; a lower jaw fixing unit supporting parts for supporting said lower jaw fixing unit in such a manner that a position and an posture of said lower jaw fixing unit in a three-dimensional space are changeable with respect to said substrate; lower jaw driving means for moving said lower jaw fixing unit supporting member to alter the position and the posture of said lower jaw fixing unit; and an upper jaw fixing unit on which the upper jaw model is fixed in a predetermined positional relation with respect to the lower jaw model fixed on said lower jaw fixing unit in a predetermined initial position and a predetermined initial posture; and a jaw movement reproducing control unit for controlling said lower jaw driving means of said jaw movement reproducing unit in accordance with the first data determined by said jaw movement arithmetic unit so that the lower jaw model fixed on said lower jaw fixing unit of said jaw movement reproducing unit reproduces a movement of the lower jaw of the subject, said jaw movement simulation method is characterized in that in a case where the lower jaw model patterned after at least part of the lower jaw of the subject is mounted on said jaw movement reproducing unit, a reference jig, which has positioning means with respect to said lower jaw fixing unit and at mutually different at least three points, which are not located on a same straight line, targets, said targets being indexes for a coordinate measurement, is fixed on the lower jaw model, the reference jig fixed on the lower jaw model is fixed at a position determined by said positioning means, of said lower jaw fixing unit to fix the lower jaw model on said lower jaw fixing unit, and said transfer frame is fixed on the lower jaw model in such a manner that position and posture as to the lower jaw model are substantially the same as those as to the lower jaw of the subject in a case where said transfer frame is fixed on the lower jaw of the subject, the lower jaw model is photographed by a plurality of cameras from mutually different directions so that said jaw movement simulation system determines a second data representative of relative position and posture between the lower jaw model and the reference jig fixed on the lower jaw model, as well as the first data, and said jaw movement reproducing control unit controls said lower jaw driving means of said jaw movement reproducing unit in accordance with the first data and the second data, so that the lower jaw model fixed on said lower jaw fixing unit of said jaw movement reproducing unit reproduces a movement of the lower jaw of the subject.

In the third jaw movement simulation method as mentioned above, similar to the first jaw movement simulation method, it is acceptable that the targets of said head frame, the targets of said lower jaw frame, and the targets of said transfer frame are light-emitting elements, and that in a case where the lower jaw model, with which said reference jig is integrated, is fixed on said lower jaw fixing unit and said transfer frame is fixed on the lower jaw model, and then the lower jaw model is photographed by a plurality of cameras, a pointer having a plurality of light-emitting elements, in which a positional relationship between the plurality of light-emitting elements and a tip to be in contact with a desired coordinate measurement point is known, is prepared, and said jaw movement simulation system recognizes positions of the light-emitting elements of said transfer frame, recognizes positions of the targets of said reference jig by recognition of positions of the light-emitting elements of said pointer by bringing the tip of said pointer into contact with the targets of said reference jig to provide position information of the light-emitting elements of said pointer in form of a parameter, and determines the second data in accordance with positional information as to those recognized positions of the light-emitting elements of said transfer frame and positions of the targets of said reference jig.

In the third jaw movement simulation method as mentioned above, similar to the first jaw movement simulation method, it is preferable that the targets of said head frame, the targets of said lower jaw frame, the targets of said transfer frame, and the targets of said reference jig are light-emitting elements, and that the lower jaw model, with which said reference jig is integrated, is fixed on said lower jaw fixing unit and said transfer frame is fixed on the lower jaw model, and then the lower jaw model is photographed by a plurality of cameras, whereby said jaw movement simulation system recognizes positions of the light-emitting elements of said transfer frame and positions of the light-emitting elements of said reference jig, and determines the second data in accordance with positional information as to those recognized positions of the light-emitting elements of said transfer frame and positions of the light-emitting elements of said reference jig.

To accomplish the above-mentioned object, of jaw movement simulation methods according to the present invention, as a fourth jaw movement simulation method, there is provided a jaw movement simulation method of reproducing a movement of a jaw of a subject using a jaw movement simulation system comprising:

a jaw movement image pick-up apparatus for imaging a movement of a jaw of a subject, said jaw movement image pick-up apparatus comprising a plurality of cameras for imaging the subject from mutually different directions, a head frame to be mounted on a head of the subject, said head frame having at mutually different at least three points, which are not located on a same straight line, targets visually recognized by the plurality of cameras, said targets being indexes for a coordinate measurement on images through imaging, a lower jaw frame to be fixed on a front portion of front teeth of a lower jaw of the subject, said lower jaw frame having at mutually different at least three points, which are not located on a same straight line, targets visually recognized by the plurality of cameras, said targets being indexes for a coordinate measurement on images through imaging, and a transfer frame to be fixed on a portion including an upper portion of teeth of the lower jaw of the subject, said transfer frame having at mutually different at least three points, which are not located on a same straight line, targets visually recognized by the plurality of cameras, said targets being indexes for a coordinate measurement on images through imaging;

a jaw movement arithmetic unit for detecting the targets on a first image obtained when the subject, on whose head said head frame is fixed and on whose lower jaw said lower jaw frame is fixed, is photographed by said plurality of cameras, and also detecting the targets on a second image obtained when the subject, on whose lower jaw said lower jaw frame and said transfer frame are fixed, is photographed by said plurality of cameras, to determine data representative of position and posture of the lower jaw of the subject when the head of the subject is set as a standard, in accordance with positions of the targets on the first and second images;

a jaw movement reproducing unit in which an upper jaw model patterned after at least part of an upper jaw and a lower jaw model patterned after at least part of a lower jaw are mounted, and the lower jaw model is relatively moved with respect to the upper jaw model, said jaw movement simulator comprising: a substrate; a lower jaw fixing unit on which the lower jaw model is fixed; a lower jaw fixing unit supporting member for supporting said lower jaw fixing unit in such a manner that a position and an posture of said lower jaw fixing unit in a three-dimensional space are changeable with respect to said substrate; lower jaw driving means for moving said lower jaw fixing unit supporting parts to alter the position and the posture of said lower jaw fixing unit; and an upper jaw fixing unit on which the upper jaw model is fixed in a predetermined positional relation with respect to the lower jaw model fixed on said lower jaw fixing unit in a predetermined initial position and a predetermined initial posture; and a jaw movement reproducing control unit for controlling said lower jaw driving means of said jaw movement reproducing unit in accordance with the data determined by said jaw movement arithmetic unit so that the lower jaw model fixed on said lower jaw fixing unit of said jaw movement reproducing unit reproduces a movement of the lower jaw of the subject, said jaw movement simulation method is characterized in that in a case where the lower jaw model patterned after at least part of the lower jaw of the subject is mounted on said jaw movement reproducing unit, a transfer jig for fixing a relative positional relationship between said transfer frame and a lower jaw model fixing member on which said lower jaw model is fixed, said lower jaw model fixing member having positioning means with respect to said lower jaw fixing unit, is prepared, said transfer frame is fixed on the lower jaw frame in such a manner that position and attitude as to the lower jaw model are substantially the same as those as to the lower jaw of the subject in a case where said transfer frame is fixed on the lower jaw of the subject, and said transfer frame is fixed on said transfer jig, and further a state that said lower jaw model fixing member is fixed on said transfer jig is produced, and then in this state said lower jaw model is fixed on said lower jaw model fixing member, and said lower jaw model fixing member, on which said lower jaw model is fixed, is fixed on a position of said lower jaw fixing unit, said position being determined by said positioning means, so that the lower jaw model is fixed on said lower jaw fixing unit.

In the fourth jaw movement simulation method as mentioned above, it is preferable that the targets of said head frame, the targets of said lower jaw frame, and the targets of said transfer frame are light-emitting elements.

BRIEF DESCRIPTION OF THE DRAWINGS

FIG. 3 is an illustration showing a state inside the room wherein a movement of the jaw is measured;

DESCRIPTION OF THE PREFERRED EMBODIMENTS

Here, there will be described, first, an example of a jaw movement image pick-up apparatus for presenting a jaw movement of a test subject, and an example of a lower jaw movement arithmetic unit for determining data representative of a movement of the lower jaw in accordance with images obtained through imaging by the jaw movement pick-up apparatus, and thereafter, embodiments of a jaw movement simulator and a jaw movement simulation method according to the present invention.

Figure 2A:
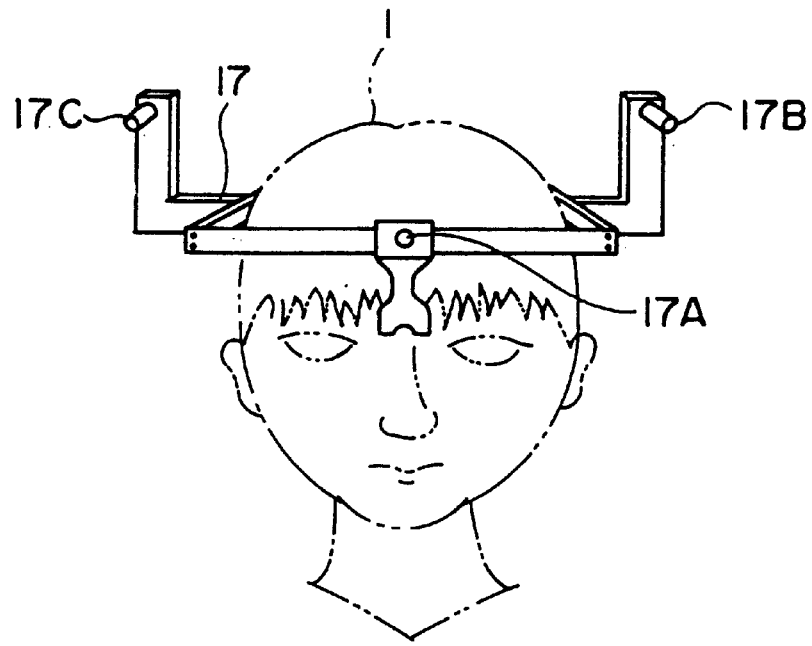
FIGS. 2(A) and 2(B) are typical illustrations each showing a head frame constituting a jaw movement image pick-up apparatus.
Figure 2B:
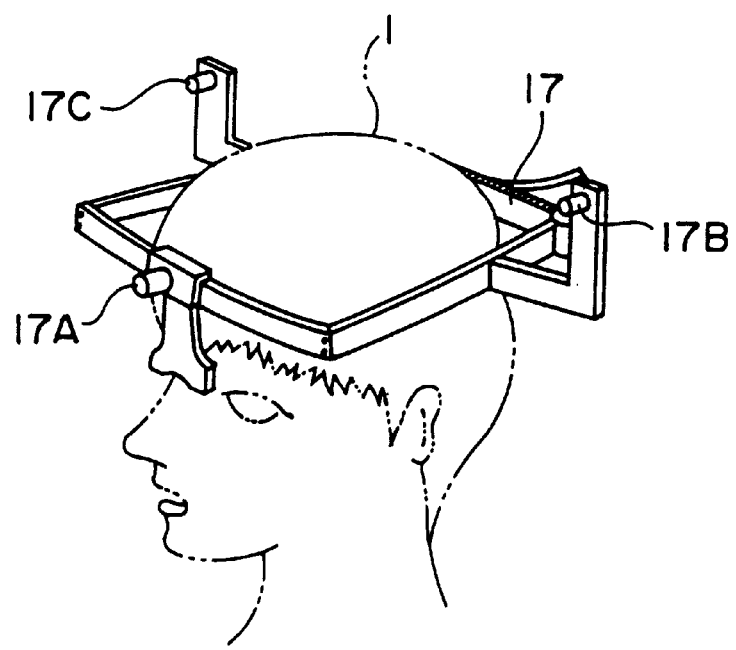

FIGS. 2(A) and 2(B) are typical illustrations each showing a head frame constituting a jaw movement image pick-up apparatus.

A head frame 17 shown in FIGS. 2(A) and 2(B) is mounted on the head of a subject 1 in its entirety. LEDs 17A, 17B and 17C, which serve as an index of the coordinate measurement, are fixed on the total three sites, that is, a site corresponding to the frontal portion of the head, and sites located at upper portions of the ears of the left and right sides, respectively and at the place higher than the top of the head, respectively. Here, the head frame 17 is mounted on the head. However, it is acceptable that the head frame 17 may be mounted on a portion moving in one united body together with the head, for example, the upper jaw instead of mounting it on the head. It is noted that the head frame includes one which is mounted on a portion moving in one united body together with the head, such as the upper jaw.

Here, those three LEDs 17A, 17B and 17C are turned on to take a photograph through two CCD cameras. Three-dimensional coordinates of the LEDs 17A, 17B and 17C are determined in accordance with images obtained through imaging by the two CCD cameras. A coordinate system as to the head area (the upper jaw) is determined in accordance with the three-dimensional coordinates thus determined.

Figure 4:
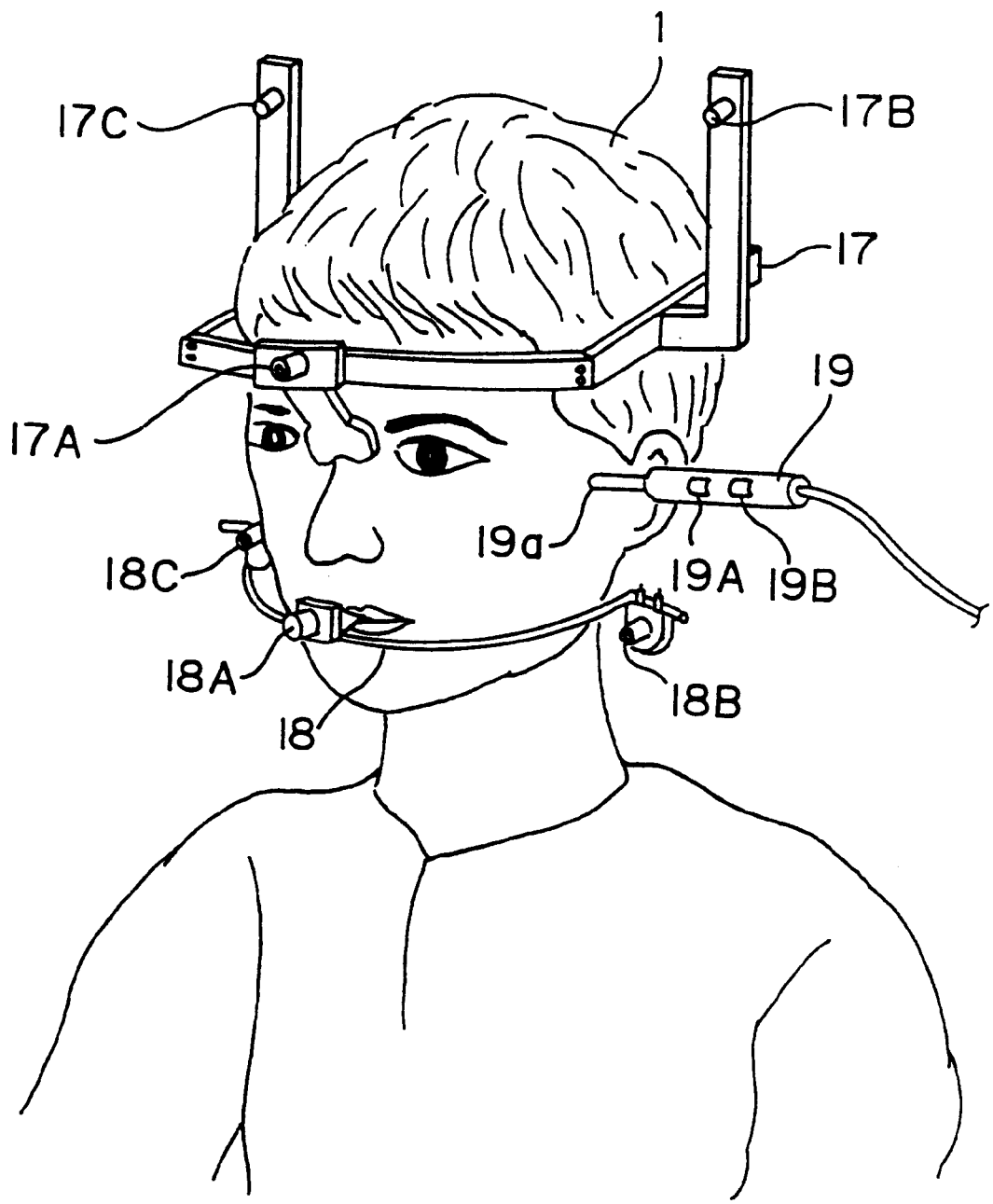
FIG. 4 is a typical illustration showing a state in which a head frame and a lower jaw frame are mounted to measure a movement of the jaw.

FIG. 3 is an illustration showing a state inside the room wherein a movement of the jaw is measured. FIG. 4 is a typical illustration showing a state in which a head frame and a frame for lower jaws are mounted to measure a movement of the jaw.

The head frame 17 is fixed on the head. As described above, on the head frame 17 there are arranged the total three LEDs 17A, 17B and 17C at the frontal portion of the head, and sites located at upper portions of the ears of the left and right sides, respectively and at the place higher than the top of the head, respectively.

A lower jaw frame 18 is fixed on lower teeth in the mouth. Also on the lower jaw frame 18 there are arranged the total three LEDs 18A, 18B and 18C at the frontal portion of the mouth and sites located at lower portions of the ears of the left and right sides, respectively.

Two LEDs 19A and 19B are included in a pointer pen 19. When a certain point is indicated by the pointer pen 19, positions of the LEDs 19A and 19B are measured, so that a position of a tip 19a of the pointer pen 19 is determined in accordance with position coordinates of the LEDs 19A and 19B.

The subject 1, on whom the head frame 17 and the lower jaw frame 18 as shown in FIG. 4 are mounted, sits down on a chair as shown in FIG. 3, and is photographed by two CCD cameras 12 and 14, which are arranged lengthways as shown in FIG. 3. Image signals obtained through imaging are inputted to a computer system 20 to determine positions of the LEDs 17A, 17B and 17C; the LEDs 18A, 18B and 18C. Thus, a movement of the lower jaw with respect to the upper jaw is measured on the basis of those positions of the LEDs thus determined. Here, a jaw movement pick-up apparatus 10 comprises the head frame 17, the lower jaw frame 18, and the two CCD cameras 12 and 14.

If the CCD cameras 12 and 14 are arranged sideways, but not lengthways as shown in FIG. 3, the CCD cameras 12 and 14 would look obliquely the subject 1 from the sides. However, here, the COD cameras 12 and 14 are arranged lengthways as shown in FIG. 3, so that both the two COD cameras 12 and 14 may photograph the subject 1 from the front. this arrangement permits, in conjunction with an arrangement that the LEDs 17B and 17C of the head frame 17 are located at the upper part than the head top of the subject 1, a very large margin up to the situation that when the subject 1 moves, anyone of the LEDs 17A, 17B and 170 is not photographed by anyone of the CCD cameras 12 and 14, and as a result it is difficult to determine a coordinate system for the upper jaw or the lower jaw.

Incidentally, the computer system 20 shown in FIG. 3 serves both as a jaw movement arithmetic unit and a jaw movement reproducing control unit. When one pays attention to the function of the jaw movement arithmetic unit of the computer system 20, the computer system 20 is referred to as a jaw movement arithmetic unit 21. And when one pays attention to the function of the jaw movement reproducing control unit of the computer system 20, the computer system 20 is referred to as a jaw movement reproducing control unit 22.

Next, it will be described how to determine data representative of a movement of the lower jaw with respect to the upper jaw on the basis of a target position on an image obtained through imaging by the two CCD cameras 12 and 14, which determination is performed in the jaw movement arithmetic unit 21.

In the jaw movement image pick-up apparatus and the jaw movement arithmetic unit shown in FIG. 3, a stereo scheme, which will be described hereinafter, is applicable.

Figure 5:
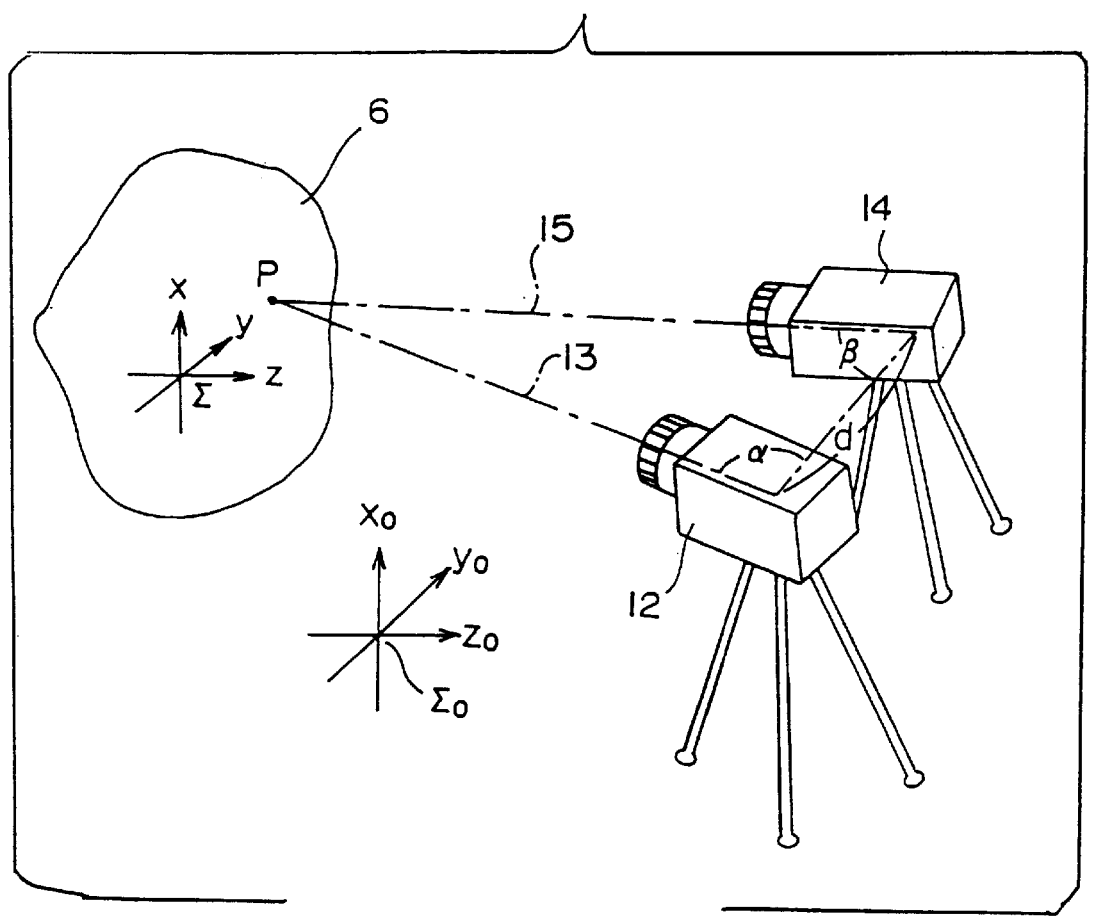
FIG. 5 is a typical illustration useful for understanding an example of a three-dimensional coordinate measurement method according to a stereo scheme.

FIG. 5 is a typical illustration useful for understanding an example of a three-dimensional coordinate measurement method according to a stereo scheme.

A camera subject 6 is photographed by the two CCD cameras 12 and 14 which are located being spaced each other by a predetermined interval d. In the event that it is possible to determine a transformation of coordinates between a two-dimensional coordinate of the image points on the respective picture planes by the two CCD cameras 12 and 14 on a point P of the camera subject 6, and an actual three-dimensional coordinate (referred to as a world coordinate) of the point P, it is possible to determine the world coordinate of the point P from the two-dimensional coordinate of the image points mentioned above.

Figure 6:
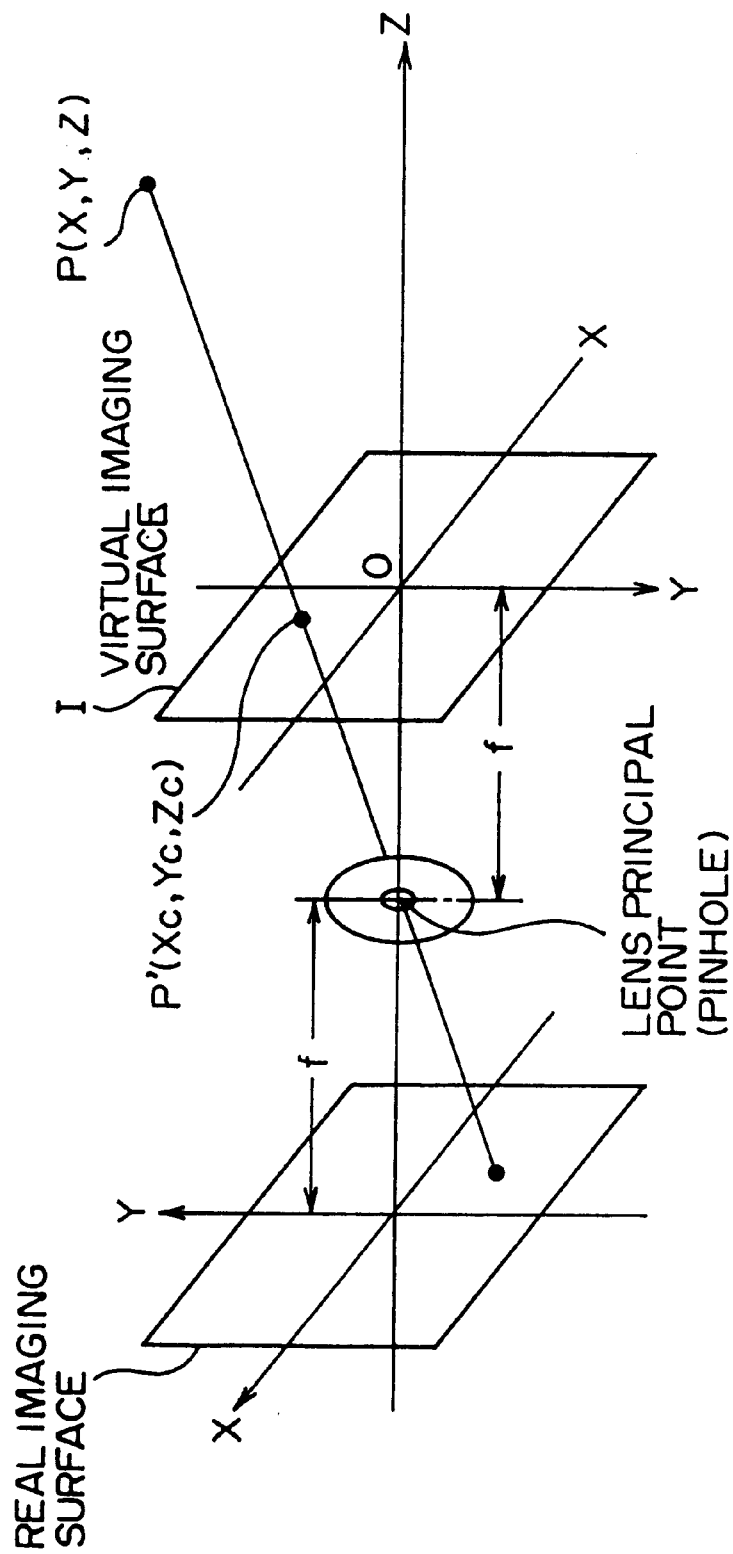
FIG. 6 is a view useful for understanding a perspective transformation model based on a pinhole camera.

FIG. 6 is an illustration of a perspective transformation model based on a pinhole camera, which is useful for understanding a way of determination of the above-mentioned transformation of coordinates.

A point P (a target point) in a three-dimensional space can be determined by an intersection of two straight lines 13 and 15 (cf. FIG. 5), and its coordinate can be described by an arbitrary world coordinate. Hence, the straight lines formed by eyes of the two CCD cameras 12 and 14 are expressed by numerical formulas, and equations thus obtained are given with simultaneous equations, so that a coordinate of their intersection or the target point P can be determined. Here, an imaging optical system by lens of cameras is modeled, and the model is referred to as a perspective transformation model. As parameters of cameras, there are position, posture, angle of view, etc.

The perspective transformation model, in which a camera is idealized, is equivalent to one in which a pinhole is opened at the center of a lens plane. An eye is defined as a straight line. Also a general imaging system using a glass lens can be expressed by such a simple model in the event that the distortion aberration is so small being negligible. In the actual camera, there is provided an arrangement of object-lens-imaging plane in the named order. This brings about an image inversion, and it is not so easy to see. For this reason, here, the imaging plane is imaginarily placed before the lens, and as a result there is provided an arrangement of object-imaging plane-lens in the named order. Since the imaging plane is considered as a standard of a coordinate system which is fixed on the camera, the center of imaging plane I is given the origin of the coordinate system.

An intersection of the imaging plane I and a point P' (Xc, Yc, Zc), which is obtained when seeing through a certain point P (X, Y, Z) in space onto the imaging plane 1, that is, an eye directed to the measurement point P, is expressed by the following equation (1).

$$\begin{bmatrix} Xc \\ Yc \\ Zc \end{bmatrix} = \begin{bmatrix} 0 \\ 0 \\ -f \end{bmatrix} + \alpha \begin{bmatrix} X \\ Y \\ f+Z \end{bmatrix}, Z=0 \quad (1)$$

where $\alpha \equiv = f/(f+Z)$

Alternatively, it is expressed by $Xc = fX/(f+Z)$ $Yc = fY/(f+Z)$, $Zc = O$ \quad (2)

As seen from the above, the perspective transformation is the nonlinear transformation. But, adding a variable, which mediates a three-dimensional coordinate, to use an expression higher in dimension by one, makes it possible to provide a linearization. This is addressed as homogeneous coordinates. One, in which three-dimensional points (X, Y, Z) are expressed by four-dimensional points (Xh, Yh, Zh, Wh) which mediates Wh, as set forth below, is a homogeneous expression.

$X = Xh/Wh$, $Y = Yh/Wh$, $Z = Zh/Wh$ \quad (3)

The perspective transformation is able to be described by 4×4 matrix operation expressed by the following equation (4).

$$\begin{bmatrix} Xch \\ Ych \\ Zch \\ Wch \end{bmatrix} = \begin{bmatrix} 1 & 0 & 0 & 0 \\ 0 & 1 & 0 & 0 \\ 0 & 0 & 0 & 0 \\ 0 & 0 & 1/f & 0 \end{bmatrix} \begin{bmatrix} X \\ Y \\ Z \\ 1 \end{bmatrix} \quad (4)$$

The above-mentioned perspective transformation is applicable when it is expressed by a coordinate system in which points P and P' are fixed on the cameras. In general, however, the point P, which is an object of a measurement, is expressed by the world coordinate system, and the point P' is expressed by a camera coordinate system which is a coordinate in which the camera center is set up to the origin looking from the camera. A transformation T for providing an association between these two coordinates, that is, the world coordinate and the camera coordinate, is expressed in the homogeneous coordinates expression including rotation and translation by the following equation (5).

$$T = \begin{bmatrix} T_{11} & T_{12} & T_{13} & T_{14} \\ T_{21} & T_{22} & T_{23} & T_{24} \\ T_{31} & T_{32} & T_{33} & T_{34} \\ 0 & 0 & 0 & 1 \end{bmatrix} \quad (5)$$

A translation from the point P in the world coordinate system to the point P' in the camera coordinate system is expressed by the following equation (6).

$$\begin{bmatrix} Xch \\ Ych \\ Zch \\ Wch \end{bmatrix} = \begin{bmatrix} 1 & 0 & 0 & 0 \\ 0 & 1 & 0 & 0 \\ 0 & 0 & 0 & 0 \\ 0 & 0 & 1/f & 0 \end{bmatrix} \begin{bmatrix} T_{11} & T_{12} & T_{13} & T_{14} \\ T_{21} & T_{22} & T_{23} & T_{24} \\ T_{31} & T_{32} & T_{33} & T_{34} \\ 0 & 0 & 0 & 1 \end{bmatrix} \begin{bmatrix} X \\ Y \\ Z \\ 1 \end{bmatrix} \quad (6)$$

$$= \begin{bmatrix} T_{11} & T_{12} & T_{13} & T_{14} \\ T_{21} & T_{22} & T_{23} & T_{24} \\ 0 & 0 & 0 & 1 \\ T_{31}/f & T_{32}/f & T_{33}/f & T_{34}/f+1 \end{bmatrix} \begin{bmatrix} X \\ Y \\ Z \\ 1 \end{bmatrix}$$

In the camera coordinate system, the imaging plane is $Zch=0$. Hence, in the two-dimensional coordinate $(Xc, Yc)$ on the imaging plane, that is, the position of pixels in the input image, the equation (6) is simplified as follows.

$$\begin{bmatrix} HcXc \\ HcYc \\ Hc \end{bmatrix} = \begin{bmatrix} Ca_{11} & Ca_{21} & Ca_{31} & Ca_{14} \\ Ca_{21} & Ca_{22} & Ca_{23} & Ca_{24} \\ Ca_{31} & Ca_{32} & Ca_{33} & Ca_{34} \end{bmatrix} \begin{bmatrix} X \\ Y \\ Z \\ 1 \end{bmatrix} \quad (7)$$

This 3×4 Ca matrix is camera parameters.

Next, there will be described a method of calibration of the camera parameters.

Figure 7:
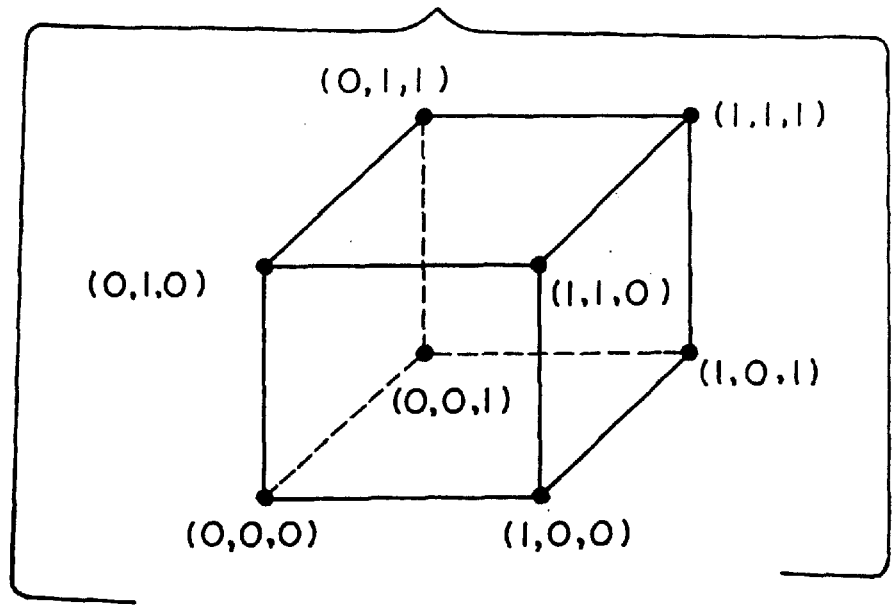
FIG. 7 is an illustration in which a calibration object for a calibration of a camera parameter is modeled.

FIG. 7 is an illustration in which a calibration object for a calibration of a camera parameter is modeled.

In order to determine a camera parameter, generally, a calibration object, in which a three-dimensional shape is known as shown in FIG. 7, that is, a reference object in which coordinates in the world coordinate system are known as eight points shown in FIG. 7, is utilized to perform a three-dimensional measurement, so that the parameter is subjected to the calibration.

In the development and the rearrangement of the equation (7), the following two expressions apply.

$Ca_{11}X+Ca_{12}Y+Ca_{13}Z+Ca_{14}-Ca_{31}(\text{vector }Xc)-Ca_{32}YXc-Ca_{33}ZXc-Ca_{34}Xc=0$ $Ca_{21}X+Ca_{22}Y+Ca_{23}Z+Ca_{24}-Ca_{31}XYc-Ca_{32}(\text{vector }Yc)-Ca_{33}ZYc-Ca_{34}Yc=0$ \quad (8)

Accordingly, it is sufficient for determining 12 unknowns from camera parameters $Ca_{11}$ to $Ca_{34}$ that 6 sets or more of a point $(X, Y, Z)$, which is a reference point in the world coordinate system, and an associated position $(Xc, Yc)$ in the camera coordinate system are established. Usually, a number of reference points not less than 6 are used to enhance the accuracy of the calibration, and an identification of parameters is established by a method of least squares. If the world coordinate $(Xi, Yi, Zi)$ of the reference point of n point and the associated camera coordinate $(Xci, Yci)$ are known, putting $Ca_{34}=1$ may introduce the following equation (9).

$$\begin{bmatrix} X_1 & Y_1 & Y_1 & 1 & 0 & 0 & 0 & 0 & -X_1X_{c1} & -Y_1Y_{c1} & -Z_1Z_{c1} \\ 0 & 0 & 0 & 0 & X_1 & Y_1 & Y_1 & 1 & -X_1X_{c1} & -Y_1Y_{c1} & -Z_1Z_{c1} \\ & & & & & \cdots & & & & & \\ X_n & Y_n & Y_n & 1 & 0 & 0 & 0 & 0 & -X_nX_{cn} & -Y_nY_{cn} & -Z_nZ_{cn} \\ 0 & 0 & 0 & 0 & X_n & Y_n & Y_n & 1 & -X_nX_{cn} & -Y_nY_{cn} & -Z_nZ_{cn} \end{bmatrix} \quad (9)$$

$$\begin{bmatrix} Ca_{11} \\ Ca_{12} \\ \vdots \\ Ca_{32} \\ Ca_{33} \end{bmatrix} = \begin{bmatrix} X_{c1} \\ Y_{c1} \\ \vdots \\ X_{cn} \\ Y_{cn} \end{bmatrix}$$

If it is expressed by $Aa \cdot Ca = Ra$ \quad (10)

then, by the method of least square, the following expression is given, $Ca = (Aa^t Aa)^{-1} Aa^t Ra$ \quad (11)

and thus the camera parameters are calibrated.

After determination of the camera parameters in this way, an object (target) to be measured, in which the three-dimensional coordinate is unknown, is arranged instead of the calibration object. Now let us consider that the three-dimensional coordinate of this target, or the target coordinate in the world coordinate system, $(X, Y, Z)$ is computed from the target coordinate $(Xc, Yc)$ in the camera coordinate system, which is obtained through imaging.

In the development and the rearrangement of equation (7), the following expressions apply.

$(Ca_{11}-Ca_{31}Xc)X+(Ca_{12}-Ca_{32}Xc)Y+(Ca_{13}-Ca_{33}Xc)Z=Ca_{34}Xc-Ca_{14}$ $(Ca_{21}-Ca_{31}Yc)X+(Ca_{22}-Ca_{32}Yc)Y+(Ca_{23}-Ca_{33}Yc)Z=Ca_{34}Yc-C(12)$

In the above-noted expressions, while three unknowns X, Y, Z exist, two equations are given. Hence, it is impossible to uniquely solve the equation (12). A solution is given by a one straight line. As a result, it is simply understood that the target exists on this straight line.

For this reason, a measurement result by another camera located at the different position in space is used together. Also in this camera, camera parameters $Ba_{11}$–$Ba_{34}$ are calibrated beforehand. When a target coordinate of the camera coordinate system, obtained by the additional camera, is expressed by $(Xb, Yb)$, the following expressions are obtained.

$(Ba_{11}-Ba_{31}Xb)X+(Ba_{12}-Ba_{32}Xb)Y+(Ba_{13}-Ba_{33}Xb)Z=Ba_{34}Xb-Ba_{14}$ $(Ba_{21}-Ba_{31}Yb)X+(Ba_{22}-Ba_{32}Yb)Y+(Ba_{23}-Ba_{33}Yb)Z=Ba_{34}Yb-B(13)$

When the expressions (12) and (13) are expressed together in the form of a matrix, the following equation (14) is obtained.

$$\begin{bmatrix} Ca_{11} - Ca_{31}Xc & Ca_{12} - Ca_{32}Xc & Ca_{13} - Ca_{33}Xc \\ Ca_{21} - Ca_{31}Yc & Ca_{22} - Ca_{32}Yc & Ca_{23} - Ca_{33}Yc \\ Ba_{11} - Ba_{31}Xb & Ba_{12} - Ba_{32}Xb & Ba_{13} - Ba_{33}Xb \\ Ba_{21} - Ba_{31}Yb & Ba_{22} - Ba_{32}Yb & Ba_{23} - Ba_{33}Yb \end{bmatrix} \quad (14)$$

$$\begin{bmatrix} X \\ Y \\ Z \end{bmatrix} = \begin{bmatrix} Ca_{34}Xc - Ca_{14} \\ Ca_{34}Yc - Ca_{14} \\ Ba_{34}Xb - Ba_{14} \\ Ba_{34}Yb - Ba_{14} \end{bmatrix}$$

Here, according to the following expressions, $$Fa = \begin{bmatrix} Ca_{34}Xc - Ca_{14} \\ Ca_{34}Yc - Ca_{14} \\ Ba_{34}Xb - Ba_{14} \\ Ba_{34}Yb - Ba_{14} \end{bmatrix} \quad Va = \begin{bmatrix} X \\ Y \\ Z \end{bmatrix} \quad (15)$$

$$Qa = \begin{bmatrix} Ca_{11} - Ca_{31}Xc & Ca_{12} - Ca_{32}Xc & Ca_{13} - Ca_{33}Xc \\ Ca_{21} - Ca_{31}Yc & Ca_{22} - Ca_{32}Yc & Ca_{23} - Ca_{33}Yc \\ Ba_{11} - Ba_{31}Xb & Ba_{12} - Ba_{32}Xb & Ba_{13} - Ba_{33}Xb \\ Ba_{21} - Ba_{31}Yb & Ba_{22} - Ba_{32}Yb & Ba_{23} - Ba_{33}Yb \end{bmatrix}$$

the equation (14) can be expressed in the form of a matrix operation as follows.

$$Fa = Qa \cdot Va \quad (16)$$

Accordingly, if the inverse matrix of Qa exists, $$Va = Qa^{-1} Fa$$

and thus the target of the world coordinate system is determined.

The stereo scheme as mentioned above is applied to determine an upper jaw coordinate system fixed on the upper jaw to the world coordinate system, and then a coordinate of the arbitrary point given in a lower jaw coordinate system fixed on the lower jaw is transformed to a coordinate value in the upper jaw coordinate system, so that a movement of the lower jaw can be determined with respect to the upper jaw. Hereinafter, this scheme will be described in detail.

[Transfer the coordinate value of the arbitrary point given by the world coordinate to the coordinate value on the upper jaw coordinate system]

Figure 8:
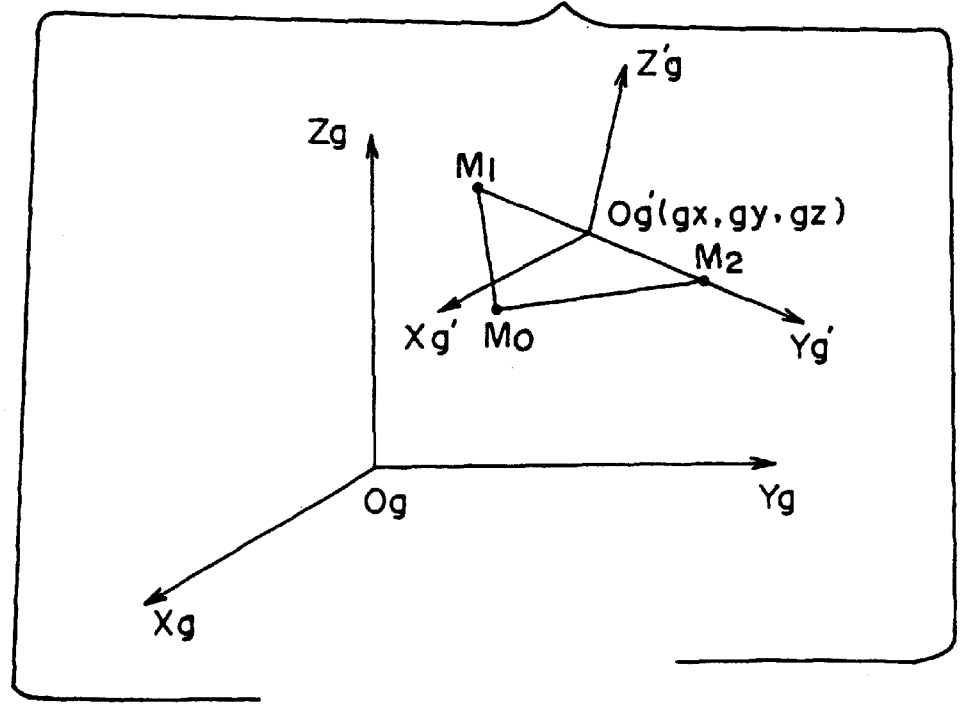
FIG. 8 is a view showing a world coordinate system and an upper jaw coordinate system.
Figure 9:
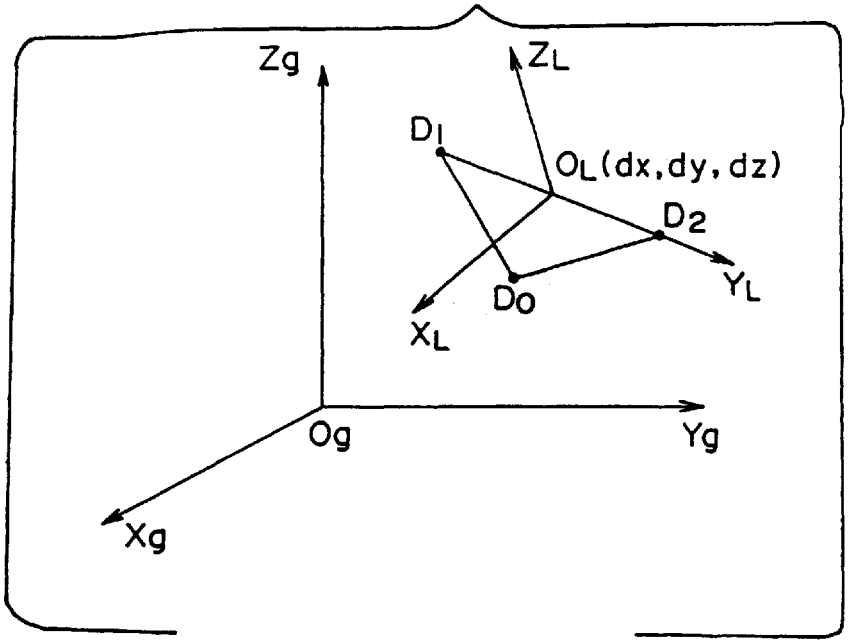
FIG. 9 is a view showing a world coordinate system and a lower jaw coordinate system.
Figure 10:
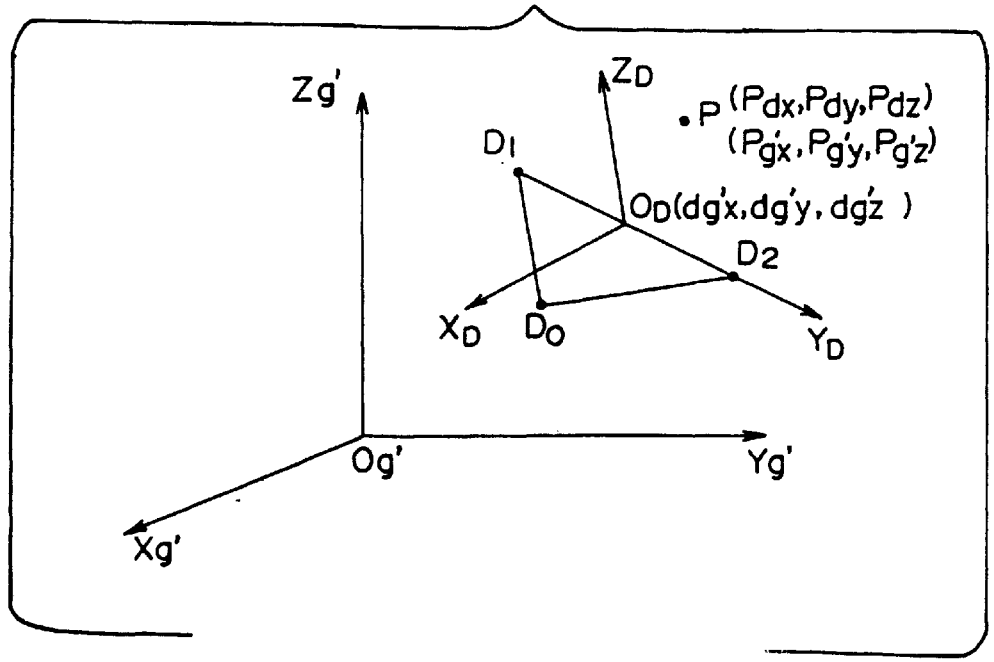
FIG. 10 is a view showing an upper jaw coordinate system and a lower jaw coordinate system.

FIG. 8 is a view showing a world coordinate system and an upper jaw coordinate system. FIG. 9 is a view showing a world coordinate system and a lower jaw coordinate system. FIG. 10 is a view showing an upper jaw coordinate system and a lower jaw coordinate system.

It is assumed that the world coordinate, the upper jaw coordinate, the coordinate value in the world coordinate system on an arbitrary point, and the coordinate value in the upper jaw coordinate system are expressed by $(0_g-X_gY_gZ_g)$, $(0_g'-X_g'Y_g'Z_g')$, $(x_g, y_g, z_g)$, and $(x_g', y_g', z_g')$, respectively.

Since both the world coordinate system and the upper jaw coordinate system are orthogonal coordinates, the following relations apply between the coordinate values of the point $(x_g, y_g, z_g)$ and $(x_g', y_g', z_g')$ $$\left. \begin{aligned} x_g &= C_{11}x_g' + C_{21}y_g' + C_{31}z_g' + g_x \\ y_g &= C_{12}x_g' + C_{22}y_g' + C_{32}z_g' + g_y \\ z_g &= C_{13}x_g' + C_{23}y_g' + C_{33}z_g' + g_z \end{aligned} \right\} \quad (17)$$

$$\left. \begin{aligned} x_g - g_x &= C_{11}x_g' + C_{21}y_g' + C_{31}z_g' \\ y_g - g_y &= C_{12}x_g' + C_{22}y_g' + C_{32}z_g' \\ z_g - g_z &= C_{13}x_g' + C_{23}y_g' + C_{33}z_g' \end{aligned} \right\} \quad (18)$$

Here, $(g_x, g_y, g_z)$ denotes the coordinate value of the upper jaw coordinate origin $0_g'$ in the world coordinate system; $(C_{11}, C_{12}, C_{13})$ a component of $X_g'$ axis unit vector in the world coordinate system; $(C_{21}, C_{22}, C_{23})$ a component of $Y_g'$ axis unit vector in the world coordinate system; and $(C_{31}, C_{32}, C_{33})$ a component of $Z_g'$ axis unit vector in the world coordinate system.

Expression of the equation (18) in the form of a determinant brings about equation (19).

$$(x_g' \ y_g' \ z_g') \begin{pmatrix} C_{11} & C_{12} & C_{13} \\ C_{21} & C_{22} & C_{23} \\ C_{31} & C_{32} & C_{33} \end{pmatrix} = (x_g - g_x \ y_g - g_y \ z_g - g_z) \quad (19)$$

∴

$$(x_g - g_x \ y_g - g_y \ z_g - g_z) \begin{pmatrix} C_{11} & C_{12} & C_{13} \\ C_{21} & C_{22} & C_{23} \\ C_{31} & C_{32} & C_{33} \end{pmatrix}^{-1} = (x_g' \ y_g' \ z_g') \quad (20)$$

Since both the world coordinate system and the upper jaw coordinate system are orthogonal coordinates, the equation (20) is expressed by the following equation (20)'.

$$(x_g - g_x y_g - g_y z_g - g_z) \begin{pmatrix} C_{11} & C_{12} & C_{13} \\ C_{21} & C_{22} & C_{23} \\ C_{31} & C_{32} & C_{33} \end{pmatrix}^{t} = (x_g' \ y_g' \ z_g') \quad (20)'$$

It is assumed that angles between the $X_g'$ axis of the upper jaw coordinates $(0_g'-X_g'Y_g'Z_g')$ and $X_g$ axis, $Y_g$ axis and $Z_g$ axis of the world coordinates $(0_g-X_gY_gZ_g)$ are denoted by $\eta_x, \eta_y$ and $\Theta_z$, respectively. Further, it is assumed that angles between the $Y_g'$ axis of the upper jaw coordinates and $X_g$ axis, $Y_g$ axis and $Z_g$ axis are denoted by $\theta_x, \theta_y, \theta_z$, respectively. Furthermore, it is assumed that angles between the $Z_g'$ axis of the upper jaw coordinates and $X_g$ axis, $Y_g$ axis and $Z_g$ axis are denoted by $\iota_x, \iota_y, \iota_z$, respectively. Then, $C_{11}, C_{21}, C_{31}, C_{12}, C_{22}, C_{32}, C_{13}, C_{23}, C_{33}$ are expressed as follows.

$(C_{11}, C_{21}, C_{31}) = (\cos \eta_x, \cos \eta_y, \cos \eta_z)$ $(C_{12}, C_{22}, C_{32}) = (\cos \theta_x, \cos \theta_y, \cos \theta_z)$ $(C_{13}, C_{23}, C_{33}) = (\cos \iota_x, \cos \iota_y, \cos \iota_z)$ Substitute the above expressions for the equation (20), then the following equation (21) is obtained.

$$(x_g - g_x \ y_g - g_y \ z_g - g_z) \begin{pmatrix} \cos\eta_x & \cos\theta_x & \cos\iota_x \\ \cos\eta_y & \cos\theta_y & \cos\iota_y \\ \cos\eta_z & \cos\theta_z & \cos\iota_z \end{pmatrix}^{-1} = (x_g' \ y_g' \ z_g') \quad (21)$$

The upper jaw coordinates $(0_g'-X_g'Y_g'Z_g')$ are determined in accordance with the following manner.

It is assumed that the coordinate values of three points $M_0, M_1$ and $M_2$, which determine the upper jaw coordinate system, in the world coordinate system are expressed by $$M_0 = (m_{g0x}, m_{g0y}, m_{g0z})$$

$$M_1 = (m_{g1x}, m_{g1y}, m_{g1z})$$

$$M_2 = (m_{g2x}, m_{g2y}, m_{g2z})$$

An origin $0_g'$ of the upper jaw coordinate system is given as the middle point between points $M_1$ and $M_2$.

$$0_g'(g_x, g_y, g_z) \qquad (22)$$

A direction of a $Y_g'$ axis is expressed by a direction of (Vector $0_g'M_2$)

$$(\text{Vector } 0_g'M_2) = (\text{Vector } Y_g') = (m_{g2x} - g_x, m_{g2y} - g_y, m_{g2z} - g_z) \qquad (23)$$

An $Z_g'$ axis is given as a normal of planes $M_0, M_1$ and $M_2$.

(Vector $Z_g'$) coincident with the $Z_g'$ axis and the (Vector $X_g'$) coincident with the $X_g'$ axis are determined as follows.

$$(\text{Vector} Z_g') = (\text{Vector} Y_g') \times (\text{Vector} 0_g'M_0)$$

$$(\text{Vector} X_g') = (\text{Vector} Z_g') \times (\text{Vector} Y_g')$$

In this manner, the upper jaw coordinates $(0_g'-X_g'Y_g'Z_g')$ are determined.

Here, the components of (Vector$X_g'$), (Vector$Y_g$), (Vector$Z_g'$) in the world coordinate system are expressed as follows.

$$(\text{Vector } X_g') \, (e_{xx}, e_{xy}, e_{xz}) \qquad (24)$$

$$(\text{Vector } Y_g') \, (e_{yx}, e_{yy}, e_{yz}) \qquad (25)$$

$$(\text{Vector } Z_g') \, (e_{zx}, e_{zy}, e_{zz}) \qquad (26)$$

Assuming that a unit vector of the $X_g$ axis in the world coordinate system is expressed by (Vector $X_g$) (1, 0, 0); a unit vector of the $Y_g$ axis, (Vector$Y_g$) (0, 1, 0); and a unit vector of the $Z_g$ axis, (Vector$Z_g$) (0, 0, 1), in view of the fact that $\eta_x$, $\eta_y$, $\eta_z$ denote angles between the $X_g'$ axis of the upper jaw coordinates and the respective axes of the world coordinates; $\theta_x$, $\theta_y$, $\theta_z$ denote angles between the $Y_g'$ axis of the upper jaw coordinates and the respective axes of the world coordinates; and $\iota_x$, $\iota_y$, $\iota_z$ denote angles between the $Z_g'$ axis of the upper jaw coordinates and the respective axes of the world coordinates, the following expressions apply through the inner product.

$$\left.\begin{array}{l}(\text{vector } X_g') \cdot (\text{vector } x_g) = |(\text{vector } X_g')||(\text{vector } x_g)|\cos\eta_x \\ (\text{vector } X_g') \cdot (\text{vector } y_g) = |(\text{vector } X_g')||(\text{vector } y_g)|\cos\eta_y \\ (\text{vector } X_g') \cdot (\text{vector } z_g) = |(\text{vector } X_g')||(\text{vector } z_g)|\cos\eta_z \end{array}\right\} \quad (27)$$

$$\left.\begin{array}{l}(\text{vector } Y_g') \cdot (\text{vector } x_g) = |(\text{vector } Y_g')||(\text{vector } x_g)|\cos\theta_x \\ (\text{vector } Y_g') \cdot (\text{vector } y_g) = |(\text{vector } Y_g')||(\text{vector } y_g)|\cos\theta_y \\ (\text{vector } Y_g') \cdot (\text{vector } z_g) = |(\text{vector } Y_g')||(\text{vector } z_g)|\cos\theta_z \end{array}\right\} \quad (28)$$

$$\left.\begin{array}{l}(\text{vector } Z_g') \cdot (\text{vector } x_g) = |(\text{vector } Z_g')||(\text{vector } x_g)|\cos\iota_x \\ (\text{vector } Z_g') \cdot (\text{vector } y_g) = |(\text{vector } Z_g')||(\text{vector } y_g)|\cos\iota_y \\ (\text{vector } Z_g') \cdot (\text{vector } z_g) = |(\text{vector } Z_g')||(\text{vector } z_g)|\cos\iota_z \end{array}\right\} \quad (29)$$

Therefore, from the equation (27), $$\left.\begin{array}{l}\cos\eta_x = \dfrac{e_{xx}}{\sqrt{e_{xx}^2 + e_{xy}^2 + e_{xz}^2}} \\[6pt] \cos\eta_y = \dfrac{e_{xy}}{\sqrt{e_{xx}^2 + e_{xy}^2 + e_{xz}^2}} \\[6pt] \cos\eta_z = \dfrac{e_{xz}}{\sqrt{e_{xx}^2 + e_{xy}^2 + e_{xz}^2}} \end{array}\right\} \quad (30)$$

From the equation (28), $$\left.\begin{array}{l}\cos\theta_x = \dfrac{e_{yx}}{\sqrt{e_{yx}^2 + e_{yy}^2 + e_{yz}^2}} \\[6pt] \cos\theta_y = \dfrac{e_{yy}}{\sqrt{e_{yx}^2 + e_{yy}^2 + e_{yz}^2}} \\[6pt] \cos\theta_z = \dfrac{e_{yz}}{\sqrt{e_{yx}^2 + e_{yy}^2 + e_{yz}^2}} \end{array}\right\} \quad (31)$$

From the equation (29), $$\left.\begin{array}{l}\cos\iota_x = \dfrac{e_{zx}}{\sqrt{e_{zx}^2 + e_{zy}^2 + e_{zz}^2}} \\[6pt] \cos\iota_y = \dfrac{e_{zy}}{\sqrt{e_{zx}^2 + e_{zy}^2 + e_{zz}^2}} \\[6pt] \cos\iota_z = \dfrac{e_{zz}}{\sqrt{e_{zx}^2 + e_{zy}^2 + e_{zz}^2}} \end{array}\right\} \quad (32)$$

Form the equations (30), (31) and (32), the following expression is determined.

$$\begin{pmatrix} \cos\eta_x & \cos\theta_x & \cos\iota_x \\ \cos\eta_y & \cos\theta_y & \cos\iota_y \\ \cos\eta_z & \cos\theta_z & \cos\iota_z \end{pmatrix}^{-1}$$

Using the equation (22), when the coordinate value of an arbitrary point P in the world coordinate system $(0_g-X_gY_gZ_g)$ is given by $(x_g, y_g, z_g)$ the coordinate value $(x_g'y_g'z_g')$ of the upper jaw coordinates is obtained by the following expression $$(x_g' \; y_g' \; z_g') \begin{pmatrix} \cos\eta_x & \cos\theta_x & \cos\iota_x \\ \cos\eta_y & \cos\theta_y & \cos\iota_y \\ \cos\eta_z & \cos\theta_z & \cos\iota_z \end{pmatrix}^{-1} \cdot (x_g - g_x \; y_g - g_y \; z_g - g_z) \quad (33)$$

Since both the world coordinate system and the upper jaw coordinate system are orthogonal coordinates, it is similar also in equation (34).

$$(x_g' \; y_g' \; z_g') \begin{pmatrix} \cos\eta_x & \cos\theta_x & \cos\iota_x \\ \cos\eta_y & \cos\theta_y & \cos\iota_y \\ \cos\eta_z & \cos\theta_z & \cos\iota_z \end{pmatrix}^{t} (x_g - g_x \; y_g - g_y \; z_g - g_z) \quad (34)$$

[Transfer the coordinate value of the arbitrary point given by the lower jaw coordinate to the coordinate value on the upper jaw coordinate system]

It is assumed that the coordinate values on the world coordinate system $(0_g-X_gY_gZ_g)$ of three points $D_0, D_1, D_2$, which determine the lower jaw coordinate system, are expressed by $D_0(d_{g0x}, d_{g0y}, d_{g0z})$ $D_1(d_{g1x}, d_{g1x}, d_{g1z})$ $D_2(d_{g2x}, d_{g2y}, d_{gz})$ The lower jaw coordinate system is determined in a similar fashion to that of the upper jaw coordinate system. A transfer matrix L from the world coordinate to the lower jaw coordinate is determined.

Thus, the coordinate values $(x_d, y_d, z_d)$ in the lower jaw coordinate system on the point represented by $(x_g, y_g, z_g)$ in the world coordinate system is determined by the following equation.

$$(x_d y_d z_d) = (x_g - d_x, y_g - d_y, z_g - d^z)L \quad (35)$$

where $(d_x, d_y, d_z)$ denotes the origin $0_D$ of the lower jaw coordinate in the world coordinate system.

The coordinate values in the world coordinate system $(0_g - X_g Y_g Z_g)$ on three points $M_0, M_1, M_2$, which determine the upper jaw coordinate system $(0_g' - X_g' Y_g' Z_g')$, are expressed by $M_0(m_{g0x}, m_{g0y}, m_{g0z})$ $M_1(m_{g1x}, m_{g1y}, m_{g1z})$ $M_2(m_{g2x}, m_{g2y}, m_{g2z})$ The upper jaw coordinate system is determined in accordance with the above-mentioned fashion, and a transformation matrix M of the upper jaw coordinates is determined from the world coordinates.

The transformation matrix M is used to determine the coordinate values in the upper jaw coordinate system on points $D_0, D_1, D_2$ which determine the lower jaw coordinate system.

$$\left.\begin{array}{l} M_0(m'_{g0x}, m'_{g0y}, m'_{g0z}) \\ M_1(m'_{g1x}, m'_{g1y}, m'_{g1z}) \\ M_1(m'_{g2x}, m'_{g2y}, m'_{g2z}) \end{array}\right\} \quad (36)$$

From the equation (36) representative of the coordinate values on three points $D_0, D_1, D_2$ in the upper jaw coordinate system, a transformation matrix L I from the upper jaw coordinate system to the lower jaw coordinate system is determined in accordance with the above-mentioned scheme.

An arbitrary point P exists, and the coordinate of the point is given in the lower jaw coordinate system as follows.

$$P(p_{dx}, p_{dy}, p_{dz}) \quad (37)$$

If the coordinate of the point P is given in the world coordinate system, it is transferred to the coordinate value in the lower jaw coordinate system in accordance with the equation (35).

Providing that the coordinate value, when the point P is observed in the lower jaw coordinate system, is expressed by $$P(p_{gx}', p_{gy}', p_{gz}') \quad (38)$$

the following relationship is established between the equation (37) and the equation (38).

$$(p_{gx}' - d_{gx}' p_{gy}' - d_{gy}' p_{gz}' - d_{gz}')L' = (p_{dx} p_{dy} p_{dz}) \quad (39)$$

where $(d_{gx}', d_{gy}', d_{gz}')$ denotes the coordinate value of the origin $0_D$ of the lower jaw coordinate in the upper jaw coordinate system.

Thus, when the coordinate value on an arbitrary point p in the lower jaw coordinate system is given by $(p_{dx}, p_{dy}, p_{dz})$, the coordinate value $(p_{gx}', p_{gy}', p_{gz}')$ on the point P in the upper jaw coordinate system is obtained from the following equation (40).

$$(p_{gx}' - d_{gx}' p_{gy}' - d_{gy}' p_{gz}' - d_{gz}') = (p_{dx} p_{dy} p_{dz})L'^{-1} \quad (40)$$

The jaw movement arithmetic unit 21 shown in FIG. 3 determines coordinates on images of the LEDs 17A, 17B and 17C; the LEDs 18A, 18B and 18C (cf. FIG. 4) on the basis of the image signal obtained in the jaw movement image pick-up apparatus 10 (which comprises the head frame 17, the lower jaw frame 18, and the two CCD cameras 12 and 14), and determines data representative of a movement of the lower jaw of the subject 1 with respect to the upper jaw.

Next, there will be explained a jaw movement simulator.

Figure 11:
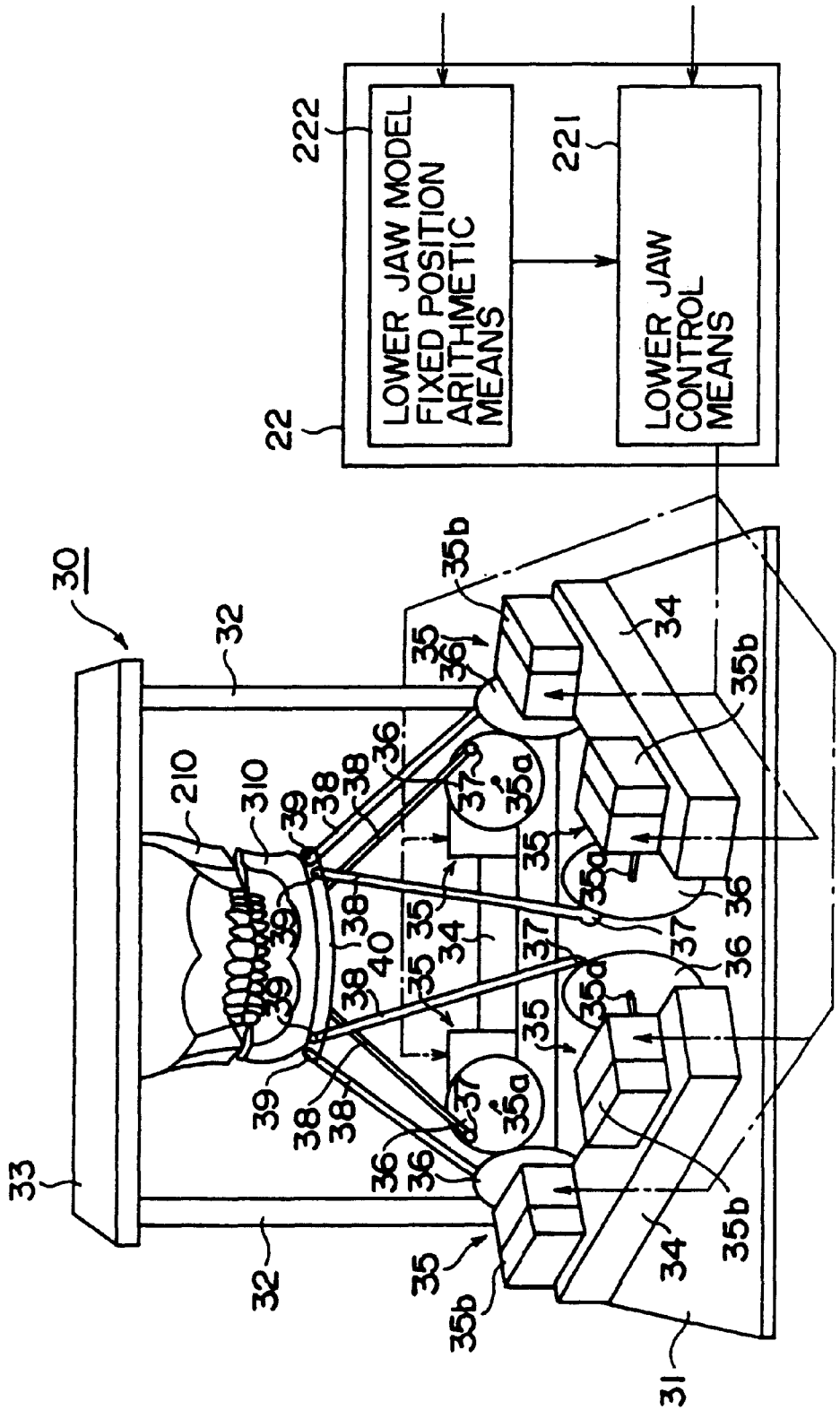
FIG. 11 is a typical illustration useful for understanding a first embodiment of a jaw movement simulator according to the present invention.

FIG. 11 is a typical illustration useful for understanding a first embodiment of a jaw movement simulator according to the present invention.

A jaw movement simulator according to the first embodiment comprises a jaw movement reproducing control unit 22, which is implemented inside the computer system 20 shown in FIG. 3, and a jaw movement reproducing unit 30 for reproducing a movement of a lower jaw model 310, on which an upper jaw model 210 and the lower jaw model 310 are detachably mounted. Here, the upper jaw model 210 and the lower jaw model 310, which are patterned after the upper jaw (upper teeth) and the lower jaw (lower teeth) of the subject 1 shown in FIG. 2, are detachably mounted on the jaw movement reproducing unit 30.

The jaw movement reproducing control unit 22 comprises a lower jaw control means 221 and a lower jaw model fixed position arithmetic means 222. An operation of the jaw movement reproducing control unit 22 will be described later.

The jaw movement reproducing unit 30 has a substrate 31 and a ceiling board 33 which is fixed on the substrate 31 through supports 32. The upper jaw model 210 is fixed on the lower surface of the ceiling board 33. Thus, the ceiling board 33 serves as the upper jaw fixing portion referred to in the present invention.

Three stands 34 are fixed on the substrate 31. Two servo motors 35 are set up on each of the stands 34, that is, six servo motors 35 in total are provided on the stands 34. Each of the servo motors 35 has an angle detector 35b for detecting an angle of rotation of a rotating shaft 35a in order to regulate an angle of rotation of the rotating shaft 35a.

The rotating shaft 35a of each of the servo motors 35 is provided with a disk type of horn 36 of which a center is fixed on the rotating shaft of the the servo motor 35.

Figure 12:
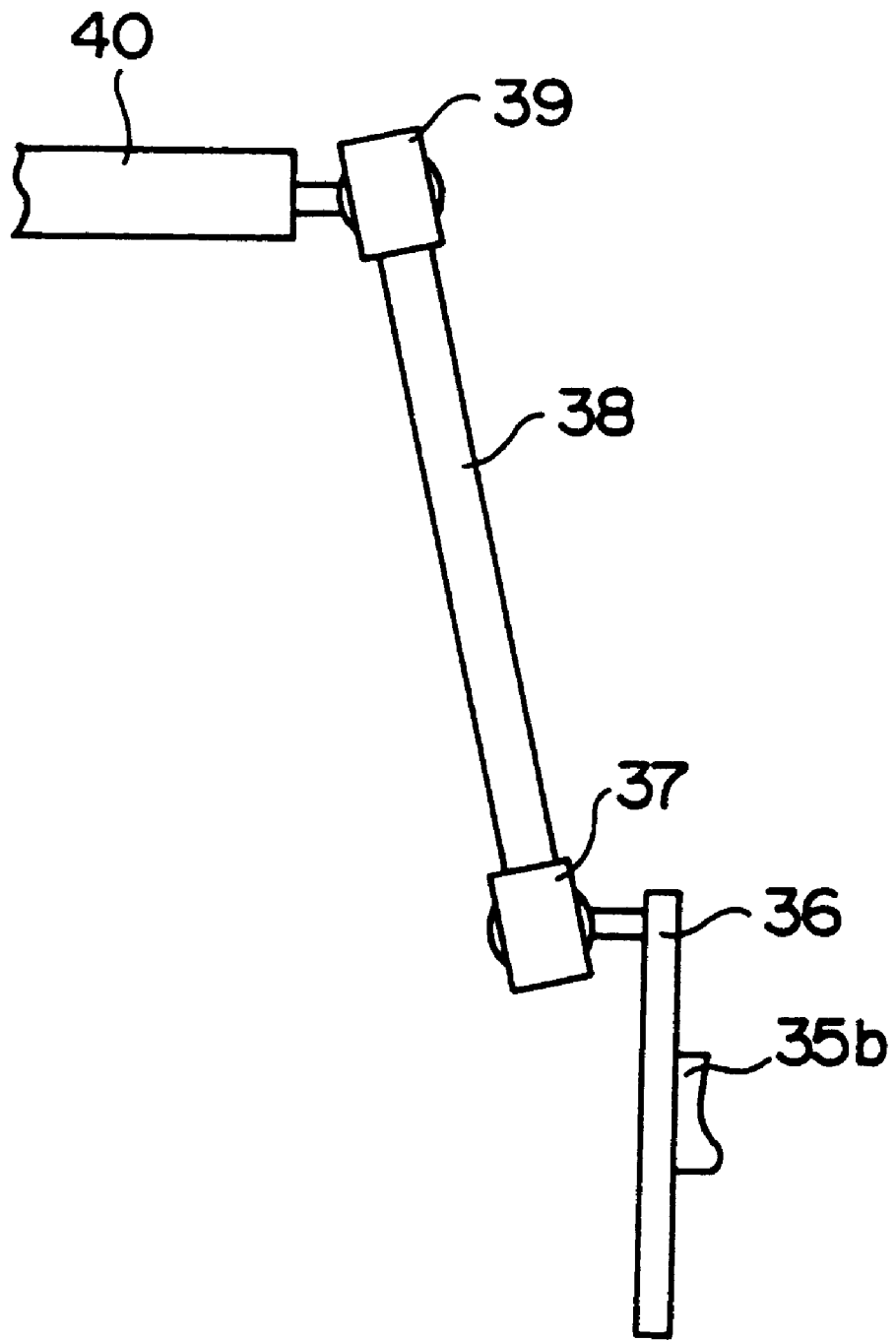
FIG. 12 is a typical illustration showing a connection structure between a horn and an operating plate.

FIG. 12 is a typical illustration showing a connection structure between a horn 36 and an operating plate 40.

One end of the horn 36 is coupled with one end of a link 38 through a ball joint 37. Another end of the link 38 is coupled with the operating plate 40 through another ball joint 39. The lower jaw model 310 is detachably fixed on the upper surface of the operating plate 40.

The operating plate 40 is supported by 6 arms 38 as shown in FIG. 11. When the rotating shafts 35a of 6 servo motors 35 are rotated, the operating plate 40 is moved, so that the lower jaw model 310 fixed on the operating plate 40 is relatively moved with respect to the upper jaw model 210 fixed on the ceiling board 33. The operating plate 40 is supported by 6 arms 38, and those 6 arms 38 are independently movable. Accordingly, the lower jaw model 310 fixed on the operating plate 40 is able to be changed in position and attitude on a three-dimensional basis. That is, there is arranged a 6 degree of freedom of actuator according to a so-called parallel mechanism.

According to the conventional articulator, the shape or the structure of the upper jaw, the lower jaw and the condyle of the human body is simulated. In the event that it is the main purpose that a movement of the lower jaw is simulated, it is easier in control of a movement of the lower jaw model that the parallel mechanism shown in FIG. 11 is adopted, rather than simulating the skeleton (e.g. condyle) of the human body in the shape or the structure.

The lower jaw control means 221 of the jaw movement reproducing control unit 22 receives data representative of a movement of the lower jaw with respect to the upper jaw of the subject 1, which data are determined in the jaw movement arithmetic unit 21 (FIG. 3) in accordance with the manner as mentioned above. Then, the lower jaw control means 221 controls based on the data thus received the respective angles of rotation of the rotating shafts 35a of the six servo motors 35 so that the lower jaw model 310 fixed on the operating plate 40 offers the same movement as the relative movement of the lower jaw with respect to the upper jaw of the subject 1. In order that the lower jaw model 310 offers the same movement as the lower jaw of the subject 1, there is a need to exactly identify an arrangement position of the lower jaw model 310 with respect to the operating plate 40. According to the present embodiment, an exact arrangement position of the lower jaw model 310 with respect to the operating plate 40 is detected in the manner as described below.

Figure 13A:
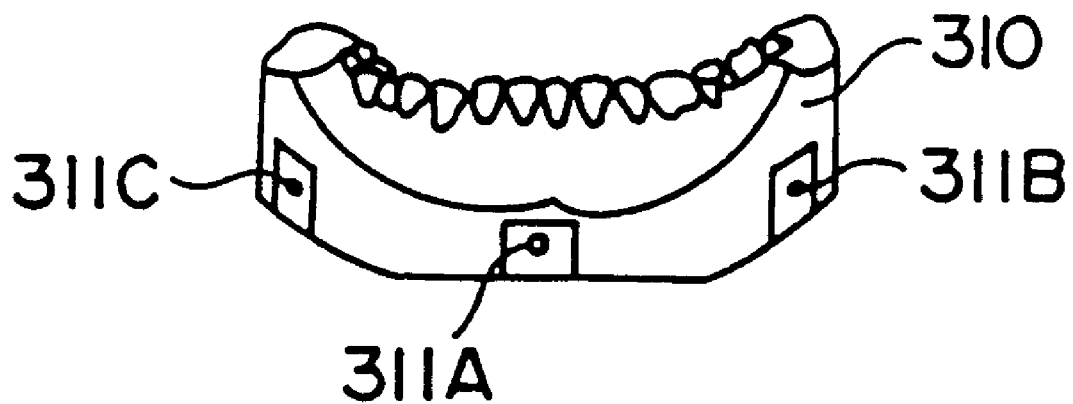
FIG. 13(A) is a front view of a lower jaw model in which a reference plate is fixed.
Figure 13B:
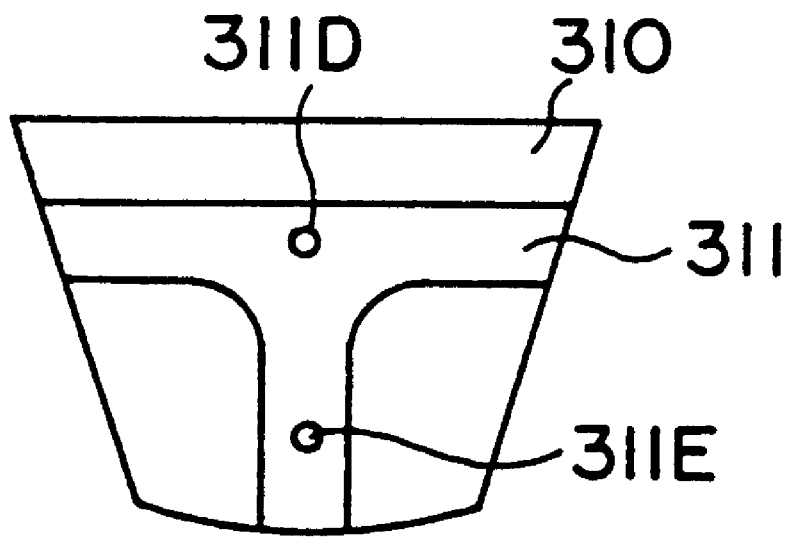
FIG. 13(B) is a bottom view of a lower jaw model in which a reference plate is fixed.

FIG. 13(A) is a front view of a lower jaw model in which a reference plate is fixed. FIG. 13(B) is a bottom view of a lower jaw model in which a reference plate is fixed.

A reference plate 311 is fixed on the lower jaw model 310 in one united body when the lower jaw model 310 is produced. Looking from the bottom of the lower jaw model 310, the reference plate 311 is shaped as a T. The T-like shaped reference plate 311 has two pins 311D and 311E for positioning to the operating plate 40 (FIG. 11). Three ends of the T-like shaped reference plate 311 are bent perpendicularly, and are provided with three reference point marks 311A, 311B and 311C (for example, holes) at the same height position with respect to the bottom of the lower jaw model 310, respectively. On the other hand, the operating plate 40 is provided with holes to be engaged with the pins 311D and 311E on the reference plate 311 at the positions associated with the pins 311D and 311E.

In this manner, the lower jaw model 310, on which the reference plate 311 is fixed, is fixed on the operating plate 40, and when a movement of the jaw of the subject 1 is photographed, the lower jaw frame mounted on the lower jaw of the subject 1 is mounted on the lower jaw model 310 fixed on the-operating plate 40 at the same position as the time of photographing for the subject 1. In this condition, while the lower jaw frame is photographed by the two cameras 12 and 14 shown in FIG. 3, the reference point marks 311A, 311B and 311C are pointed with the pointer pen 19 (cf. FIG. 4). This makes it possible to determine a positional relationship among three LEDs 18A, 18B and 18C of the lower jaw frame 18 mounted in the same condition as the time of photographing for the subject 1 and the reference point marks 311A, 311B and 311C of the reference plate 311 fixed on the lower jaw model 310 in one united body, and thereby determining an arrangement position of the lower jaw model 310 on the operating plate 40. That is, the lower jaw model fixed position arithmetic means 222, which constitutes the jaw movement reproducing control unit 22, receives information representative of a relative positional relationship among three LEDs 18A, 18B and 18C of the lower jaw frame 18 mounted on the lower jaw model 310 and the reference point marks 311A, 311B and 311C of the reference plate 311 fixed on the lower jaw model 310. Then the lower jaw model fixed position arithmetic means 222 determines, based on the information thus received, data representative of a fixed position of the lower jaw model 310 with respect to the operating plate 40. Here, this data is determined in the form of data representative of a coordinate system fixed on the lower jaw model 310 on the operating plate 40 when the operating plate 40 is set up to a predetermined initial state (the initial position and the initial attitude). The data thus determined in the lower jaw model fixed position arithmetic means 222 is fed to the lower jaw control means 221. Then, the lower jaw control means 221 controls, based on both the data representative of a movement of the lower jaw with respect to the upper jaw of the subject 1, which data is fed from the jaw movement arithmetic unit 21 (FIG. 3), and the data representative of a coordinate system fixed on the lower jaw model 310 on the operating plate 40, which data is determined in the lower jaw model fixed position arithmetic means 222, the respective angles of rotation of the rotating shafts 35a of the six servo motors 35 so that a movement of the lower jaw with respect to the upper jaw of the subject 1 at the time of photographing is reproduced. Here, first, the operating plate 40 on which the lower jaw model 310 is fixed is set up to a predetermined initial position, and then the upper jaw model 210 is fixed on the ceiling board 33 in such a manner that the upper jaw model 210 offers a predetermined initial state with respect to the lower jaw model 310 on the operating plate 40 set up to the predetermined initial position (e.g. such a state that the upper teeth and the lower teeth are occluded is addressed as the initial state). The lower jaw control means 221 controls a movement of the lower jaw model starting from the initial state. This procedure makes it possible for the jaw movement reproducing unit 30 shown in FIG. 11 to reproduce the movement of the lower jaw with respect to the upper jaw of the subject 1.

Figure 14:
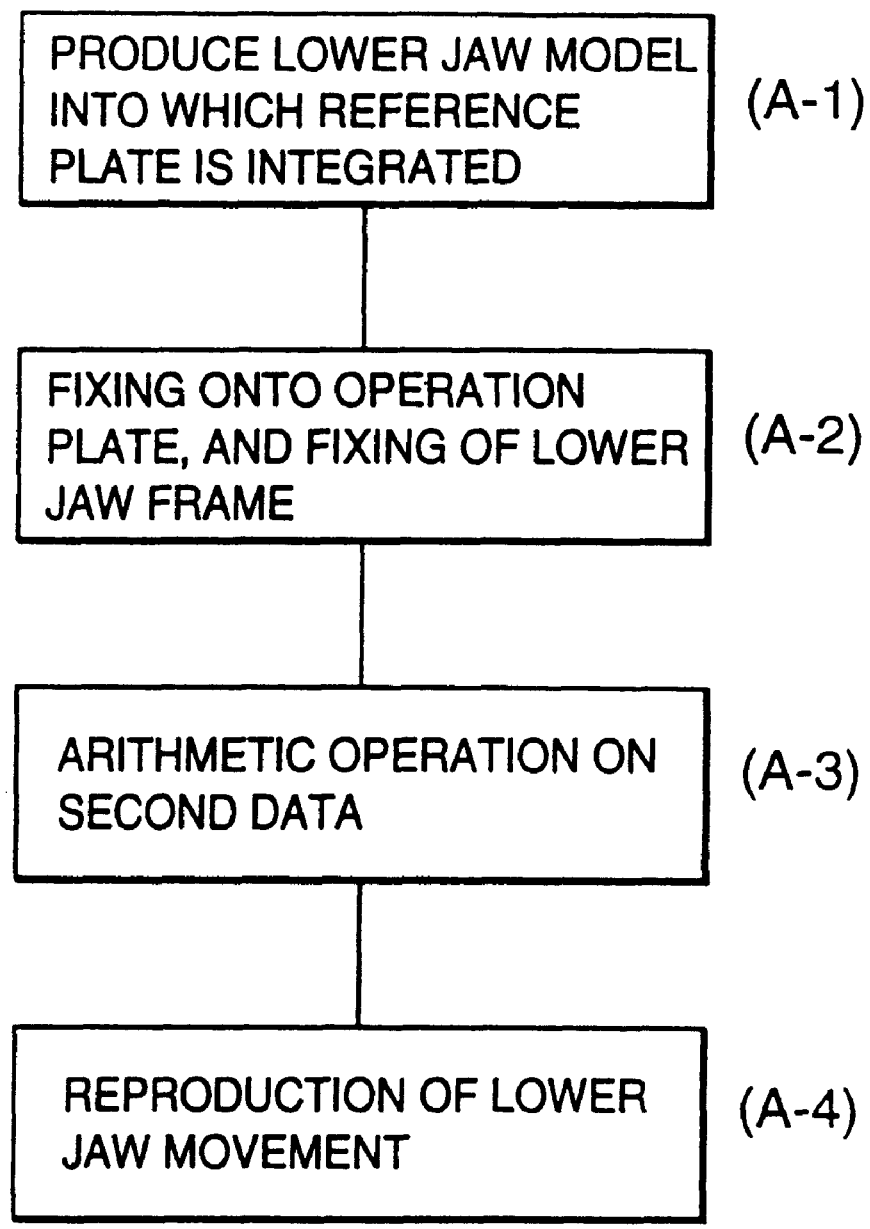
FIG. 14 is a flowchart useful for understanding a method of determining an exact located position of a lower jaw model onto an operating plate.

FIG. 14 is a flowchart useful for understanding a method of determining an exact located position of a lower jaw model 310 onto an operating plate 40 (cf. FIG. 11).

In step A-1, in order to arrange the lower jaw model 310 patterned after a lower jaw of a test subject onto the operating plate 40, there is produced the lower jaw model 310 on which a reference plate 311, as positioning means for the operating plate 40, is fixed in a unitary body. The reference plate 311 has two pins 311D and 311E, and in addition three reference point marks 311A, 311B and 311C which serve as index of a coordinate measurement. The reference plate 311, which is fixed on the lower jaw model 310 in a unitary body, is engaged with apertures (not illustrated) of the operating plate 40, which apertures are formed to be engaged with the pins 311D and 311E, so that the lower jaw model 310 is fixed on the operating plate 40. Further, the lower jaw frame 18 (cf. FIG. 4) is fixed on the lower jaw model 310 in such a manner that when a position and a posture of the lower jaw frame 18 to the lower jaw model 310 becomes the same as a position and a posture of the lower jaw frame 18 to the jaw of a test subject when the lower jaw frame 18 is fixed on the jaw of the test subject (step A-2).

In this state, the lower jaw model 310 is photographed by a plurality of cameras, for example, two cameras 12 and 14 shown in FIG. 3. Thus, according to the present embodiment, the lower jaw model fixed position arithmetic means 222 of the jaw movement reproducing control unit 22 shown in FIG. 11 is used to determine the second data representative of the relative position and posture between the lower jaw model 310 and the reference plate 311 fixed onto the lower jaw model 310 in a unitary body (step A-3). The reference plate 311 is unequivocally determined in a positional relation with the operating plate 40 by two pins 311D and 311E. Consequently, the second data is representative of the position and posture of the lower jaw model 310 to the operating plate 40. It is noted that at the previous stage, that is, at the stage in which the head frame 17 and the lower jaw frame 18 are mounted on the test subject 1 to photograph the behavior of the jaw of the test subject 1 by two cameras 12 and 14 shown in FIG. 3, there has been determined by the jaw movement arithmetic unit 21 the first data representative of the behavior of the lower jaw of the test subject 1 with respect to the upper jaw of the test subject 1.

In case of the example shown in FIGS. 13(A) and (B), three reference point marks 311A, 311B and 311C are, for example, holes or apertures, but not light-emitting elements. For this reason, here, there is prepared the pointer pen 19 having two LEDs 19A and 19B, as shown in FIG. 4, in which a positional relation between the LEDs 19A and 19B and the tip 19a to be in contact with the coordinate measurement point is known beforehand, and the reference point marks 311A, 311B and 311C are touched with the tip 19a of the pointer pen 19. In this manner, the lower jaw model fixed position arithmetic means 222 recognizes the positions of the reference point marks 311A, 311B and 311C through recognition of the LEDs 19A and 19B of the pointer pen 19.

Thus, after determining the second data, the lower jaw control means 221 of the jaw movement reproducing control unit 22 shown in FIG. 11 controls six servo motors 35 of the jaw movement reproducing unit 30 in accordance with both the first data determined by the jaw movement arithmetic unit 21 and the second data determined by the lower jaw model fixed position arithmetic means 222 of the jaw movement reproducing control unit 22 (step A-4). This control makes it possible to exactly reproduce a movement of the lower jaw.

Figure 15A:
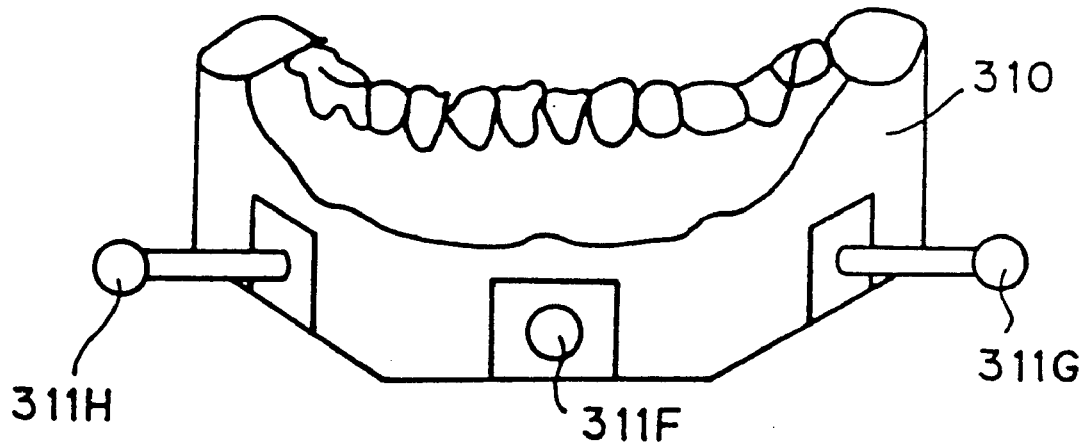
FIGS. 15(A) and 15(B) are explanatory views for another example of a reference plate integrated with a lower jaw model.
Figure 15B:
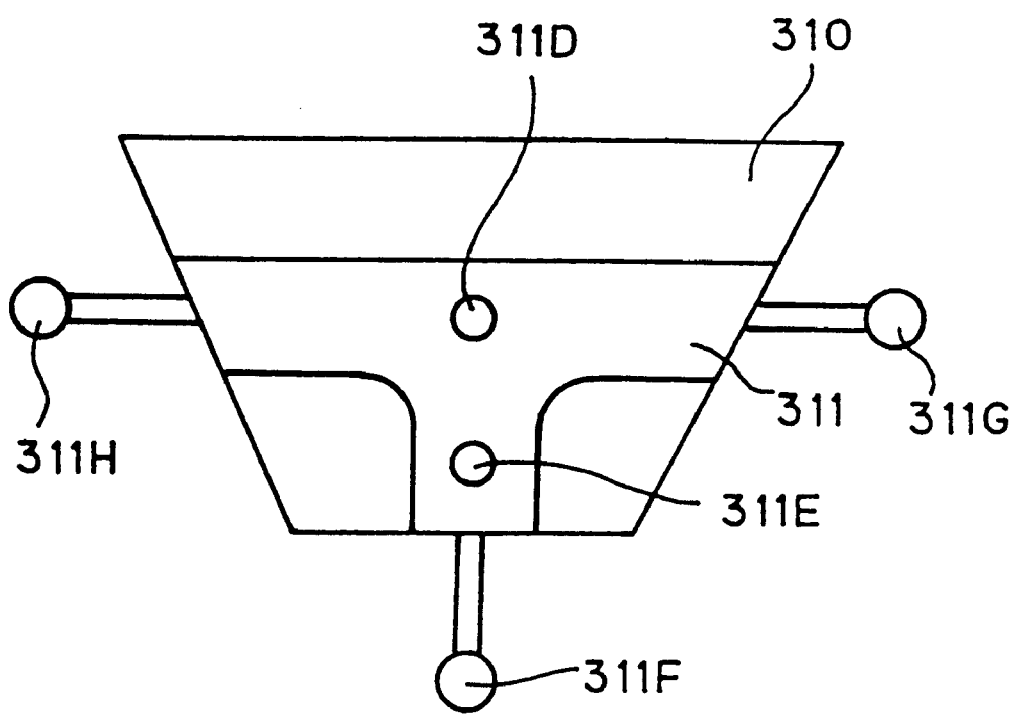

FIGS. 15(A) and 15(B) are explanatory views for another example of a reference plate integrated with a lower jaw model. FIG. 15(A) is a front view of the lower jaw model on which the reference plate is fixed. FIG. 15(B) is a bottom plan view of the lower jaw model on which the reference plate is fixed. Hereinafter, there will be described a difference of the reference plate shown in FIGS. 15(A) and 15(B) from that shown in FIGS. 13(A) and 13(B).

While the reference plate shown in FIGS. 13(A) and 13(B) has three reference point marks 311A, 311B and 311C each of which is formed with for example, a hole or aperture, the reference plate shown in FIGS. 15(A) and 15(B) has three LEDs 311F, 311G and 311H. Each of the LEDs 311F, 311G and 311H is disposed at the tip of a projected pole so that their images surely appear when they are photographed by two cameras. In case of the reference plate shown in FIGS. 15(A) and 15(B), using the LEDs 311F, 311G and 311H as the reference point marks makes it possible to avoid the necessity of an indication of the reference point marks by the pointer pen 19 when the camera photographing is conducted. Consequently, this scheme involves no error associated with an indication of the reference point marks by the pointer pen 19. Thus, it is possible to more exactly detect the position and the posture of the lower jaw model 310 with respect to the operating plate 40 (cf. FIG. 11).

Incidentally, it is acceptable that the poles, on which the LEDs 311F, 311G and 311H are fixed, respectively, are detachably mounted on the main frame of the reference plate.

A way of determining the second data representative of the position and the posture of the lower jaw model 310 with respect to the operating plate 40, in the event that the reference plate shown in FIGS. 15(A) and 15(B) is adopted instead of the reference plate shown in FIGS. 13(A) and 13(B), is the same as the explanation referring to FIG. 14, excepting that there is no need to use the pointer pen 19. Thus, a redundant explanation will be omitted.

Figure 16:
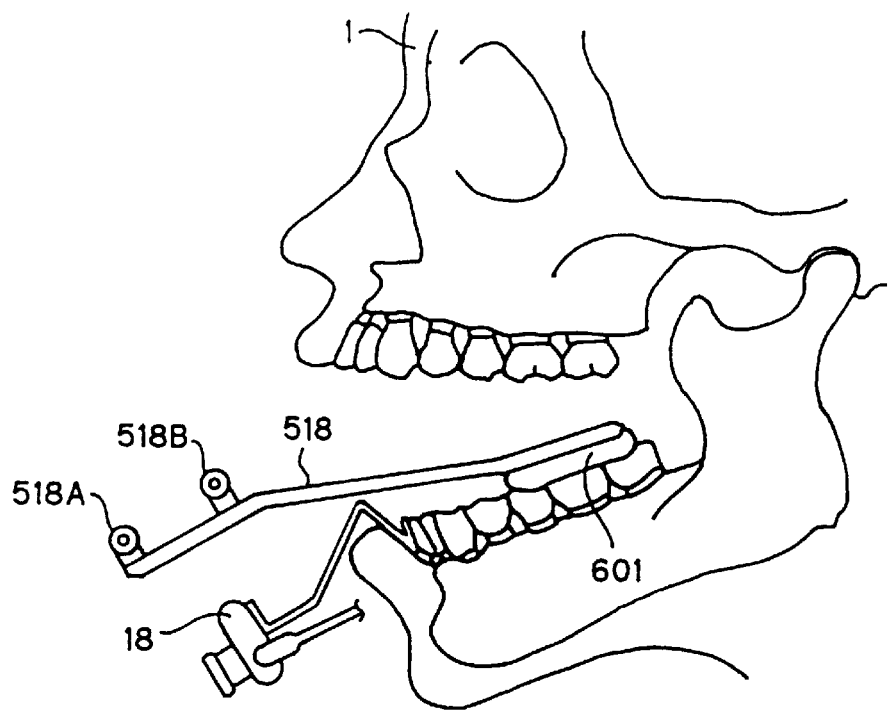
FIG. 16 is a typical illustration showing a state in which a lower jaw frame and a transfer frame are mounted on a test subject.
Figure 17:
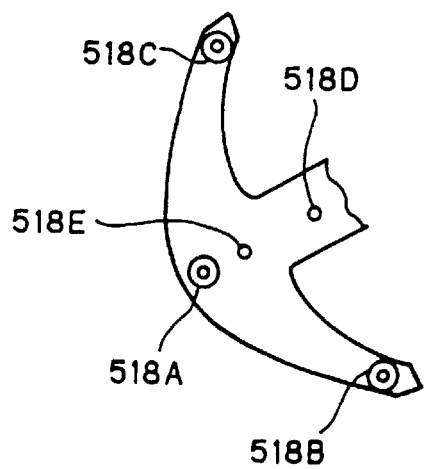
FIG. 17 is a plan view showing a part of the transfer frame.

FIG. 16 is a typical illustration showing a state in which a lower jaw frame and a transfer frame are mounted on a test subject. FIG. 17 is a plan view showing a part of the transfer frame.

As shown in FIG. 3 and FIG. 4, when the head frame 17 is mounted on the head of the test subject 1 and further the lower jaw frame 18 is mounted on the lower jaw of the test subject 1 so that a photography is conducted by two cameras 12 and 14 to measure a movement of the lower jaw with respect to the upper jaw, there is a need to set up a state that the upper teeth and the lower teeth can completely occlude. Consequently, as shown in FIG. 16, the lower jaw frame 18 is obliged to fixed on the front portion of the lower front tooth, so to speak, the lower jaw frame 18 is fixed on the standing wall, and it is restricted also in the fixing area. This involves somewhat instability. For this reason, according to the above-mentioned method, in order to determine the position and the posture of the lower jaw model 310 fixed on the operating plate 40 (cf. FIG. 1) in accordance with the above-mentioned scheme, the lower jaw frame 18 is fixed also on the lower jaw model 310. However, there is a possibility that errors somewhat occur in its fixing position.

For this reason, here, a transfer frame 518 as shown in FIG. 16 is prepared. The head frame 17 is fixed on the head of the test subject 1 and further the lower jaw frame 18 is fixed on the front portion of the lower front tooth of the lower jaw of the test subject 1, and then a photography is conducted to determine data as to a movement of the lower jaw with respect to the upper jaw. Thereafter, the transfer frame 518 is fixed on the upper portion of the lower teeth with an impression material 601, and a photography is again conducted by two cameras 12 and 14 to determine a positional relation between the lower jaw frame 18 and the transfer frame 518. Here, as shown in FIG. 17, the transfer frame 518 is also provided with three LEDs 518A, 518B and 518C, serving as index of the coordinate measurement, which are fixed at mutually separated three positions, respectively. The transfer frame 518 is further provided with two holes or apertures 518D and 518E for use in positioning with respect to the transfer jigs (cf. FIG. 19 and FIG. 20) which will be described later.

The transfer frame 518 is suitable for being surely fixed on the upper portion of the lower teeth over the large area, and in addition suitable for copying a tooth mark of the lower tooth on the impression material 601. Consequently, it is possible to mount the transfer frame 518 on the lower jaw model 310 with great reproducibility.

The jaw movement arithmetic unit 21 show in FIG. 3 determines the first data representative of behavior of the lower jaw with respect to the upper jaw of the test subject in accordance with both a movement of the lower jaw frame 18 with respect to the head frame 17 and a positional relation between the lower jaw frame 18 and the transfer frame 518. Consequently, according to the scheme which has been explained referring to FIG. 14, when the position and the posture of the lower jaw model is determined with respect to the operating plate 40, the lower jaw frame is fixed on the lower jaw model. Alternatively, fixing the transfer frame instead of the lower jaw frame onto the lower jaw model into photography by two cameras makes it possible to obtain the second data representative of the position and the posture of the lower jaw model with respect to the operating plate 40.

Figure 18:
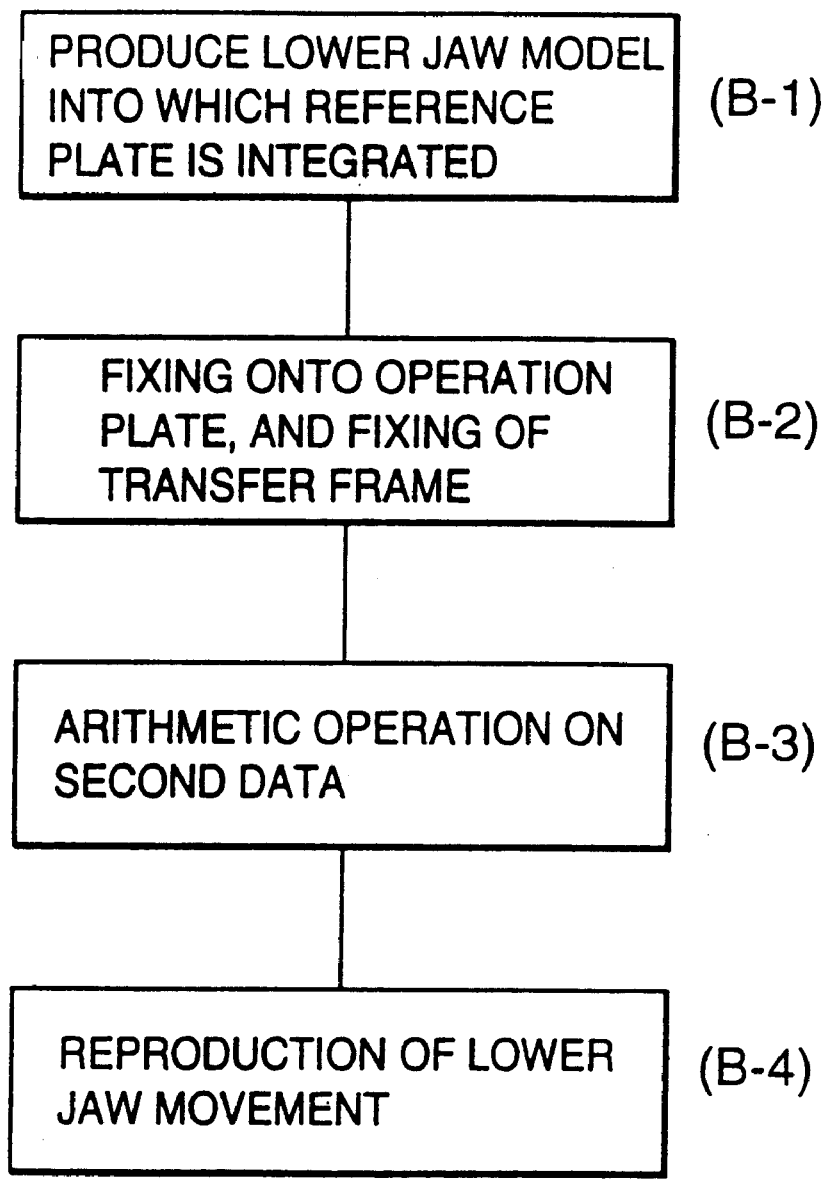
FIG. 18 is a flowchart useful for understanding a method of determining an exact located position of a lower jaw model onto an operating plate when the transfer frame is used.

FIG. 18 is a flowchart useful for understanding a method of determining an exact arrangement position of the lower jaw model 310 onto the operating plate 40 (cf. FIG. 11) when the transfer frame is used.

In order to arrange the lower jaw model 310 patterned after the lower jaw of a test subject onto the operating plate 40, first, the lower jaw model 310, onto which the reference plate 311 as positioning means for the operating plate 40 is fixed in a unitary body, is produced (step B-1). The reference plate 311, which is fixed onto the lower jaw model 310 in a unitary body, is engaged with holes or apertures (not illustrated) of the operating plate 40, which holes are formed to be engaged with pines 311D and 311E provided on the reference plate 311, and the lower jaw model 310 is fixed on the operating plate 40, and in addition the transfer frame 518 (cf. FIG. 16) is fixed on the lower jaw model 310 in such a manner that the position and the posture with respect to the lower jaw model 310 are the same as those with respect to a lower jaw of the test subject when the transfer frame 518 is fixed on the lower jaw of the test subject (step B.-2).

In this condition, the lower jaw model 310 is photographed by a plurality of cameras, for example, two cameras 12 and 14 shown in FIG. 3 from mutually different directions. This makes it possible that the lower jaw model fixed position arithmetic means 222 of the jaw movement reproducing control unit 22 determines the second data representative of the relative position and posture between the lower jaw model 310 and the reference plate 311 fixed onto the lower jaw model 310 in a unitary body (step B-3). The reference plate 311 is unequivocally determined in a positional relation with the operating plate 40 by two pins 311D and 311E. Consequently, the second data is representative of the position and posture of the lower jaw model 310 to the operating plate 40.

In a similar fashion to that of the explanation as to FIG. 14, when the reference plate shown in FIGS. 13(A) and (B) is adopted, the pointer pen 19 is prepared and the reference point marks 311A, 311B and 311C are touched with the tip 19a of the pointer pen 19. In this manner, the lower jaw model fixed position arithmetic means 222 (cf. FIG. 11) recognizes the positions of the reference point marks 311A, 311B and 311C through recognition of the LEDs 19A and 19B of the pointer pen 19. Alternatively, when the reference plate shown in FIGS. 15(A) and (B) is adopted, the lower jaw model fixed position arithmetic means 222 recognizes the positions of the LEDs 311F, 311G and 311H of provided on the reference plate, without using the pointer pen 19.

Thus, after determining the second data, the lower jaw control means 221 of the jaw movement reproducing control unit 22 shown in FIG. 11 controls six servo motors 35 of the jaw movement reproducing unit 30 in accordance with both the first data determined by the jaw movement arithmetic unit 21 and the second data determined by the lower jaw model fixed position arithmetic means 222 of the jaw movement reproducing control unit 22 (step B-4).

In this manner, the use of the transfer frame 518 makes it possible to mount the transfer frame 518 on the lower jaw model 310 with great accuracy, and thereby exactly reproducing a movement of the lower jaw.

Next, there will be explained an alternative method of fixing the lower jaw model on the operating plate in the event that the transfer frame is adopted.

Figure 19:
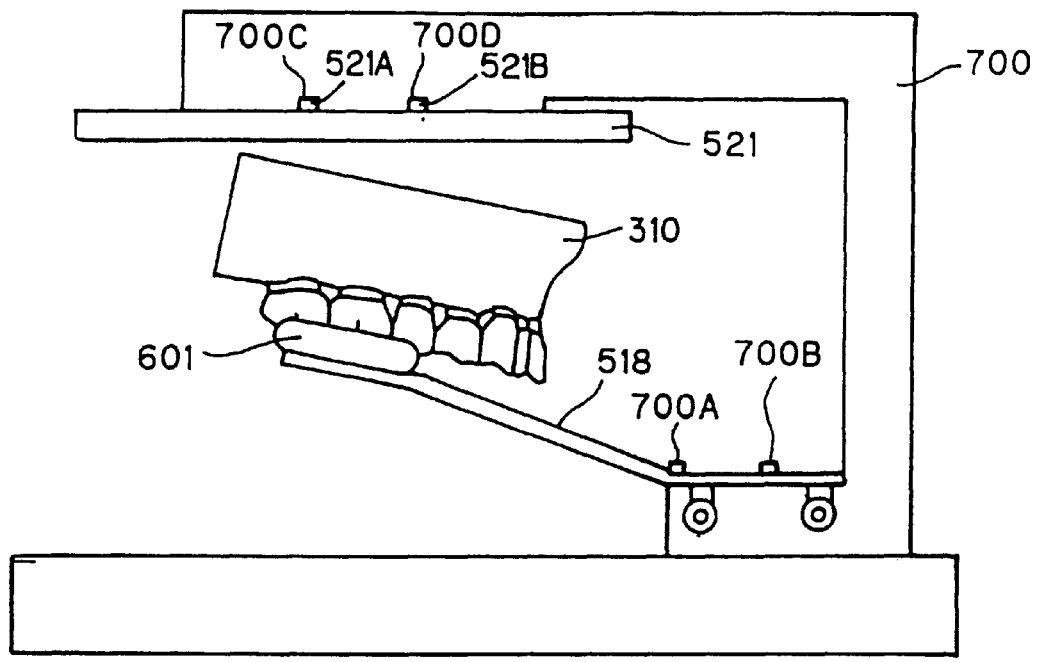
FIG. 19 is an explanatory view useful for understanding a method of fixing a lower jaw model using a transfer jig.
Figure 20:
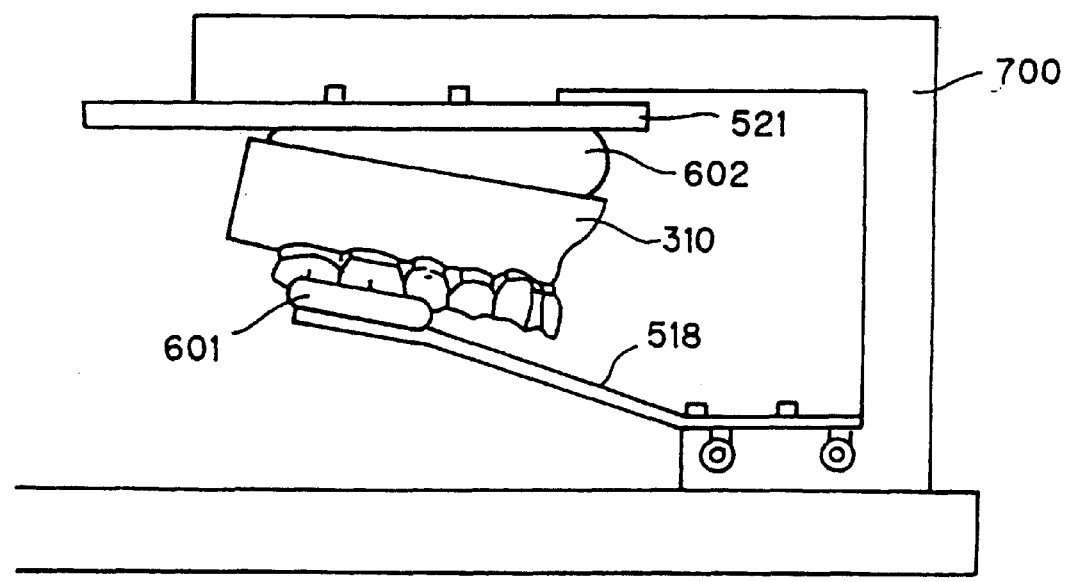
FIG. 20 is an explanatory view useful for understanding a method of fixing a lower jaw model using a transfer jig.
Figure 21:
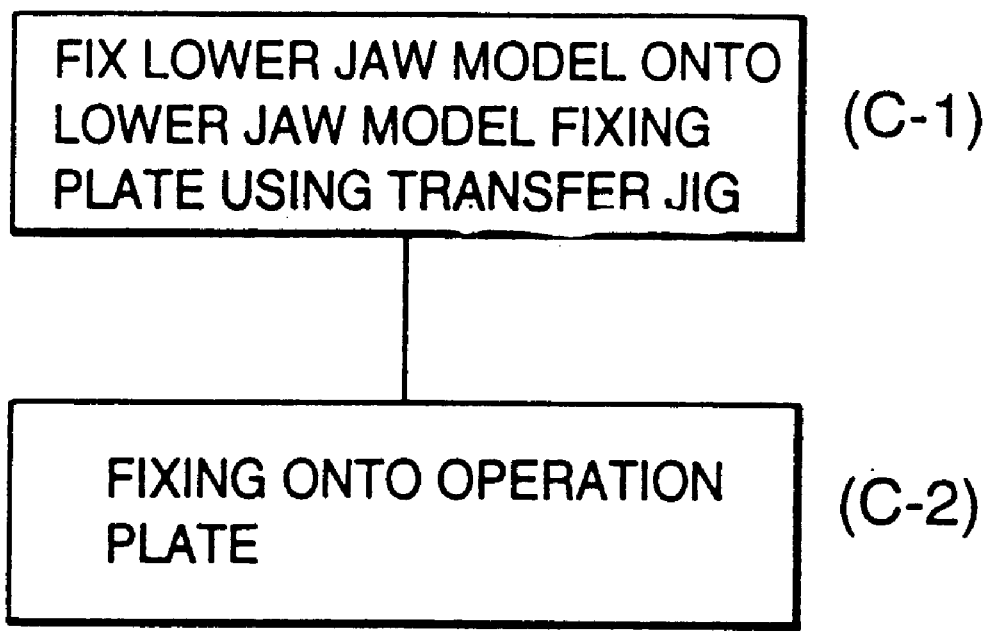
FIG. 21 is a flowchart useful for understanding a method of fixing a lower jaw model when a transfer jig is used.

Each of FIGS. 19 and 20 is an explanatory view useful for understanding a method of fixing a lower jaw model using a transfer jig. FIG. 21 is a flowchart useful for understanding a method of fixing a lower jaw model when a transfer jig is used.

A transfer jig 700 has two positioning pins 700A and 700B, which are inserted into two positioning holes 518D and 518E (cf. FIG. 17) provided on the transfer frame 518, respectively. The transfer frame 518 is fixed on the transfer jig 700 in such a state that the positioning holes 518D and 518E are engaged with the positioning pins 700A and 700B, respectively.

The lower jaw model 310 is fixed through an impression material 601 on the transfer frame 518 which is fixed on the transfer jig 700. At that time, the lower jaw model 310 is fixed on the transfer frame 518 in such a manner that the position and the posture of the transfer frame 518 with respect to the lower jaw model 310 are the same as those with respect to a lower jaw of the test subject when the transfer frame 518 is fixed on the lower jaw of the test subject (cf. FIG. 16). There is no need to fix the reference plate 311, as shown in FIGS. 13(A) and (B) and FIGS. 15(A) and (B), on the lower jaw model 310.

A lower jaw fixing plate 521 is fixed on the transfer jig 700 as shown in FIG. 19. The lower jaw model 310 is fixed on the lower jaw fixing plate 521 in the way which will be described hereinafter. The lower jaw fixing plate 521 has two positioning pins 521A and 521B, while the transfer jig 700 has two positioning holes 700C and 700D with which the positioning pins 521A and 521B are engaged, respectively. The lower jaw fixing plate 521 is fixed on the transfer jig 700 in such a state that the positioning pins 521A and 521B are engaged with the positioning holes 700C and 700D, respectively.

At that time, the relative positional relation between the transfer frame 518 and the lower jaw fixing plate 521 is unequivocally determined.

In step C-1 shown in FIG. 21, the state as shown in FIG. 19 is produced, and thereafter the space between the lower jaw model 310 and the lower jaw fixing plate 521 is filled up with for example, an impression material 602, so that the lower jaw model 310 is fixed on the lower jaw fixing plate 521.

The operating plate 40 of the jaw movement reproducing unit 30 has two positioning holes (not illustrated), as explained in conjunction with the pins 311D and 311E of the reference plate 311 shown in FIG. 13. The positioning pins 521A and 521B of the lower jaw fixing plate 521 may be engaged also with the positioning holes of the operating plate 40. As shown in FIG. 20, the lower jaw model 310 is fixed on the lower jaw fixing plate 521, thereafter removed from the transfer jig 700, and fixed on the operating plate 40 in such a state that the positioning pins 521A and 521B are engaged with the positioning holes of the operating plate 40, respectively (step C-2 in FIG. 21).

According to the respective embodiments explained above, after the lower jaw model 310 is fixed on the operating plate 40, the camera photography is again conducted, so that the position and the posture of the lower jaw model 310 on the operating plate 40 are determined. However, according to the present embodiment, the transfer frame 518 and the transfer jig 700 are used, so that the lower jaw model 310 is fixed on the operating plate 40 in a state that the position and the posture with respect to the operating plate 40 are controlled. This needs no camera photography for the second time, and thus reduces the corresponding errors. Thus, it is possible to reproduce a movement of the lower jaw with greater accuracy.

Hereinafter, the reason why the movement of the lower jaw can be reproduced in accordance with above-mentioned scheme will be explained on a logical basis.

[Calculation of angles of rotation of coordinates on a plane, which is determined by three points, with respect to the reference coordinate system]

Figure 22:
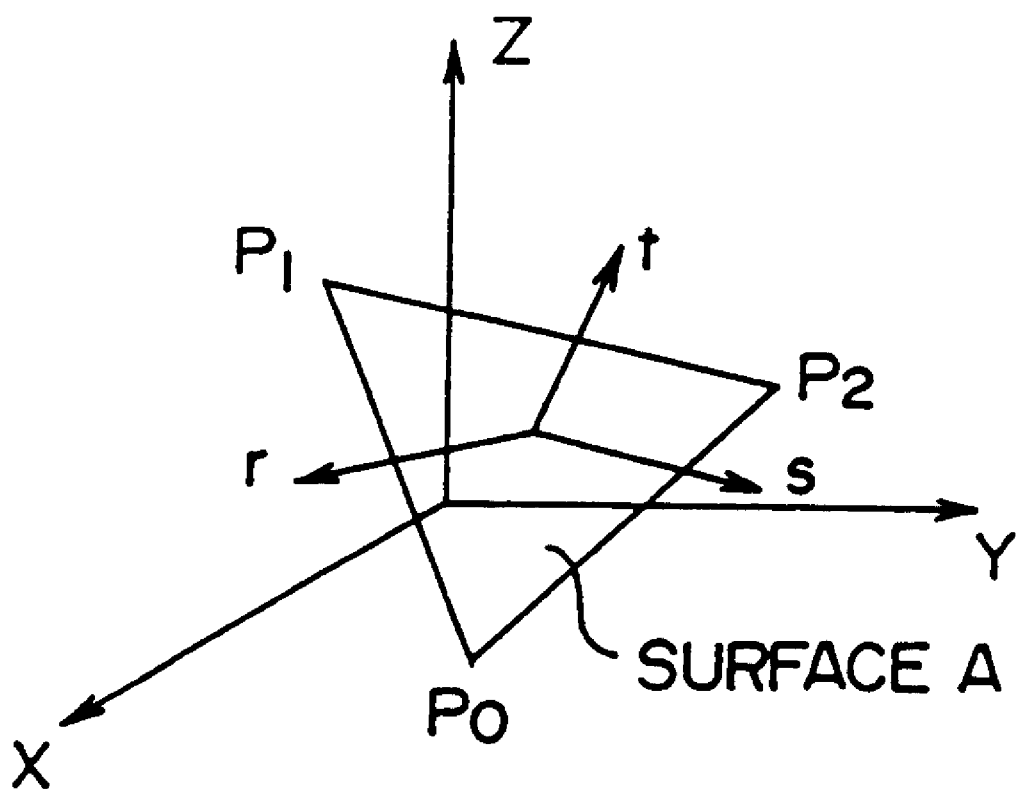
FIG. 22 is a view showing a reference coordinate system (XYZ) fixed on a substrate and a coordinate system (rst) fixed on an operating plate.
Figure 23:
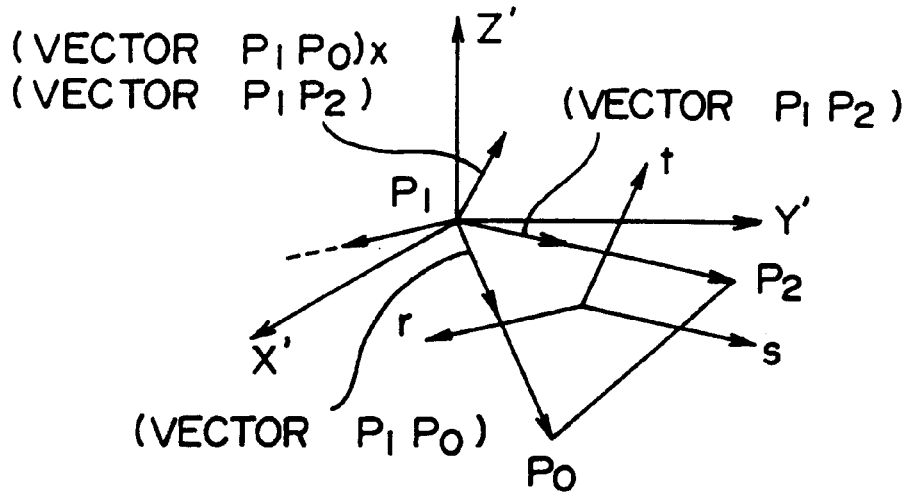
FIG. 23 is a view showing a coordinate system (X'Y'Z') in which coordinate axes X',Y',Z' are parallel to coordinate axes X, Y, Z of the coordinate system (XYZ), respectively and the origin is coincident with the point P1, and a coordinate system (rst) fixed on an operating plate.

FIG. 22 is a view showing a reference coordinate system (XYZ) fixed on a substrate 31 and a coordinate system (rst) fixed on an operating plate 40. FIG. 23 is a view showing a coordinate system (X'Y'Z') in which coordinate axes X',Y',Z' are parallel to coordinate axes X, Y, Z of the coordinate system (XYZ), respectively and the origin is coincident with the point Pl, and a coordinate system (rst) fixed on an operating plate 40.

Let us consider three points $P_0(x_0, y_0, z_0)$, $P_1(x_1, y_1, z_1)$, and $P_2(x_2, y_2, z_2)$ in an X Y Z coordinates. Also let us consider an r s t coordinate system having two axes on a surface A defined by the three points $P_0$, $P_1$, and $P_2$, in which the normal line of the surface A is given in the form of t-axis. It is assumed that s -axis is the same as (vector $P_1P_2$) in the direction. Here, put (vector $P_1P_2$)=(vector $P_s$).

Now determine an angle α of rotation on an X axis, an angle β of rotation on a Y axis, and an angle γ of rotation on a Z axis in such a manner that the respective associated axes take the same direction between the r s t coordinates and the X Y Z coordinates. It is possible to simply determine differences of position in X , Y , Z directions in the form of deviations between the origin of the X Y Z coordinate system and the origin of the r s-t coordinate system.

and (vector $p_t$), and components of the respective vectors in the X Y Z coordinate system are expressed by (vector $p_r$)=$(x_r, y_r, z_r)$ (vector $p_s$)=$(x_s, y_s, z_s)$ (vector $p_t$)=$(x_t, y_t, z_t)$ In the consideration of (vector p), it is assumed that the component for the X Y Z coordinate system is (x, y, z ), and the component for the r s t coordinate system is (x', y', z'). When the X Y Z coordinates are subjected to the α, β, γ rotations on the X axis the Y axis and the Z axis in the named order, if the X axis, the Y axis and the Z axis become the same as the r axis, the s axis, and the t axis in the direction, respectively, the following relation exists.

$$\begin{pmatrix} x' \\ y' \\ z' \end{pmatrix} = \underbrace{\begin{pmatrix} \cos\beta \cos\gamma & \cos\beta \sin\gamma & -\sin\beta \\ \sin\alpha \sin\beta \cos\gamma - \cos\alpha \sin\gamma & \sin\alpha \sin\beta \sin\gamma + \cos\alpha \cos\gamma & \sin\alpha \cos\beta \\ \cos\alpha \sin\beta \cos\gamma + \sin\alpha \sin\gamma & \cos\alpha \sin\beta \sin\gamma + \sin\alpha \cos\gamma & \cos\alpha \cos\beta \end{pmatrix}}_{[A]} \begin{pmatrix} x \\ y \\ z \end{pmatrix} \quad (41)$$

$$\begin{pmatrix} x \\ y \\ z \end{pmatrix} = \underbrace{\begin{pmatrix} \cos\beta \cos\gamma & \sin\alpha \sin\beta \cos\gamma - \cos\alpha \sin\gamma & \cos\alpha \sin\beta \cos\gamma + \sin\alpha \sin\gamma \\ \cos\beta \sin\gamma & \sin\alpha \sin\beta \sin\gamma + \cos\alpha \cos\gamma & \cos\alpha \sin\beta \sin\gamma - \sin\alpha \cos\gamma \\ -\sin\beta & \sin\alpha \cos\beta & \cos\alpha \cos\beta \end{pmatrix}}_{[A]^t} \begin{pmatrix} x' \\ y' \\ z' \end{pmatrix} \quad (42)$$

$[A]^t$ is a transposed matrix of $[A]$.

Now let us consider two vectors (vector $P_1$, $P_2$) and (vector $P_1P_0$) where point $P_1$ is a start point.

When an outer product (vector $P_1P_0$)×(vector$P_1P_2$) of (vector$P_1P_0$) and (vector $P_1P_2$) is considered, this vector becomes a normal line of the surface A, and its direction is the same as the t-axis. This vector is expressed as follows.

(vector $P_t$)=$(P_{tx}, P_{ty}, P_{tz})$

Next, an outer product of (vector $P_1P_2$) and (vector $P_t$) becomes the same as r-axis in the direction. This vector is expressed as follows.

(vector $P_1P_2$)×(vector $P_t$)=(vector $P_r$)

Thus, (vector $P_r$), (vector $P_s$) and (vector $P_t$) become the same vectors as the positive sides of the coordinate axes r, s and t in the direction, respectively.

Next, those three vectors are divided by their associated absolute values, respectively into unit vectors in the r s t coordinate system.

The unit vectors to the respective axes in the r s t coordinate system are expressed by (vector $p_r$) (vector $p_s$)

In the event that (vector $p_r$), (vector $p_s$) and (vector $p_t$) are the r s t coordinate system in which the X Y Z coordinates are subjected to the α, β, γ rotations on the X axis, the Y axis and the Z axis in the named order, since they are the unit vector, from the equation (41), the following expressions are obtained.

$$\begin{pmatrix} 1 \\ 0 \\ 0 \end{pmatrix} = [A] \begin{pmatrix} x_r \\ y_r \\ z_r \end{pmatrix}$$

$$\begin{pmatrix} 0 \\ 1 \\ 0 \end{pmatrix} = [A] \begin{pmatrix} x_s \\ y_s \\ z_s \end{pmatrix}$$

$$\begin{pmatrix} 0 \\ 0 \\ 1 \end{pmatrix} = [A] \begin{pmatrix} x_t \\ y_t \\ z_t \end{pmatrix}$$

Therefore, from the equation (42), the following expressions are obtained.

$$\begin{pmatrix} x_r \\ y_r \\ z_r \end{pmatrix}_t = [A] \begin{pmatrix} 1 \\ 0 \\ 0 \end{pmatrix} = \begin{pmatrix} \cos\beta\cos\gamma & \sin\alpha\sin\beta\cos\gamma - \cos\alpha\sin\gamma & \cos\alpha\sin\beta\cos\gamma + \sin\alpha\sin\gamma \\ \cos\beta\sin\gamma & \sin\alpha\sin\beta\sin\gamma + \cos\alpha\cos\gamma & \cos\alpha\sin\beta\sin\gamma - \sin\alpha\cos\gamma \\ -\sin\beta & \sin\alpha\cos\beta & \cos\alpha\cos\beta \end{pmatrix} \begin{pmatrix} 1 \\ 0 \\ 0 \end{pmatrix} \quad (43)$$

$$\begin{pmatrix} x_s \\ y_s \\ z_s \end{pmatrix}_t = [A] \begin{pmatrix} 0 \\ 1 \\ 0 \end{pmatrix} = \begin{pmatrix} \cos\beta\cos\gamma & \sin\alpha\sin\beta\cos\gamma - \cos\alpha\sin\gamma & \cos\alpha\sin\beta\cos\gamma + \sin\alpha\sin\gamma \\ \cos\beta\sin\gamma & \sin\alpha\sin\beta\sin\gamma + \cos\alpha\cos\gamma & \cos\alpha\sin\beta\sin\gamma - \sin\alpha\cos\gamma \\ -\sin\beta & \sin\alpha\cos\beta & \cos\alpha\cos\beta \end{pmatrix} \begin{pmatrix} 0 \\ 1 \\ 0 \end{pmatrix} \quad (44)$$

$$\begin{pmatrix} x_t \\ y_t \\ z_t \end{pmatrix}_t = [A] \begin{pmatrix} 0 \\ 0 \\ 1 \end{pmatrix} = \begin{pmatrix} \cos\beta\cos\gamma & \sin\alpha\sin\beta\cos\gamma - \cos\alpha\sin\gamma & \cos\alpha\sin\beta\cos\gamma + \sin\alpha\sin\gamma \\ \cos\beta\sin\gamma & \sin\alpha\sin\beta\sin\gamma + \cos\alpha\cos\gamma & \cos\alpha\sin\beta\sin\gamma - \sin\alpha\cos\gamma \\ -\sin\beta & \sin\alpha\cos\beta & \cos\alpha\cos\beta \end{pmatrix} \begin{pmatrix} 0 \\ 0 \\ 1 \end{pmatrix} \quad (45)$$

Here, in the condition of $-(\pi/2) \leq \alpha \leq (\pi/2)$, $-(\pi/2) \leq \beta \leq (\pi/2)$, $-(\pi/2) \leq \gamma \leq (\pi/2)$, from the equations (43)~(45), $\alpha$, $\beta$, $\gamma$ are determined.

$$\beta = \sin^{-1}(-Z_r)$$
$$\gamma = \sin^{-1}\left(\frac{y_r}{\sqrt{1-z_r^2}}\right)$$
$$\alpha = \sin^{-1}\left(\frac{z_s}{\sqrt{1-z_r^2}}\right)$$

In this manner, looking toward the coordinate system (r s t) fixed on the operating plate 40 (the coordinate system (r s t) is equivalent to the coordinate system of the lower jaw model 310 fixed on the operating plate 40 since the coordinate system (r s t) is determined on the basis of the reference points $P_1$, $P_2$, $P_3$) at the reference coordinate system (X Y Z) fixed on the substrate 31 (that is, the reference coordinate system (X Y Z) is equivalent to the coordinate system of the upper jaw model 210 since the upper jaw model 210 is fixed on the substrate 31 through the ceiling board 53 and the poles 32), the position and the attitude of the coordinate system (r s t) is determined.

The lower jaw model fixed position arithmetic means 222 of the jaw movement reproducing control unit 22 shown in FIG. 11 determines the initial state of the lower jaw model 310 on the basis of the above-mentioned theory. The lower jaw control means 221 controls the position and the attitude of the lower jaw model 310 on the basis of the initial state thus determined.

The control of the position and the attitude of the lower jaw model 310 by the lower jaw control means 221 is performed directly through controlling the angles of rotation of the rotating shafts 35a of 6 servo motors 35. Accordingly, there is a need to determine a relationship between an angle of rotation of the rotating shaft 35a of each of the servo motors 35 and the position or the attitude of the lower jaw model 310 on the operating plate 40. This relationship can be determined in the form of an intersection of a sphere of which the center point is defined by a mounting position (rotational center of the ball joint 39) of the link 38 mounted on the operating plate 40 onto the operating plate 40, the radius of the sphere being defined by the length (a distance between the rotational center of the ball joint 37 and the rotational center of the ball joint 39) of the link 38, and a circle of which the center is defined by the rotational center of the rotating shaft 35a of the servo motor 35 on the disk horn 36, the radius of the circle being defined by a distance between the rotational center of the rotating shaft 35a and the mounting position (rotational center of the ball joint 37) of the link 38 mounted on the horn 36. That is, according to the coordinate system fixed on the lower jaw model 310, any movement of the lower jaw model 310 in its position or its attitude involves no variation in the coordinate related to the rotational center of the ball joint 39, and thus in the event that the lower jaw model 310 is moved to a desired position and attitude, the coordinate related to the rotational center of the respective ball joint 39 can be expressed by the reference coordinate system (XYZ). Here, it will be described typically one link 38. There is determined a coordinate of an intersection of a sphere of which the center is defined by a rotational center of the ball joint 39 coupling the link 38 to the operating plate 40, the radius of the sphere being defined by the length of the link 38, and a circle of which the center is defined by the rotational center of the rotating shaft 35a of the servo motor 35 on the horn 36 associated link 38, the radius of the circle being defined by a distance between the rotational center of the rotating shaft 35a and the rotational center of the ball joint 37. The coordinate of the intersection thus determined is replaced by an angle of rotation of the rotating shaft 35a of the servo motor 35. The servo motor 35 is controlled in such a manner that the rotating shaft 35a of the servo motor 35 offers the angle of rotation concerned. Such a control is practiced to all six servo motors 35. Thus, it is possible to arrange the lower jaw model 310 at a desired position and in a desired attitude.

Hereinafter, it will be described theoretically as to how to determine the intersection of the sphere and the circle mentioned above.

[Calculation of the intersection of a sphere and a circle]

Figure 24:
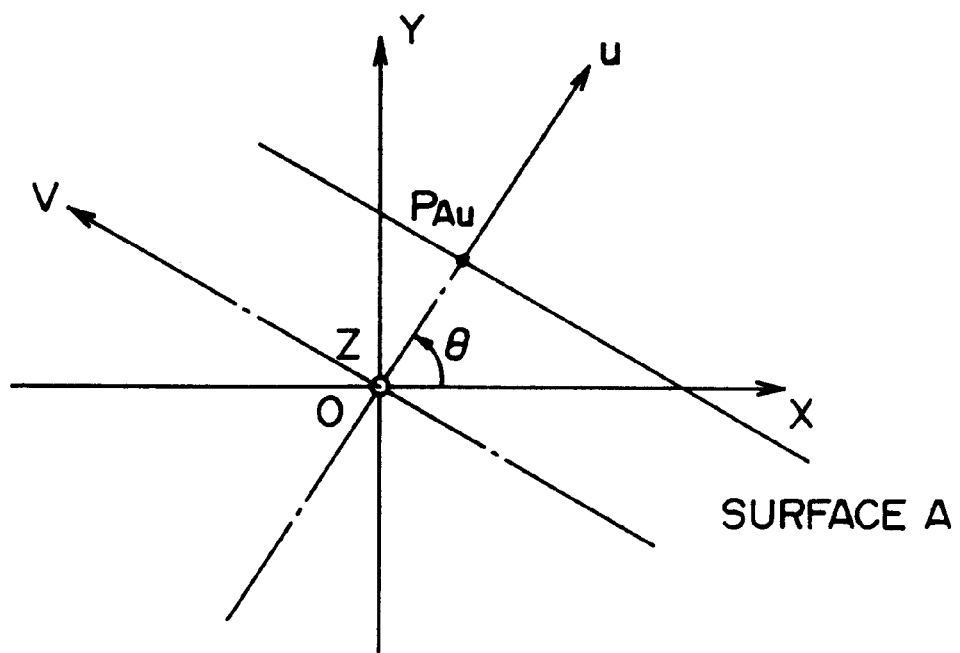
FIG. 24 is a view showing an XYZ coordinate system and a uvz coordinate system which is equivalent to one in which the XYZ coordinate system is rotated on the coordinate axis Z by angle θ.

FIG. 24 is a view showing an XYZ coordinate system and a uvz coordinate system which is equivalent to one in which the XYZ coordinate system is rotated on the coordinate axis Z by angle θ.

Now let us consider a center coordinate $(x_0, y_0, z_0)$ in the XYZ coordinate system, a sphere B having the radius, and a new uvz coordinate system in which the normal line is parallel to the Z axis, and the X axis is coincident with the normal line of the surface A.

When the coordinate of the center $P_0$ of the sphere B in the u v z coordinate system is expressed by $(u_0, v_0, z_0')$, the following equation exist.

$$\begin{pmatrix} u_0 \\ v_0 \\ z_0' \end{pmatrix} = \begin{pmatrix} \cos\theta & \sin\theta & 0 \\ -\sin\theta & \cos\theta & 0 \\ 0 & 0 & 1 \end{pmatrix} \begin{pmatrix} x_0 \\ y_0 \\ z_0 \end{pmatrix} \quad (46)$$

Hereinafter, it is considered in the u v z coordinate system. The intersection $P_{Au}$ of the surface A and the u axis is expressed by $(u_a, 0, 0)$. Then the point group of the intersection of the sphere B and the surface A becomes a circle, and the expression of the circle $C_A$ is given by the following equation.

$$(u-u_0)^2 + (v-v_0)^2 + (z-z_0)^2 = R^2$$

u=$u_a$. Therefore, $$(v-v_0)^2+(z_{-z0})^2=R^2-(u_a-u^0)^2$$

If $u_a-u_0=\epsilon$, $$(v-v_0)^2+(z-z_0)^2=R^2\epsilon^2 \qquad (47)$$

Now considering a circle $C_h$ of the radius r in $P_h$ ($v_h$, $z_h$) on the surface A, then the expression of the circle $C_h$ is given by the following equation.

$$(v-v_h)^2+(z-z_h)^2=r^2 \qquad (48)$$

The intersection of the circles $C_A$ and $C_h$ can be determined by solving the simultaneous equations of the equations (47) and (48).

The solutions are as follows.

$$z=\frac{-\gamma\pm\sqrt{\gamma^2-4\beta\delta}}{2\beta}$$

$$v=\frac{\alpha}{2(v_h-v_0)}-\frac{z_h-z_0}{v_h-v_0}\left(\frac{-\gamma\pm\sqrt{\gamma^2-4\beta\delta}}{2\beta}\right)$$

$\gamma^2\geq 4\beta\delta$ (determinant)

$$\alpha=R^2-\epsilon^2-r^2-v_0^2+v_h^2-z_0^2+z_h^2$$

$$\beta=\left(\frac{z_h-z_0}{v_h-v_0}\right)^2+1$$

$$\gamma=\frac{2v_h(z_h-z_0)}{v_h-v_0}-\frac{\alpha(z_h-z_0)}{(v_h-v_0)^2}-2z_h$$

$$\delta=\left\{\frac{\alpha}{2(v_h-v_0)}\right\}^2-\frac{v_h\alpha}{v_h-v_0}+v_h^2+z_h^2-r^2$$

$\epsilon=u_a-u_0$

Here, when the center coordinate of the circle $C_h$ is $P_h(v_h, 0)$, the coordinate of the intersection $z_h=0$. Therefore, $$z=\frac{-\gamma\pm\sqrt{\gamma^2-4\beta\delta}}{2\beta}$$

$$v=\frac{\alpha}{2(v_h-v_0)}+\frac{z_0}{v_h-v_0}\left(\frac{-\gamma\pm\sqrt{\gamma^2-4\beta\delta}}{2\beta}\right)$$

$\gamma^2\geq 4\beta\delta$ (determinant)

$$\alpha=R^2-\epsilon^2-r^2-v_0^2+v_h^2-z_0^2$$

$$\beta=\left(\frac{z_0}{v_h-v_0}\right)^2+1$$

$$\gamma=-\frac{2v_h z_0}{v_h-v_0}+\frac{\alpha z_0}{(v_h-v_0)^2}$$

$$\delta=\left\{\frac{\alpha}{2(v_h-v_0)}\right\}^2-\frac{v_h\alpha}{v_h-v_0}+v_h^2-r^2$$

$\epsilon=u_a-u_0$

The 6 ball joints 39, which couple the 6 links 38 on the operating plate 40, are arranged in a pair of two ball joints 39 at the positions such that the respective pairs are rotated in the angle by 120°. The above-mentioned angle 6 is (cf. FIG. 24) is set up to the angle corresponding to the associated arrangement position of the respective ball joints 39, so that the angles of rotation of the rotating shaft 35a of the 6 servo motors 35 can be determined.

In this manner, the 6 servo motors 35 is controlled, and thus it is possible to move the lower jaw model 310 fixed on the operating plate 40 to a desired position and attitude.

Figure 25:
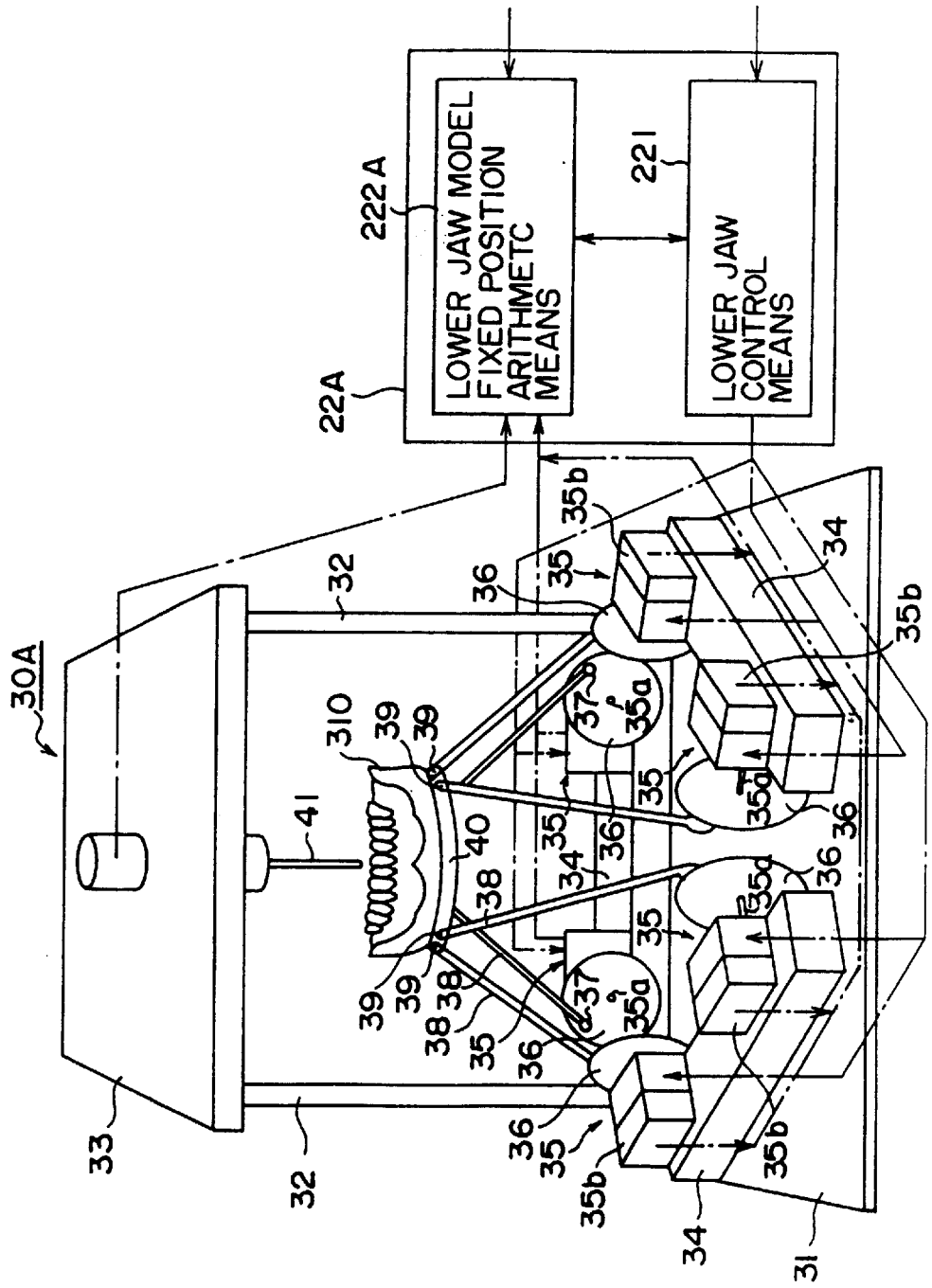
FIG. 25 is a typical illustration useful for understanding a second embodiment of a jaw movement simulator according to the present invention.
Figure 26:
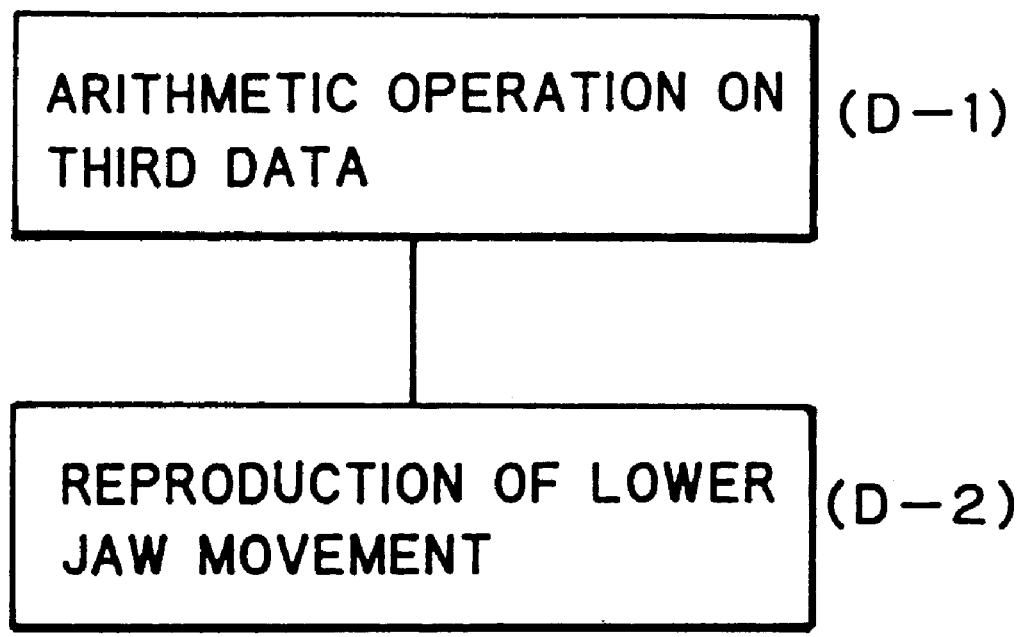
FIG. 26 is a flowchart useful for understanding a jaw movement simulation method when using the jaw movement simulator shown in FIG. 25.

FIG. 25 is a typical illustration useful for understanding a second embodiment of a jaw movement simulator according to the present invention. There will be described only a difference between it and the first embodiment shown in FIG. 11. FIG. 26 is a flowchart useful for understanding a jaw movement simulation method when using the jaw movement simulator shown in FIG. 25.

The jaw movement simulator shown in FIG. 25 comprises a jaw movement reproducing unit 30A and a jaw movement reproducing control unit 22A. The jaw movement reproducing unit 30A is provided with a contact detection probe 41 detachably mounted on the ceiling board 33 for detecting that the lower jaw model 310 contacts with the contact detection probe 41. While the jaw movement reproducing unit 30A fails to show the upper jaw model 210 (FIG. 11), the upper jaw model 210 is to be fixed on the ceiling board 33 after the contact detection probe 41 is removed from the ceiling board 33. It is to be noted that omission of the upper jaw model 210 in FIG. 25 does not mean a difference from the first embodiment shown in FIG. 11.

The jaw movement reproducing control unit 22A shown in FIG. 25 receives a contact detection signal from the contact detection probe 41 and angle detection signals of the angle detectors 35b each for detecting an angle of rotation of the associated rotating shaft 35a of the 6 servo motors 35. A lower jaw model fixed position arithmetic means 222A of the jaw movement reproducing control unit 22A determines the coordinates of the lower jaw model 310 to the reference coordinate system fixed on the substrate 31, taking account of the arrangement positional deviation of the lower jaw model 310 on the operating plate 40.

That is, the second embodiment shown in FIG. 25 adopts a method of identification different from various types of method of identification for the arrangement position of the lower jaw model 310 on the operating plate 40, which have been explained referring to the first embodiment shown in FIG. 11.

In case of the second embodiment shown in FIG. 25, there is no need to fix the reference plate 311 (cf. FIG. 13(B)) on the lower jaw model 310, instead, when an imaging of the jaw movement is conducted (cf. FIG. 3), in the state that the subject 1 opens his mouth, the tip 19a of the pointer pen 19 shown in FIG. 4 is put to three teeth of the lower teeth, which are mutually separated, so that the positions of those three teeth are designated as the extended points of the LEDs 19A and 19B.

The positional information of those three teeth is fed to the lower jaw model fixed position arithmetic means 222A of the jaw movement reproducing control unit 22A.

In the jaw movement simulator shown in FIG. 25, the lower jaw model 310 is fixed on the operating plate 40 of the jaw movement reproducing unit 30A, and the contact detection probe 41 is set up in such a manner that the same tooth as that indicated by the pointer pen 19 (FIG. 4) at the time of imaging (in case of the lower jaw model 310, such a tooth refers to a tooth on the model) is in contact with the tip of the contact detection probe 41, to read angles of rotation of the rotating shafts 35a detected by the angle detectors 35b of the respective servo motors 35. In order that a tooth of the lower jaw model 310 is in contact with the tip of the contact detection probe 41, in the state that the rotating shafts 35a of the 6 servo motors 35 are rotatable, the operating plate 40 is manually moved so that the noticed tooth of the lower jaw model 310 is contact with the tip of the contact detection probe 41.

The above-mentioned procedure is performed on each of the three teeth designated by the pointer pen 19 at the time of imaging. The lower jaw model fixed position arithmetic means 222A reads the angle detection signals of the 6 angle detectors 35b when each of the three teeth is in contact with the tip of the contact detection probe 41. Thus, the lower jaw model fixed position arithmetic means 222A determines on the basis of data thus collected a third data representative of the position and the attitude of the coordinate system fixed on the lower jaw model to the reference coordinate system fixed on the substrate 31 (step D-1 in Fig, 26). There will be described later an algorithm for identifying the coordinate system onto the lower jaw model on the basis of information obtained through reading the angle detection signals of the angle detectors 35b.

The lower jaw control means 221 of the jaw movement reproducing control unit 22A shown in FIG. 25 receives the third data determined by the lower jaw model fixed position arithmetic means 222A of the jaw movement reproducing control unit 22A, as well as the first data representative of a movement of the lower jaw with respect to the upper jaw of the test subject, which first data is determined by the jaw movement arithmetic unit 21, and controls six servo motors 35 of the jaw movement reproducing unit 30A on the basis of both the first data and the third data. Thus, also in the jaw movement simulator shown in FIG. 25, it is possible to reproduce a movement of the jaw with great accuracy.

Figure 27:
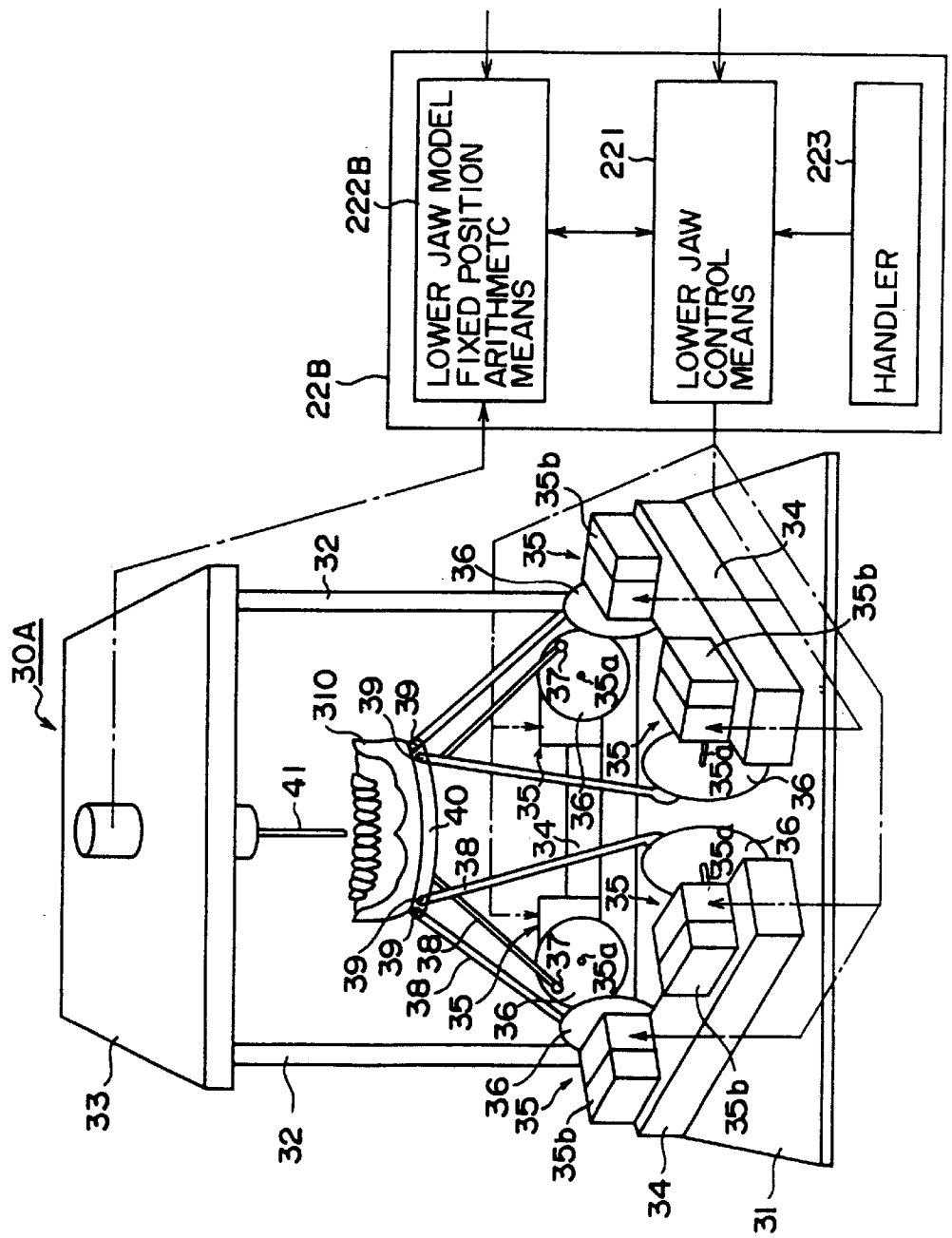
FIG. 27 is a typical illustration useful for understanding a third embodiment of a jaw movement simulator according to the present invention.

FIG. 27 is a typical illustration useful for understanding a third embodiment of a jaw movement simulator according to the present invention. There will be described only a difference between it and the second embodiment.

Of the jaw movement simulator shown in FIG. 27., the jaw movement reproducing unit 30A is the same in the structure as the jaw movement reproducing unit 30A shown in FIG. 25. But there is no need to provide a wiring for transmission of the angle detection signals of the angle detectors 35b of the respective servo motors 35 to the jaw movement reproducing control unit.

A jaw movement reproducing control unit 22B constituting the jaw movement simulator shown in FIG. 27 has a handler 223 for operating the lower jaw model 310 fixed on the operating plate 40. The handler 223 comprises, for example, the keyboard 23 shown in FIG. 3 and the like.

According to the second embodiment shown in FIG. 25, in the state that the rotating shafts 35a of the 6 servo motors 35 are rotatable, the operating plate 40 is manually moved. On the contrary, according to the third embodiment shown in FIG. 27, the handler 223 is operated to move the lower jaw model 310 on the operating plate 40, so that the teeth of interest on the lower jaw model 310 is in contact with the tip of the contact detection probe 41.

The lower jaw model fixed position arithmetic means 222B identifies, on the basis of operational information of the handler 223 without reading angles of rotation of the rotating shafts 35a detected by the angle detectors 35b of the servo motors 35, the the position and the attitude of the coordinate system fixed on the lower jaw model to the reference coordinate system fixed on the substrate 31.

Next, there will be explained an identification algorithm of the coordinate system of the lower jaw model in the case of the second embodiment shown in FIG. 25, that is, an algorithm for identifying the coordinate system of the lower jaw model on the basis of information obtained through reading the angle detection signals of the angle detectors 35b.

Figure 28:
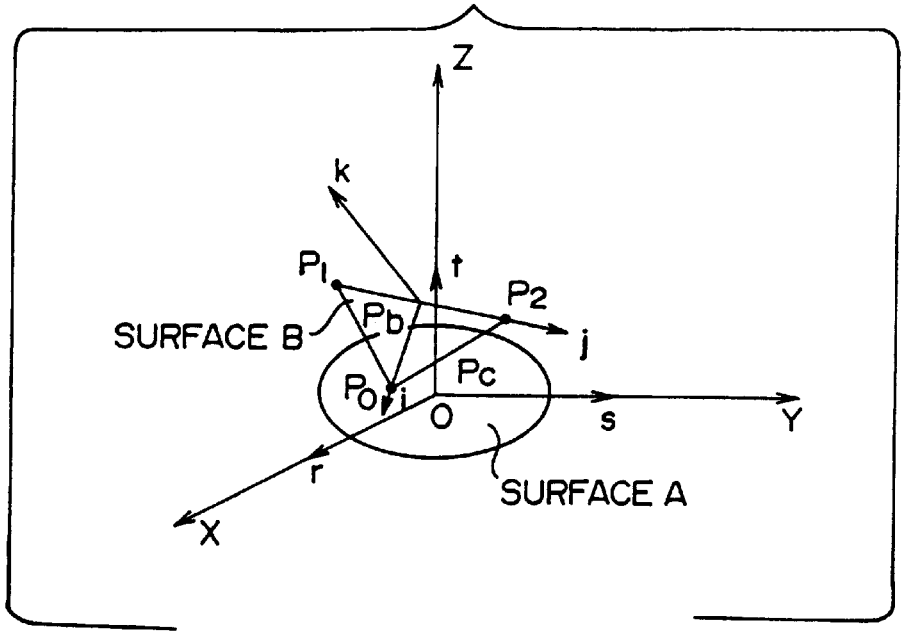
FIG. 28 is a view showing a reference coordinate system (XYZ) fixed on a substrate, a coordinate system (rst) fixed on an operating plate which is in the initial state, and a coordinate system (ijk) fixed on a lower jaw model fixed on the operating plate.
Figure 29:
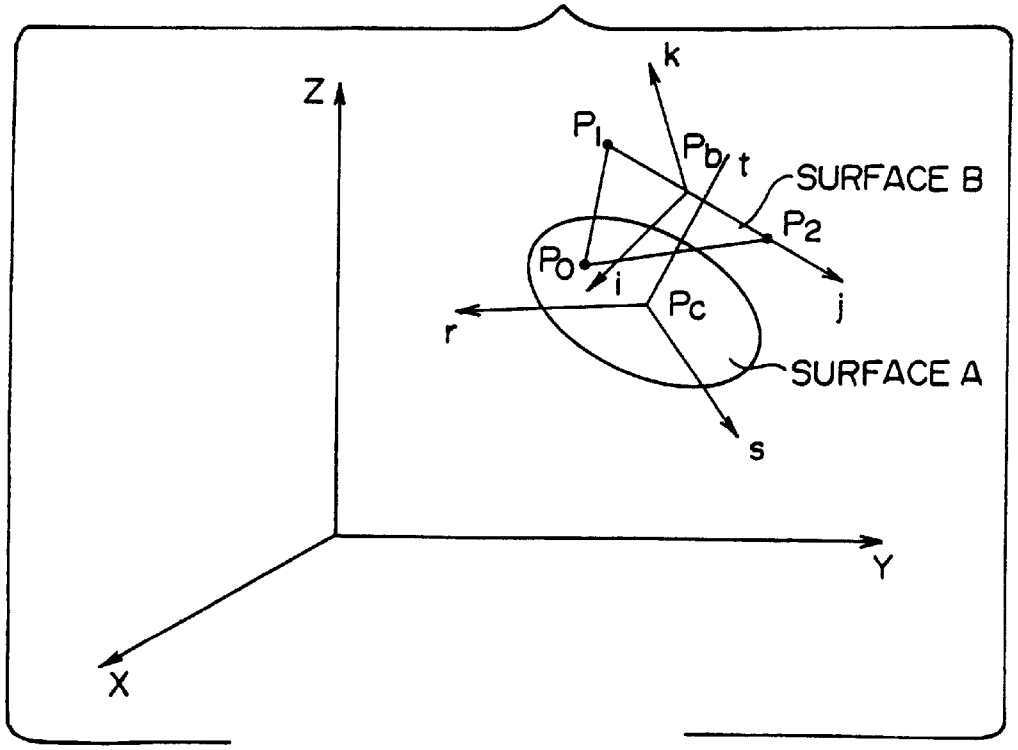
FIG. 29 is a view, which is similar to that of FIG. 28, showing a state in which the operating plate is moved from the initial state.
Figure 30:
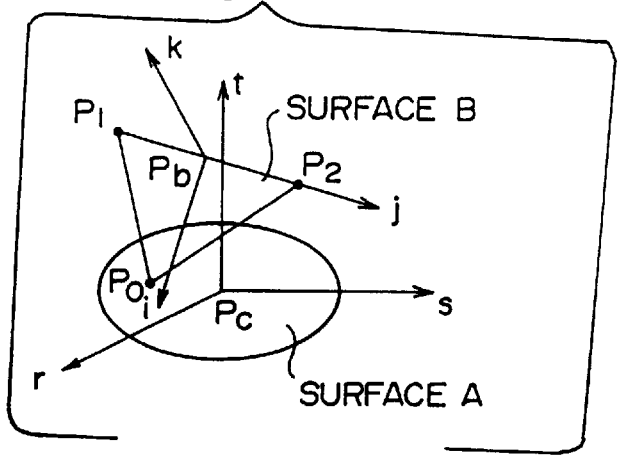
FIG. 30 is a view showing a coordinate system (rst) fixed on an operating plate and a coordinate system (ijk) fixed on a lower jaw model.
Figure 31:
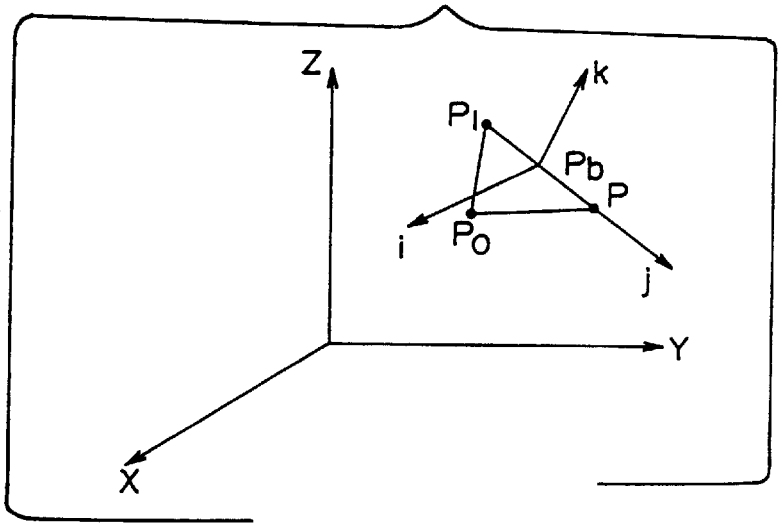
FIG. 31 is a view showing a reference coordinate system (XYZ) and a coordinate system (ijk) fixed on a lower jaw model.

FIG. 28 is a view showing a reference coordinate system (XYZ) fixed on the substrate 31, a coordinate system (rst) fixed on the operating plate 40 which is in the initial state, and a coordinate system (ijk) fixed on a lower jaw model 310 fixed on the operating plate 40. FIG. 29 is a view, which is similar to that of FIG. 28 , showing a state in which the operating plate 40 is moved from the initial state. FIG. 30 is a view showing a coordinate system (rst) fixed on the operating plate 40 and a coordinate system (ijk) fixed on the lower jaw model 310. FIG. 31 is a view showing a reference coordinate system (XYZ) and a coordinate system (ijk) fixed on the lower jaw model 310.

It is assumed that when the operating plate 40 is in the initial state (initial position and the initial attitude), the operating plate 40 is arranged to extend in parallel to the substrate 31. And also it is assumed that as shown in FIG. 28, the origin of the reference coordinate system (X Y Z) is matched with the origin of the coordinate system (r s t) on the operating plate 40, and an X axis, a Y axis and a Z axis of the reference coordinate system(X Y Z ) match in their direction with an r axis, an s axis, and a t axis of the coordinate system (r s t) on the operating plate 40, respectively. Here, three reference points $P_1$, $P_2$ and $P_3$ are designated through applying the pointer pen 19 on the lower teeth of the subject 1 and the lower teeth of the lower jaw model 310 in the manner as mentioned above. It does not always happen that each of three axes of the coordinate system (r s t) fixed on the operating plate 40 is parallel to the associated one of three axes of the coordinate system (i j k) fixed on the lower jaw model 310. And thus those coordinate systems (r s t) and (i j k) are considered separately.

As shown in FIG. 30, there exist points $P_0$, $P_1$, and $P_2$ fixed on a surface A. The surface A implies the upper surface of the operating plate 40, and the points $P_0$, $P_1$ and $P_2$ stand for positions of three teeth on the lower jaw model 310, which are specified in the manner as mentioned above. Now let us consider the orthogonal coordinate system r s t coordinates where the central pointP, of the surface A is the origin, and the t axis is the normal line.

Further, let us consider the orthogonal coordinate system i j k coordinates where the middle point $P_b$ of the segments $P_1$, $P_2$ is the origin, the k axis is the normal line of the surface B formed by the points $P_0$, $P_1$, and $P_2$, and (vector $P_bP_2$) is the j axis.

It is assumed that the coordinate values of the points $P_0$, $P_1$, $P_2$ in the r s t coordinate system are given by $P_0(r_0, s_0, t_0)$ $P_1(r_1, s_1, t_1)$ $P_2(r_2, s_2, t_2)$ As the initial state, as shown in FIG. 28, the origin 0 of the X Y Z coordinate system and the origin $P_c$ of the r s t coordinate system are coincident with each other, and the r axis, the s axis and the t axis are coincident with the x axis, the Y axis and the z axis, respectively.

It is assumed that from this state the point $P_c$ is moved by $\Delta x$, $\Delta y$, $\Delta z$, and with respect to the r, s, t axes, $\alpha$, $\beta$, $\gamma$ rotations are performed on the r axis, the s axis and the t axis, respectively, and as a result offering the state shown in FIG. 29.

Here, under the condition as mentioned above, when the points $P_0$, $P_1$, $P_2$ in the X Y Z coordinate system are given by $P_0(x_{0n}, y_{0n}, z_{0n})$ $P_1(x_{1n}, y_{1n}, z_{1n})$ $P_2(x_{2n}, y_{2n}, z_{2n})$ $\Delta x$, $\Delta y$, $\Delta z$, $\alpha$, $\beta$, $\gamma$ are determined.

[Determine a relationship between the r s t coordinates and the i j k coordinates]

Components of unit vectors (vector i ), (vector j and (vector k ) of the i j k coordinates on the r s t coordinate system are determined on the basis of the coordinate values on the points $P_0$, $P_1$ and $P_2$.

The coordinate of the origin $P_b$ of the i j k coordinate system is expressed by $$P_b = (r_b, s_b, t_b) \tag{49}$$

Then, the components of (vector $P_b P_2$) (vector $P_b P_0$) are as follows.

$$\begin{aligned}(\text{vector } P_b P_2)(r_2 - r_b, s_2 - s_b, t_2 - t_b) \\ = (vector\ P_j)(P_{jr}, P_{js}, P_{jt}) \\ (\text{vector } P_b P_0)(r_0 - r_b, s_0 - s_b, t_0 - t_b)\end{aligned}$$

When the (vector $P_k$), which is coincident with the k axis, is considered, a vector satisfying the condition is obtained from the following expression.

$$(\text{vector}P_k) = (\text{vector}P_b P_0) \times (\text{vector}P_b P_2) = (P_{kr}, P_{ks}, P_{kt}) \tag{50}$$

Next, when the (vector $P_1$), which is coincident with the i axis, is considered, a vector satisfying the condition is obtained from the following expression.

$$(\text{vector}P_i) = (\text{vector}P_b P_2) \times (\text{vector}P_k) = (P_{ir}, P_{is}, P_{it}) \tag{51}$$

From the above, the unit vectors (vector i), (vector j), (vector k) for i, i, k axes are obtained, and the associated respective components are expressed by $$\left.\begin{array}{l}(vector_i) = (r_i, s_i, t_i) \\ (vector_j) = (r_j, s_j, t_j) \\ (vector_k) = (r_k, s_k, t_k)\end{array}\right\} \tag{52}$$

Now let us determine a rotation of the i j k coordinates to the r s t coordinates. When the r s t coordinates are rotated by a, b and c for r, s and t axes, respectively, with respect to the r s and t axes in the named order, if the respective associated axes of the two coordinate systems are coincident with each other in their direction, then the following expressions may be given.

$$\begin{pmatrix}1\\0\\0\end{pmatrix} = A\begin{pmatrix}r_i\\s_i\\t_i\end{pmatrix}, \begin{pmatrix}0\\1\\0\end{pmatrix} = A\begin{pmatrix}r_j\\s_j\\t_j\end{pmatrix}, \begin{pmatrix}1\\0\\0\end{pmatrix} = A\begin{pmatrix}r_k\\s_k\\t_k\end{pmatrix}$$

$$A = \begin{pmatrix}\cos b\cos c & \cos b\sin c & -\sin b \\ \sin a\sin b\cos c - \cos a\sin c & \sin a\sin b\sin c + \cos a\cos c & \sin a\cos b \\ \cos a\sin b\cos c + \sin a\sin c & \cos a\sin b\sin c - \sin a\cos c & \cos a\cos b\end{pmatrix}$$

Since both the r s t coordinates and the i j k coordinates are orthogonal coordinates, the following relation exists.

$$\begin{pmatrix}r_i\\s_i\\t_i\end{pmatrix} = A^t\begin{pmatrix}1\\0\\0\end{pmatrix}, \begin{pmatrix}r_j\\s_j\\t_j\end{pmatrix} = A^t\begin{pmatrix}0\\1\\0\end{pmatrix}, \begin{pmatrix}r_k\\s_k\\t_k\end{pmatrix} = A^t\begin{pmatrix}0\\0\\1\end{pmatrix} \tag{53}$$

It is noted that the above-referenced a, b and c denote angles of rotation with respect to the r, s and t axes, respectively, when the r, s and t axes are rotated in the named order.

In case of $-(\pi/2) \leq a \leq (\pi/2)$, $-(\pi/2) \leq b \leq (\pi/2)$, $-(\pi/2) \leq c \leq (\pi/2)$, a, b, c are expressed as follows.

$$b = \sin^{-1}(-t_i) \tag{54}$$

$$c = \sin^{-1}\left(\frac{s_i}{\sqrt{1-t_i^2}}\right) \tag{55}$$

$$a = \sin^{-1}\left(\frac{t_j}{\sqrt{1-t_i^2}}\right) \tag{56}$$

From the above, when an arbitrary point $P_n$ exists and the coordinate value of the point in the r s t coordinate system is given by the $P_n(r_n, s_n, t_n)$, a coordinate value in the i j k coordinate system can be determined on the basis of the following expressions.

$$\begin{pmatrix}i_n\\j_n\\k_n\end{pmatrix} = B\begin{pmatrix}r_n - r_b\\s_n - s_b\\t_n - t_b\end{pmatrix} \tag{57}$$

$$B = \begin{pmatrix}\cos b\cos c & \cos b\sin c & -\sin b \\ \sin a\sin b\cos c - \cos a\sin c & \sin a\sin b\sin c + \cos a\cos c & \sin a\cos b \\ \cos a\sin b\cos c + \sin a\sin c & \cos a\sin b\sin c - \sin a\cos c & \cos a\cos b\end{pmatrix}$$

[Determine the relationship of the i j k coordinate system with the X Y Z coordinate system]

The coordinate values of the points $P_0$, $P_1$, $P_2$ of the X Y Z coordinate system are given as follows.

$$P_0(x_0, y_0, z_0)$$

$$P_1(x_1, y_1, z_1)$$

$$P_2(x_2, y_2, z_2) \tag{58}$$

The coordinate value of the origin $P_b$ of the i j k coordinate system on the X Y Z coordinates is given by $$P_b(x_b, y_b, z_b) \tag{59}$$

Further, the component of (vector$P_b P_2$) on the X Y Z coordinates is $$(\text{vector}P_b P_2) = (\text{vector } P_j) = (P_{jx}, P_{jy}, P_{jz})$$

The component of (vector$P_k$) on the X Y Z coordinates is, $$(\text{vector}P_k) = (\text{vector } P_b P_0) \times (\text{vector } P_b P_2) = (P_{kx}, P_{ky}, P_{kz}) \tag{60}$$

The component of (vector$P_1$) on the X Y Z coordinates is, $$(\text{vector}P_i) = (\text{vector } P_b P_2) \times (\text{vector } P_k) = (P_{ix}, P_{iy}, P_{iz}) \tag{61}$$

From the above, unit vectors (vector i), (vector j) and (vector k) for the i, j and k axes are determined, and the components on the X Y Z coordinates are expressed by $$\left.\begin{array}{l}(vector\ i) = (x_i, y_i, z_i) \\ (vector\ j) = (x_j, y_j, z_j) \\ (vector\ k) = (x_k, y_k, z_k)\end{array}\right\} \tag{62}$$

[Determine the relationship of the X Y Z coordinate system with the i j k coordinate system]

In the X Y Z coordinate system and the i j k coordinate system, when the i j k coordinates are rotated by $\zeta$, $\epsilon$ and $\delta$ for the k axis, the j axis and the i axis, respectively, with respect to the k axis, the j axis and the i axis in the named order, if the respective associated axes of these two coordinate systems are coincident with each other in their direction, the following expressions can be obtained.

$$\begin{pmatrix} x_i \\ y_i \\ z_i \end{pmatrix} = E \begin{pmatrix} 1 \\ 0 \\ 0 \end{pmatrix}, \begin{pmatrix} x_j \\ y_j \\ z_j \end{pmatrix} = E \begin{pmatrix} 0 \\ 1 \\ 0 \end{pmatrix}, \begin{pmatrix} x_k \\ y_k \\ z_k \end{pmatrix} = E \begin{pmatrix} 0 \\ 0 \\ 1 \end{pmatrix} \quad (63)$$

$$E = \begin{pmatrix} \cos\zeta\cos\varepsilon & \sin\zeta\cos\delta + \cos\zeta\sin\varepsilon\sin\delta & \sin\zeta\sin\delta - \cos\zeta\sin\varepsilon\cos\delta \\ -\sin\zeta\cos\varepsilon & \cos\zeta\cos\delta - \sin\zeta\sin\varepsilon\sin\delta & \cos\zeta\sin\delta + \sin\zeta\sin\varepsilon\cos\delta \\ \sin\varepsilon & -\cos\varepsilon\sin\delta & \cos\varepsilon\cos\delta \end{pmatrix}$$

In case of $-(\pi/2) \leq \zeta \leq (\pi/2)$, $-(\pi/2) \leq \varepsilon \leq (\pi/2)$, $-(\pi/2) \leq \delta \leq (\pi/2)$, the following expressions are established.

$$\varepsilon = \sin^{-1} z_i \quad (64)$$

$$\zeta = \sin^{-1}\left(-\frac{y_i}{\sqrt{1-z_i^2}}\right) \quad (65)$$

$$\delta = \sin^{-1}\left(-\frac{z_j}{\sqrt{1-z_i^2}}\right) \quad (66)$$

From the above, when an arbitrary point $P_n$ exists and the coordinate value of the point $P_n$ on the i j k coordinate system is given by the $P_n(i_n, j_n, k_n)$ the coordinate value $(x_n, x_n, x_n)$ of the point $P_n$ on the X Y Z coordinate system can be determined on the basis of the following expressions.

$$\begin{pmatrix} x_n \\ y_n \\ z_n \end{pmatrix} = \begin{pmatrix} x_b \\ y_b \\ z_b \end{pmatrix} + E \begin{pmatrix} i_n \\ j_n \\ k_n \end{pmatrix} \quad (67)$$

$$E = \begin{pmatrix} \cos\zeta\cos\varepsilon & \sin\zeta\cos\delta + \cos\zeta\sin\varepsilon\sin\delta & \sin\zeta\sin\delta - \cos\zeta\sin\varepsilon\cos\delta \\ -\sin\zeta\cos\varepsilon & \cos\zeta\cos\delta - \sin\zeta\sin\varepsilon\sin\delta & \cos\zeta\sin\delta + \sin\zeta\sin\varepsilon\cos\delta \\ \sin\varepsilon & -\cos\varepsilon\sin\delta & \cos\varepsilon\cos\delta \end{pmatrix}$$

[Determine the coordinate value of the origin of the r s t coordinates on the X Y Z coordinate system, and angles of rotation with respect to the r axis, the s axis and the t axis, when the coordinate values of the $P_0$, $P_1$ and $P_2$ are given]

Figure 32:
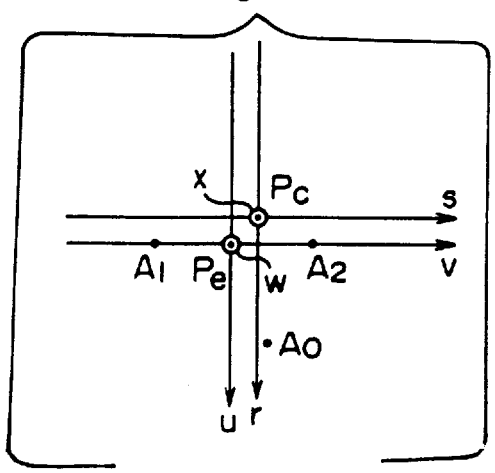
FIG. 32 is a view showing a coordinate system (rst) fixed on an operating plate and a coordinate system (uvw) which is determined by three points $A_o$, $A_1$ and $A_2$ on a surface A of the operating plate.

FIG. 32 is a view showing a coordinate system (rst) fixed on the operating plate 40 and a coordinate system (uvw) which is determined by three points $A_0$, $A_1$ and $A_2$ on a surface A of the operating plate 40.

In consideration of points $A_0, A_1, A_2$ on the surface A, and an orthogonal coordinate system u v w coordinates in which the middle point of the segment $A_1A_2$ is given as the origin; the normal line of the surface A as w axis; and (vector $A_1$, $A_2$) as v axis, it is assumed that the v axis is parallel to s axis on the r s t coordinate system.

At that time, it is assumed that the coordinate system of the points $A_0$, $A_1$ and $A_2$ on the r s t coordinate system are expressed by $$A_0(r_{a0}, s_{a0}, 0)$$

$$A_1(r_{a1}, s_{a1}, 0)$$

$$A_2(r_{a2}, s_{a2}, 0)$$

From the above conditions, $r_{a1} = r_{a2}$.

The coordinate values of $A_0$, $A_1$ and $A_2$ on the i j k coordinate system are determined from equation (67) as follows.

$$A_0 \begin{pmatrix} i_{a0} \\ j_{a0} \\ k_{a0} \end{pmatrix} = B \begin{pmatrix} r_{a0} - r \\ b s_{a0} - s \\ b t_b \end{pmatrix} \quad (68)$$

$$A_1 \begin{pmatrix} i_{a1} \\ j_{a1} \\ k_{a1} \end{pmatrix} = B \begin{pmatrix} r_{a1} - r \\ b s_{a1} - s \\ b t_b \end{pmatrix}$$

$$A_2 \begin{pmatrix} i_{a2} \\ j_{a2} \\ k_{a2} \end{pmatrix} = B \begin{pmatrix} r_{a2} - r \\ b s_{a2} - s \\ b t_b \end{pmatrix}$$

$$B = \begin{pmatrix} \cos b \cos c & \cos b \sin c & -\sin b \\ \sin a \sin b \cos c - \cos a \sin c & \sin a \sin b \sin c + \cos a \cos c & \sin a \cos b \\ \cos a \sin b \cos c + \sin a \sin c & \cos a \sin b \sin c - \sin a \cos c & \cos a \cos b \end{pmatrix}$$

The coordinate values of the points $A_0$, $A_1$ and $A_2$ on the X Y Z coordinate system are determined from equation (67) as follows.

$$A_0 \begin{pmatrix} x_{a0} \\ y_{a0} \\ z_{a0} \end{pmatrix} = \begin{pmatrix} x_b \\ y_b \\ z_b \end{pmatrix} + E \begin{pmatrix} i_{a0} \\ j_{a0} \\ k_{a0} \end{pmatrix} \quad (69)$$

$$A_1 \begin{pmatrix} x_{a1} \\ y_{a1} \\ z_{a1} \end{pmatrix} = \begin{pmatrix} x_b \\ y_b \\ z_b \end{pmatrix} + E \begin{pmatrix} i_{a1} \\ j_{a1} \\ k_{a1} \end{pmatrix}$$

$$A_2 \begin{pmatrix} x_{a2} \\ y_{a2} \\ z_{a2} \end{pmatrix} = \begin{pmatrix} x_b \\ y_b \\ z_b \end{pmatrix} + E \begin{pmatrix} i_{a2} \\ j_{a2} \\ k_{a2} \end{pmatrix}$$

$$E = \begin{pmatrix} \cos\zeta\cos\varepsilon & \sin\zeta\cos\delta + \cos\zeta\sin\varepsilon\sin\delta & \sin\zeta\sin\delta - \cos\zeta\sin\varepsilon\cos\delta \\ -\sin\zeta\cos\varepsilon & \cos\zeta\cos\delta - \sin\zeta\sin\varepsilon\sin\delta & \cos\zeta\sin\delta + \sin\zeta\sin\varepsilon\cos\delta \\ \sin\varepsilon & -\cos\varepsilon\sin\delta & \cos\varepsilon\cos\delta \end{pmatrix}$$

[Determine components of the unit vectors (vector u), (vector v) and (vector w) on the u v w coordinate system, on the X Y Z coordinate system, on the basis of the values of the points $A_0$, $A_1$ and $A_2$ on the X Y Z ]

Figure 33:
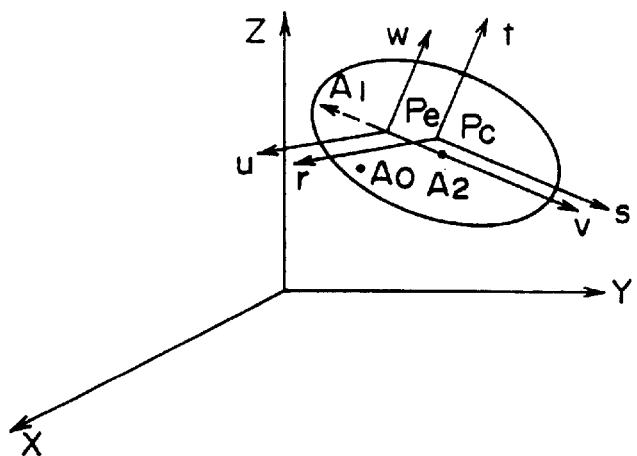
FIG. 33 is a view showing a reference coordinate system (XYZ), and the two coordinate systems (rst) and (uvw) shown in FIG. 32.

FIG. 33 is a view showing a reference coordinate system (XYZ), and the two coordinate systems (rst) and (uvw) shown in FIG. 32.

The coordinate value of the origin $P_e$ of the u v w coordinates on the X Y Z coordinates is expressed by $$P_e = (x_e, y_e, z_e) \quad (70)$$

The component of (vector $P_e A_2$) coincident with the v axis is expressed by (vector $P_e A_2$)=(vector $P_v$)=($P_{vx}$, $P_{vy}$, $P_{vz}$)

(vector $P_w$) coincident with the w axis is expressed by (vector $P_w$)=(vector$P_e A_0$)×(vector$P_e A_2$)=($P_{wx}$, $P_{wy}$, $P_{wz}$)

(vector $P_u$) coincident with the u axis is expressed by (vector $P_u$)=(vector $P_e A_2$)×(vector$P_w$)=($P_{ux}$, $P_{uy}$, $P_{uz}$)

From the above, the unit vectors (vector u), (vector v) and (vector w) with respect to the u, v and w axes are determined, and their components are expressed by $$\begin{aligned}(\text{vector } u) &= (x_u, u_u, z_u) \\ (\text{vector } v) &= (x_v, u_v, z_v) \\ (\text{vector } w) &= (x_w, u_w, z_w)\end{aligned} \right\} \quad (71)$$

It is assumed that in the u v w coordinates and the X Y Z coordinate system, when the X Y Z coordinates are rotated by $\alpha$, $\beta$ and $\gamma$ on the X axis, the Y axis and the Z axis, respectively, with respect to the X axis, the Y axis and the Z axis in the named order, the respective associated axes of these two coordinate systems are coincident with each other in their direction.

This permits the following expressions to be induced.

$$\begin{pmatrix}1\\0\\0\end{pmatrix} = F\begin{pmatrix}x_u\\y_u\\z_u\end{pmatrix}, \begin{pmatrix}0\\1\\0\end{pmatrix} = F\begin{pmatrix}x_v\\y_v\\z_v\end{pmatrix}, \begin{pmatrix}0\\0\\1\end{pmatrix} = F\begin{pmatrix}x_w\\y_w\\z_w\end{pmatrix} \quad (72)$$

$$F = \begin{pmatrix} \cos\beta\cos\gamma & \cos\beta\sin\gamma & -\sin\beta \\ \sin\alpha\sin\beta\cos\gamma - \cos\alpha\sin\gamma & \sin\alpha\sin\beta\sin\gamma + \cos\alpha\cos\gamma & \sin\alpha\cos\beta \\ \cos\alpha\sin\beta\cos\gamma + \sin\alpha\sin\gamma & \cos\alpha\sin\beta\sin\gamma - \sin\alpha\cos\gamma & \cos\alpha\cos\beta \end{pmatrix}$$

The XYZ coordinates and the u v w coordinate are orthogonal coordinate system. Therefore, the following expressions exist $$\begin{pmatrix}x_u\\y_u\\z_u\end{pmatrix} = F^t\begin{pmatrix}1\\0\\0\end{pmatrix}, \begin{pmatrix}x_v\\y_v\\z_v\end{pmatrix} = F^t\begin{pmatrix}0\\1\\0\end{pmatrix}, \begin{pmatrix}x_w\\y_w\\z_w\end{pmatrix} = F^t\begin{pmatrix}0\\0\\1\end{pmatrix} \quad (73)$$

Here, in condition of $-(\pi/2) \leq \alpha \leq (\pi/2)$, $-(\pi/2) \leq \beta \leq (\pi/2)$, $-(\pi/2) \leq \gamma \leq (\pi/2)$, $\alpha$, $\beta$, $\gamma$ are determined. Then $$\beta = \sin^{-1}(z_u) \quad (74)$$

$$\gamma = \sin^{-1}\left(\frac{y_u}{\sqrt{1-z_u^2}}\right) \quad (75)$$

$$\alpha = \sin^{-1}\left(\frac{z_v}{\sqrt{1-z_u^2}}\right) \quad (76)$$

Thus, it is possible to determine angles $\alpha$, $\beta$, $\gamma$ (rotating in the order of the X, Y, Z axes) of rotation of the r s t coordinates with respect to the X Y Z coordinates.

Next, the coordinate value of the origin $P_c$ of the r s t coordinates on the X Y Z coordinates is determined. The coordinate value of the origin $P_c$ of the r s t coordinates is the origin of the r s t coordinates. Therefore, it is expressed by (0, 0, 0).

The coordinate values $(i_c, j_c, k_c)$ of the origin $P_c$ on the i j k coordinates are expressed from the equation (67) by the following equation (77).

$$\begin{pmatrix}i_c\\j_c\\k_c\end{pmatrix} = B\begin{pmatrix}0-r_b\\0-s_b\\0-t_b\end{pmatrix} = B\begin{pmatrix}-r_b\\-s_b\\-t_b\end{pmatrix} \quad (77)$$

$$B = \begin{pmatrix} \cos b\cos c & \cos b\sin c & -\sin b \\ \sin a\sin b\cos c - \cos a\sin c & \sin a\sin b\sin c + \cos a\cos c & \sin a\cos b \\ \cos a\sin b\cos c + \sin a\sin c & \cos a\sin b\sin c - \sin a\cos c & \cos a\cos b \end{pmatrix}$$

From equation (67), coordinate values $(x_c, y_c, z_c)$ of $P_c$ on the X Y Z coordinates are given by the following equation (78).

$$\begin{pmatrix} x_c \\ y_c \\ z_c \end{pmatrix} = \begin{pmatrix} x_b \\ y_b \\ z_b \end{pmatrix} + E \begin{pmatrix} i_c \\ j_c \\ k_c \end{pmatrix} \tag{78}$$

$$E = \begin{pmatrix} \cos\zeta\cos\varepsilon & \sin\zeta\cos\delta + \cos\zeta\sin\varepsilon\sin\delta & \sin\zeta\sin\delta - \cos\zeta\sin\varepsilon\cos\delta \\ -\sin\zeta\cos\varepsilon & \cos\zeta\cos\delta - \sin\zeta\sin\varepsilon\sin\delta & \cos\zeta\sin\delta + \sin\zeta\sin\varepsilon\cos\delta \\ \sin\varepsilon & -\cos\varepsilon\sin\delta & \cos\varepsilon\cos\delta \end{pmatrix}$$

From the above, it is possible to determine, when the coordinate values of the points $P_0$, $P_1$ and $P_2$ are given in the X Y Z coordinate system and the r s t coordinate system:

- rotating angle α on the X axis (r axis) from the equation (76);
- rotating angle β on the Y axis (s axis) from the equation (77);
- rotating angle γ on the Z axis (t axis) from the equation (78); and
- (rotating in the named order)
- coordinate values of the reference point $P_c$ (the origin of the r s t coordinate) on the X Y Z coordinate from the equation (78).

Operation as to the second embodiment shown in FIG. 25, after the rotating angles α, β, γ and the coordinate value of the reference point $P_c$ (the origin of the r s t coordinate) on the X Y Z coordinate are determined in the manner as mentioned above, is the same as that of the first embodiment explained referring to FIG. 11, and thus the redundant explanation will be omitted.

The above-mentioned description is concerned with the explanation of the algorithm in which the teeth constituting of the lower jaw model, which are equivalent to the teeth indicated by the pointer pen 19 at the time of photographing, are in contact with the tip of the contact detection probe unit 41, the angles of rotation of the rotating shafts 35a of the servo motors 35 are detected through the angle detectors 35b, and the coordinate of the lower jaw model is identified on the basis of information obtained by detection of the angle detectors 35b. On the other hand, as shown in FIG. 27 in the form of the third embodiment, it is acceptable that there is provided the handler for manually moving the lower jaw model 310 fixed on the operating plate 40, and a desired tooth of the lower jaw model is in contact with the tip of the contact detection probe through operating the handler. In this case, as compared with the second embodiment shown in FIG. 25, generally, while it takes relatively much time that a tooth is in contact with the tip of the contact detection probe unit, it is possible to reduce an operation time for identifying the coordinate system of the lower jaw model, since information obtained through the handler in the state that the tooth is in contact with the tip of the contact detection probe unit is directly representative of positional information of the operating plate.

Figure 34:
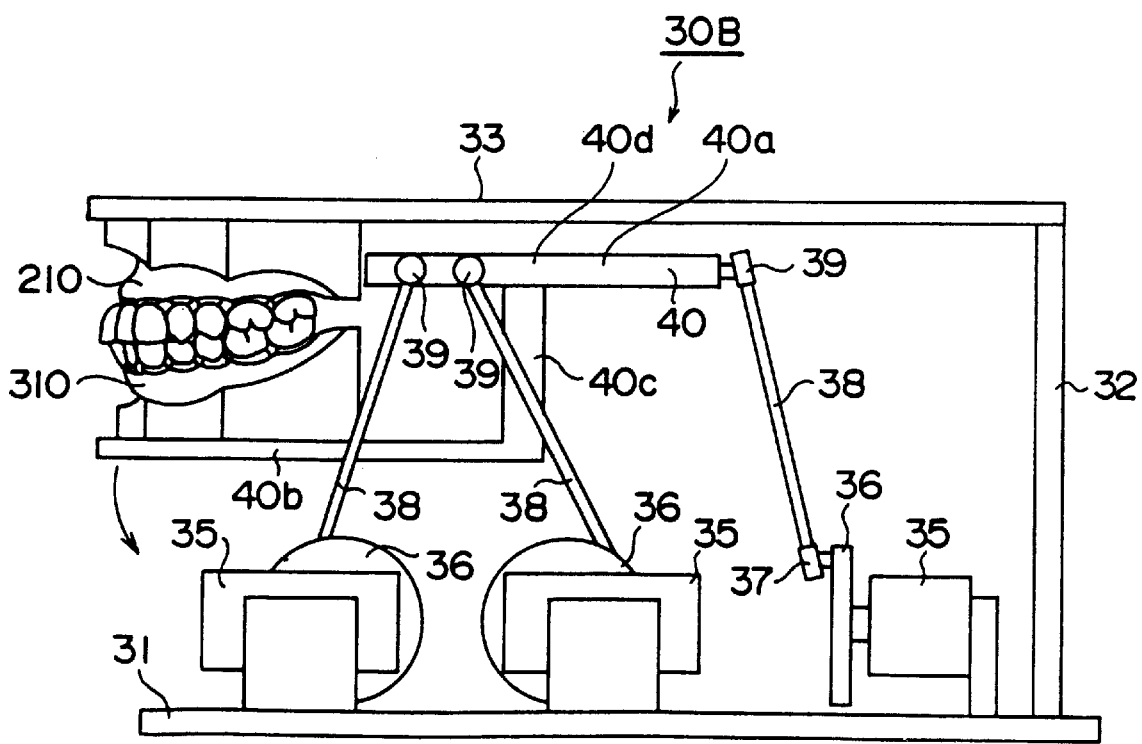
FIG. 34 is a typical illustration useful for understanding a fourth embodiment of a jaw movement reproducing apparatus constituting a jaw movement simulator according to the present invention.

FIG. 34 is a typical illustration useful for understanding a fourth embodiment of a jaw movement reproducing apparatus constituting a jaw movement simulator according to the present invention.

There will be described only a difference between it and the first embodiment shown in FIG. 11.

An operating plate 40 of the jaw movement reproducing apparatus 30B shown shown in FIG. 34 is not a simple one disk, but comprises a first member 40a consisting of a piece of disk and a second member 40b on which the lower jaw model 310 is fixed, the second member 40b being disposed at the position apart from the first member 40a. The first member 40a and the second member 40b are fixedly coupled with each other through a coupling member 40c.

Figure 1:
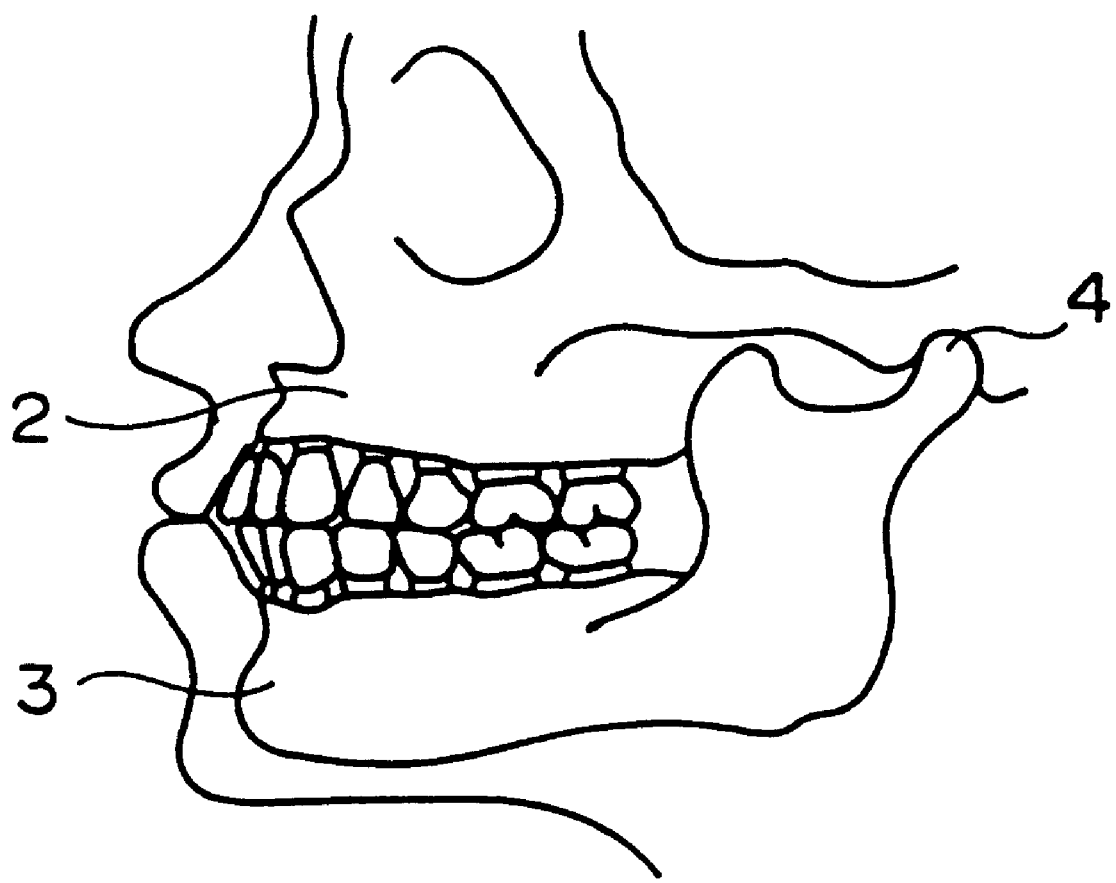
FIG. 1 is a typical illustration of part of the jaw of the human body.

Incidentally, while the operating plate 40 shown in FIG. 34 is not a piece of "plate", the term "operating plate 40" is used as it is, in comparison with the first embodiment shown in FIG. 11. This is similar also in other embodiments which will be described hereinafter. A point 40d, at which the first member 40a is coupled with the coupling member 40c, approximately corresponds to the position of the condyle 4 of the jaw of the human as shown in FIG. 1. The lower jaw greatly moves in opening and shutting directions of the mouth. Consequently, if the lower jaw model 310 is directly mounted on the operating plate 40 having the disk-like configuration as shown in FIG. 11, there is a need to greatly move the operating plate 40. Thus, it is necessary to adopt a horn 36 having a large diameter. On the contrary, a movement of the condyle is little. Accordingly, in case of the structure shown in FIG. 34, a movement of the first member 40a constituting the operating plate 40 may be little, and thus a horn 36 having a small diameter can be used, thereby miniaturizing the apparatus in its entirety.

The first member 40a and the second member 40b are fixedly coupled with each other through a coupling member 40c. Therefore, there is no need to specifically consider a new coordinate system, and thus the operating plate 40 may be dealt with in its entirety as one united body.

Figure 35:
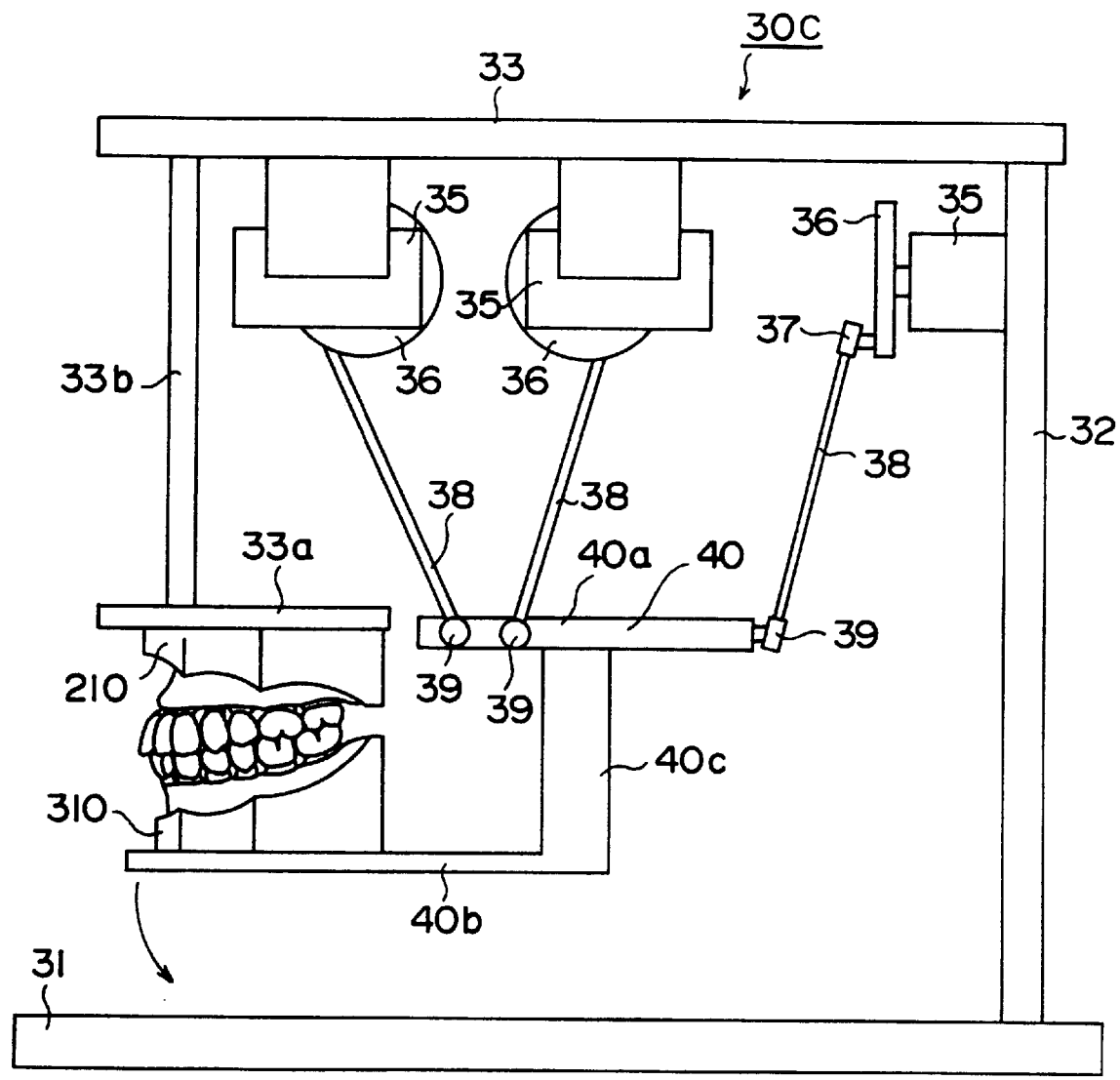
FIG. 35 is a typical illustration useful for understanding a fifth embodiment of a jaw movement reproducing apparatus constituting a jaw movement simulator according to the present invention.

FIG. 35 is a typical illustration useful for understanding a fifth embodiment of a jaw movement reproducing apparatus constituting a jaw movement simulator according to the present invention. There will be described a difference between it and the fourth embodiment shown in FIG. 34.

According to the fifth embodiment shown in FIG. 35, the servo motors 35 etc. are arranged on the ceiling board 33 and the poles 32, and an upper jaw model 210 is fixed on a plate 33a which is coupled with the ceiling board 33 through a coupling member 33b. An operating plate 40 fixed on the jaw model 310 has the same structure as that in the fourth embodiment shown in FIG. 34. It is also the same as the fourth embodiment shown in FIG. 34 in the point that the horn 36 having the small diameter can be used. It is noted that also in case of the structure shown in FIG. 35, there is no need to consider a new coordinate system.

Figure 36:
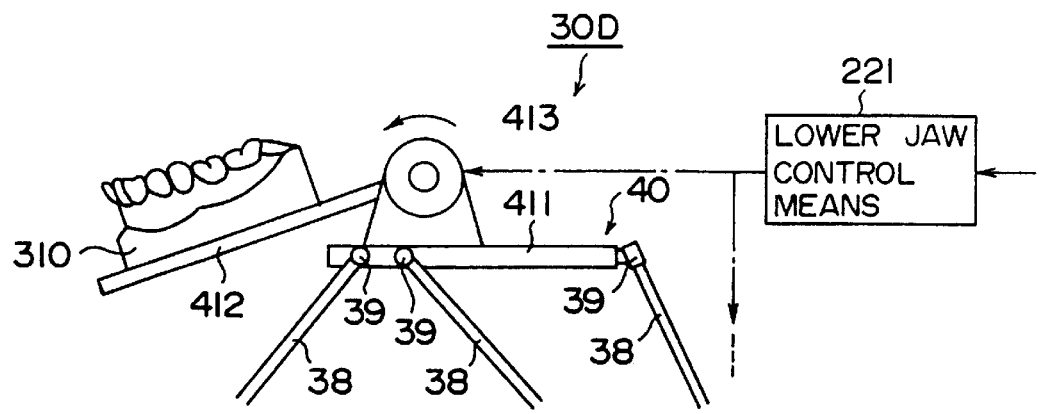
FIG. 36 is a typical illustration useful for understanding a sixth embodiment of a jaw movement reproducing apparatus constituting a jaw movement simulator according to the present invention, but showing only a part which is different from the first embodiment shown in FIG. 11.

FIG. 36 is a typical illustration useful for understanding a sixth embodiment of a jaw movement reproducing apparatus constituting a jaw movement simulator according to the present invention, but showing only a part which is different from the first embodiment shown in FIG. 11.

An operating plate 40 constituting a jaw movement reproducing unit 30D shown in FIG. 36 comprises a first member 411 coupled with links 38 through ball joints 39, a second member 412 on which the lower jaw model 310 is fixed, and a rotational joint 413 fixed on the first member 411 for rotatably moving the second member 412 in up and down directions with respect to the first member 411. According to the sixth embodiment, a lower jaw control means 221 controls angles of rotation of the rotating shafts 35a of the 6 servo motors 35 shown in FIG. 11 and an angle of rotation of the rotational joint 413 as well.

Also in case of the sixth embodiment shown in FIG. 36, the use of the rotational joint 413 enables a movement of the mouth in opening and shutting directions, and permits a little movement of the operating plate 40 by the servo motors 35, thereby miniaturizing the horn 36. Thus, it is possible to miniaturize-the apparatus in its entirety.

According to the sixth embodiment shown in FIG. 36, there is disposed a parallel mechanism such as the rotational joint 413 between the first member 411 and the second member 412. Accordingly, there is a need to consider an algorithm which is different from the algorithm mentioned above. [Algorithm in case of combination of the parallel mechanism and the serial mechanism]

It is assumed that as data representative of a movement of the lower jaw, there are provided movement data for three points $P_0, P_1, P_2$ of the bottom of the lower jaw model. Now considering an i j k coordinate system defined by the three points $P_0, P_1, P_2$, it is assumed that components of unit vectors of the i j k coordinate system on the X Y Z coordinate system are expressed by (vector i)=$(x_i, y_i, z_i)$ (vector j)=$(x_j, y_j, z_j)$ (vector k)=$(x_k, y_k, z_k)$ It is assumed that a rotation on the Y axis is performed by the serial mechanism (it is also possible to perform a partial rotation on the Y axis by the serial mechanism).

It is assumed that an attitude of the plane defined by the three points $P_0, P_1, P_2$ is produced through rotating X, Z and y axes in the named order. When angles of rotation on X, Z and Y axes are denoted by $\alpha$, $\beta$ and $\gamma$, respectively, the following expressions are given.

$$\begin{pmatrix} x_i \\ y_i \\ z_i \end{pmatrix} = D^t \begin{pmatrix} 1 \\ 0 \\ 0 \end{pmatrix}, \begin{pmatrix} x_j \\ y_j \\ z_j \end{pmatrix} = D^t \begin{pmatrix} 0 \\ 1 \\ 0 \end{pmatrix}, \begin{pmatrix} x_k \\ y_k \\ z_k \end{pmatrix} = D^t \begin{pmatrix} 0 \\ 0 \\ 1 \end{pmatrix}$$

$$D^t = \begin{pmatrix} \cos\gamma\cos\beta & -\cos\alpha\sin\gamma\cos\beta+\sin\alpha\sin\beta & \sin\alpha\sin\gamma\cos\beta-\cos\alpha\sin\beta \\ \sin\gamma & \cos\alpha\cos\gamma & -\sin\alpha\cos\gamma \\ -\cos\gamma\sin\beta & \cos\alpha\sin\gamma\sin\beta+\sin\alpha\cos\beta & -\sin\alpha\sin\gamma\sin\beta+\cos\alpha\cos\beta \end{pmatrix}$$

In case of $-(\pi/2) \leq \alpha \leq (\pi/2)$, $-(\pi/2) \leq \beta \leq (\pi/2)$, $-(\pi/2) \leq \gamma \leq (\pi/2)$, the following expressions are given.

$$j = \sin^{-1} y_i$$

$$\cos\gamma = \sqrt{1-\sin^2\gamma} = \sqrt{1-y_i^2}$$

$$\sin\beta = \frac{z_i}{-\cos\gamma} = -\frac{z_i}{\sqrt{1-y_i^2}}$$

$$\sin\alpha = \frac{y_k}{-\cos\gamma} = -\frac{y_k}{\sqrt{1-y_i^2}}$$

From the above, angles $\alpha$, $\gamma$ and $\beta$ of rotation, when X axis, Z axis and Y axis are rotated on their axes, respectively, in the named order, are determined.

Let us consider such a case that the rotational movement for the X axis and the Z axis, and the translational movement for the X axis, the y axis and the Z axis are performed by the parallel mechanism, and the rotational movement for the Y axis is performed by the serial mechanism.

The coordinate values $(x_0, y_0, z_0)$ of a parallel mechanism operating plate on the actuator coordinate (X Y Z coordinates) with the ball joint center can be determined from the following expressions, when the coordinates with the joint center with respect to the coordinate system (r s t coordinate system) on the operating plate are given by $(r_0, s_0, t_0)$ $$\begin{pmatrix} x_o \\ y_o \\ z_o \end{pmatrix} = \begin{pmatrix} \Delta x \\ \Delta y \\ \Delta z \end{pmatrix} + E \begin{pmatrix} r_o \\ s_o \\ t_o \end{pmatrix}$$

$$E = \begin{pmatrix} \cos\gamma & -\sin\gamma & 0 \\ \cos\alpha\sin\gamma & \cos\alpha\cos\gamma & -\sin\alpha \\ \sin\alpha\sin\gamma & \sin\alpha\cos\gamma & \cos\gamma \end{pmatrix}$$

$$\begin{pmatrix} \Delta x \\ \Delta y \\ \Delta z \end{pmatrix} = \begin{pmatrix} x_m \\ y_m \\ z_m \end{pmatrix} + \begin{pmatrix} x_d \\ y_d \\ z_d \end{pmatrix} + \begin{pmatrix} x(\beta) \\ 0 \\ z(\beta) \end{pmatrix}$$

$\begin{pmatrix} x_m \\ y_m \\ z_m \end{pmatrix}$ : coordinate values of i j k coordinate points in the actuator $\begin{pmatrix} x_d \\ y_d \\ z_d \end{pmatrix}$ : correction term by the relationship between a model position and a moving plate position $\begin{pmatrix} x(\beta) \\ 0 \\ z(\beta) \end{pmatrix}$ : correction term by Y axis rotation In a similar fashion, it is possible to determine of the coordinate values of other ball joints.

It is possible to obtain an angle of rotation of the horn by means of determining an intersection of the sphere and the circle in the manner as mentioned above, on the basis of the coordinate values of the 6 ball joints.

Even in the event that the Y axis rotation is performed with the use of both the serial mechanism and the parallel mechanism, the following expressions are available instead of the transformation matrix.

$$\begin{pmatrix} \cos\gamma\ \cos\beta' & -\sin\gamma & \cos\gamma\ \sin\beta' \\ \cos\alpha\ \sin\gamma\ \cos\beta' + \sin\alpha\ \sin\beta' & \cos\alpha\ \cos\gamma & \cos\alpha\ \sin\gamma\ \sin\beta' - \sin\alpha\ \cos\beta' \\ \sin\alpha\ \sin\gamma\ \cos\beta' - \cos\alpha\ \sin\beta' & \sin\alpha\ \cos\gamma & \sin\alpha\ \sin\gamma\ \sin\beta' + \cos\alpha\ \cos\beta' \end{pmatrix}$$

$\beta'$: angle of rotation in the parallel mechanism

Figure 37:
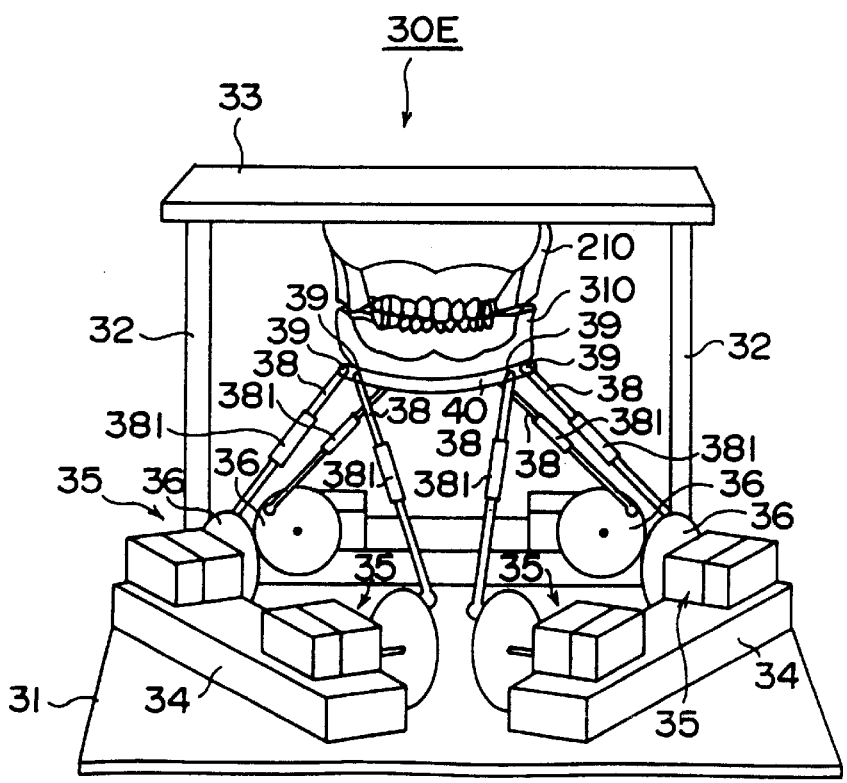
FIG. 37 is a typical illustration useful for understanding a seventh embodiment of a jaw movement reproducing apparatus constituting a jaw movement simulator according to the present invention.
Figure 38:
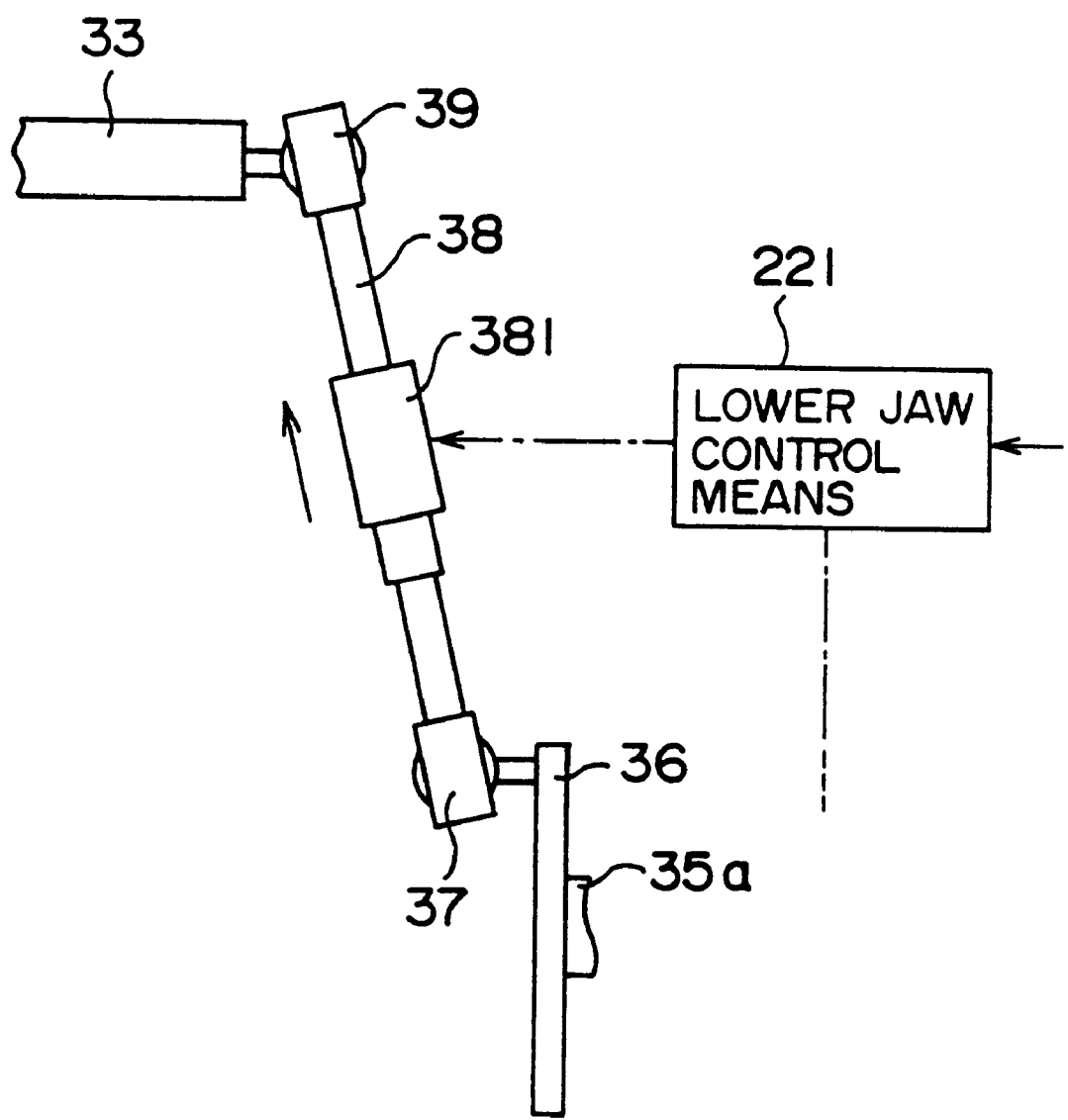
FIG. 38 is a typical illustration showing a portion of a link constituting the jaw movement reproducing apparatus shown in FIG. 37.

FIG. 37 is a typical illustration useful for understanding a seventh embodiment of a jaw movement reproducing apparatus constituting a jaw movement simulator according to the present invention. FIG. 38 is a typical illustration showing a portion of a link constituting the jaw movement reproducing apparatus shown in FIG. 37. There will be described a difference between it and the first embodiment shown in FIG. 11.

In a jaw movement reproducing apparatus 30E shown in FIG. 37, there is provided a linear actuator 381 on the center of each of 6 links 38. According to the present embodiment, as shown in FIG. 38, a lower jaw control means 221 controls rotational positions of the rotating shafts of 6 servo motors and in addition operating quantity of each of the 6 linear actuator 381.

Also in the event that such linear actuator 381 are provided, it is possible to reduce the radius of the horn 36, and thereby contributing to miniaturization of the apparatus in its entirety.

In the event that such linear actuator 381 are provided, the associated algorithm is provided as follows.

[Algorithm of the parallel mechanism using rotational actuators and linear actuators]

In consideration of the orthogonal coordinates rst coordinates in which the center on the operating plate 40 is given as the origin, and when the plate center coordinate values (x, y, z) on the coordinate system (X Y Z coordinate) of the actuator and the angles ($\alpha$, $\beta$, $\gamma$) of rotation on the plate coordinate axis are given, the coordinate values ($x_0$, $y_0$, $z_0$) on the X Y Z coordinate system of the ball joint center of the operating plate are determined from the following expressions.

$$\begin{pmatrix} x_o \\ y_o \\ z_o \end{pmatrix} = \begin{pmatrix} x \\ y \\ z \end{pmatrix} + \begin{pmatrix} \cos\beta\ \cos\gamma & -\cos\beta\ \sin\gamma & \sin\beta \\ \sin\alpha\ \sin\beta\ \cos\gamma + \cos\alpha\ \sin\gamma & -\sin\alpha\ \sin\beta\ \sin\gamma + \cos\alpha\ \cos\gamma & -\sin\alpha\ \cos\beta \\ -\cos\alpha\ \sin\beta\ \cos\gamma + \sin\alpha\ \sin\gamma & \cos\alpha\ \sin\beta\ \sin\gamma + \sin\alpha\ \cos\gamma & \cos\alpha\ \cos\beta \end{pmatrix} \begin{pmatrix} r_o \\ s_o \\ t_o \end{pmatrix}$$

($r_0$, $s_0$, $t_0$) are coordinate values of the ball joint center on the r s t coordinate system.

(Operation at the time of horn rotation)

As mentioned above, an angle of rotation of the horn can be determined by computing an intersection of the sphere and the circle.

(Operation when length of the link is varied)

Also it is possible to determine it from the intersection of the sphere and the circle.

A point group of the intersection of sphere B and plane A becomes a circle, and the circle $C_A$ is given by the following expression.

$(u-u_0)^2+(v-v_0)^2+(z-z_0)^2=R^2$

R becomes the radius of sphere B and thus length of link. At that time, the horn stops at a certain angle. Hence, u, v, z offer known values. If $u=u^{hb}$, $v=v_{hb}$, $z=z_{hb}$, $R=\sqrt{\{(u_{hb}-u_0)^2+(v_{hb}-v_0)^2+(z_{hb}-z_0)^2\}}$ It is optional as to whether an operation of the operating plate is implemented by rotating the horn or varying length of the link. For example, while length of the link is maintained minimum, the operation is implemented by rotating the horn. In the state that the horn is right above, the horn is stopped in rotation, and thereafter the operation is performed by making length of the link longer. Alternatively, the reverse option may be considered.

Figure 39:
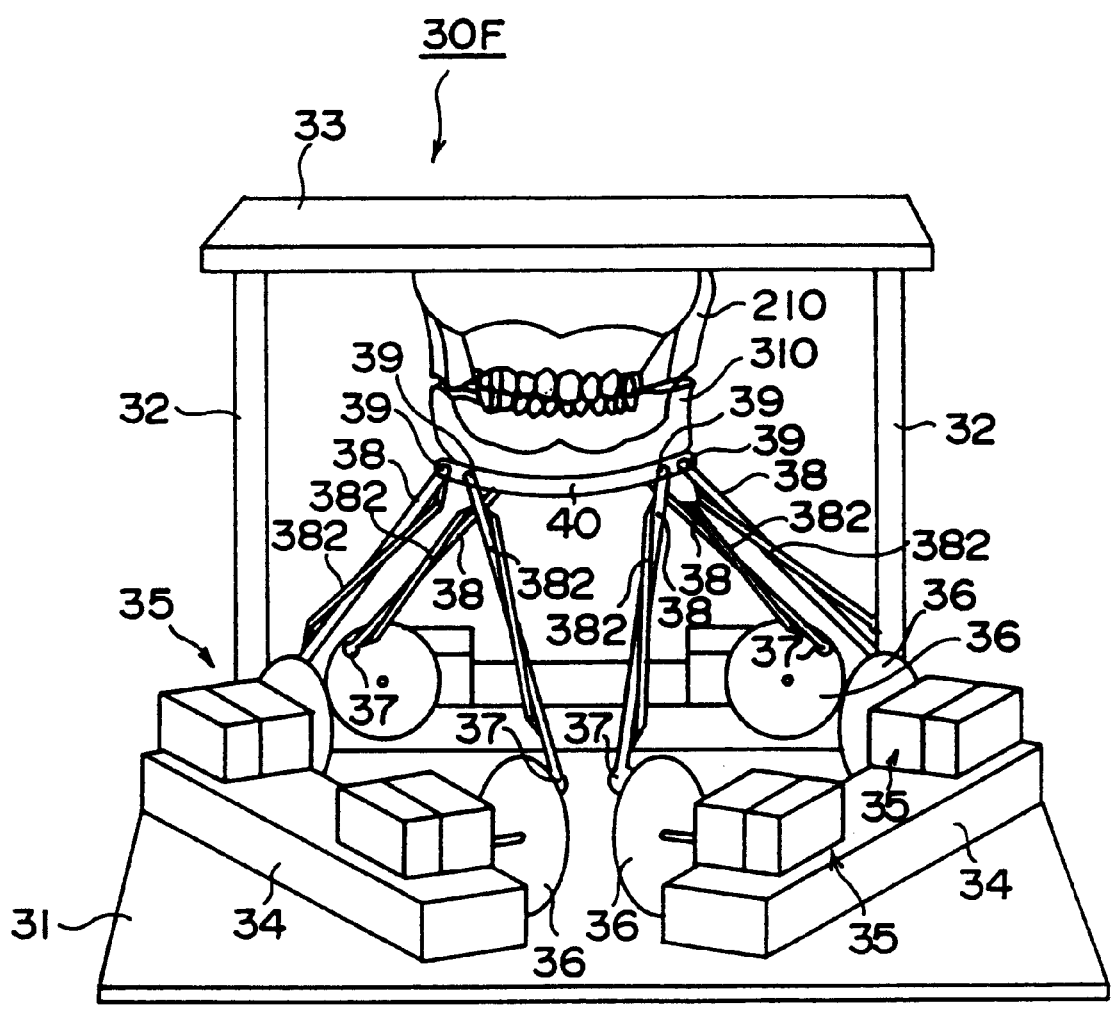
FIG. 39 is a typical illustration useful for understanding an eighth embodiment of a jaw movement reproducing apparatus constituting a jaw movement simulator according to the present invention.
Figure 40:
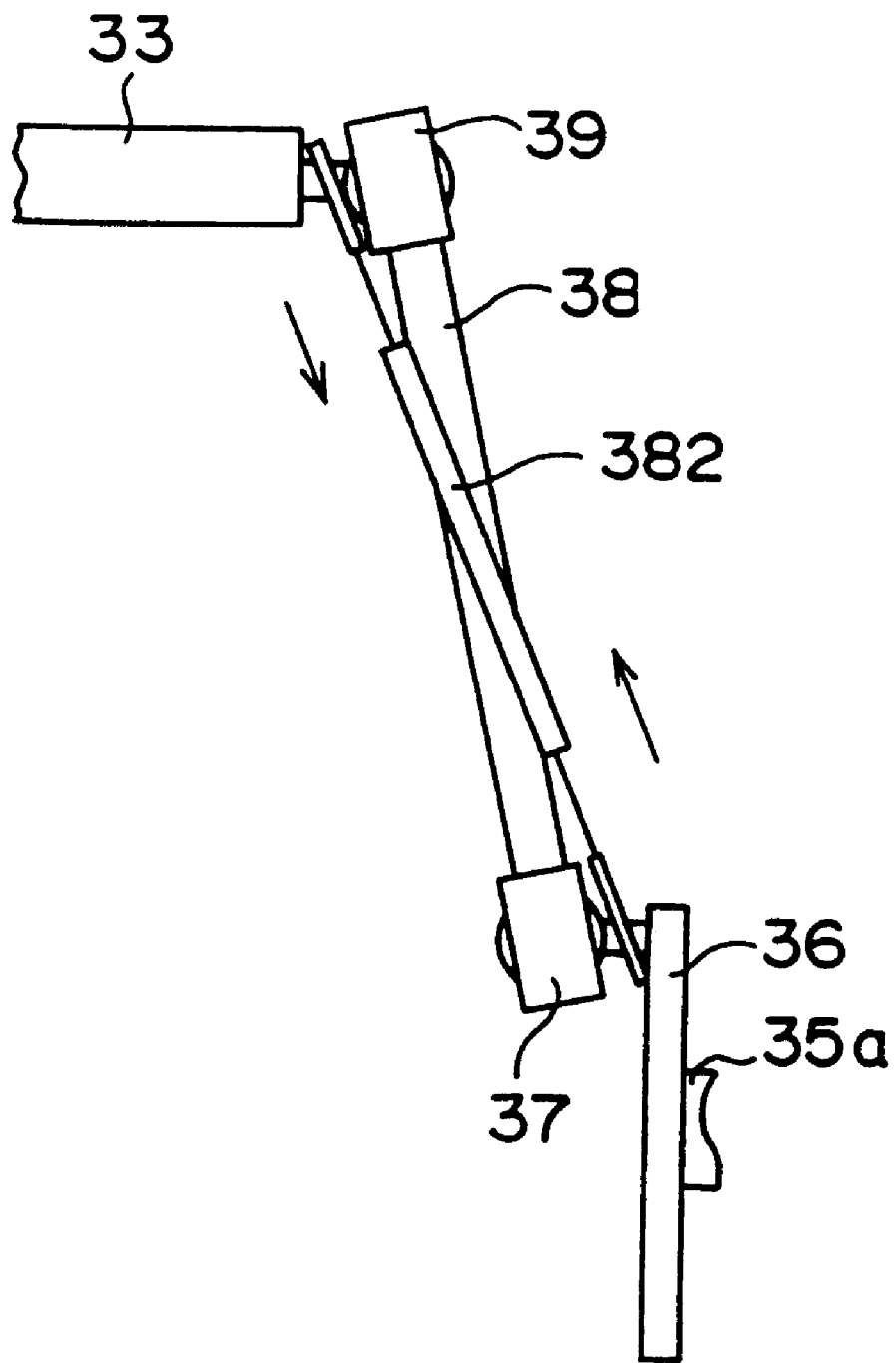
FIG. 40 is a typical illustration showing a portion of a link constituting the jaw movement reproducing apparatus shown in FIG. 39.

FIG. 39 is a typical illustration useful for understanding an eighth embodiment of a jaw movement reproducing apparatus constituting a jaw movement simulator according to the present invention. FIG. 40 is a typical illustration showing a portion of a link constituting the jaw movement reproducing apparatus shown in FIG. 39. There will be described a difference between it and the first embodiment shown in FIG. 11.

An operating plate 40 has 6 degree of freedom. In order to ensure 6 degree of freedom, 6 links 38 are connected through the ball joints 39 to the operating plate 40, and also connected through other ball joints 37 to the horns 36. It is difficult to completely suppress backlash of the ball joints 37 and 39. There is a fear that such a backlash involves degradation of the operational accuracy of the lower jaw model 310.

In the event that there is needed such a great accuracy that a problem of the backlash of the ball joints 37 and 39 arises, a tension spring 382 is provided between the vicinity of the ball joint 39 of the operating plate 40 and the vicinity of the ball joint 37 of the horn 36. This makes it possible to prevent a degradation of operational accuracy due to the backlash of the ball joints 37 and 39. The way of loading of the tension spring 382 as shown in FIG. 40 brings about such an advantage that a pull strength of the tension spring 382 serves as no direct load onto the servo motor 35.

Figure 41:
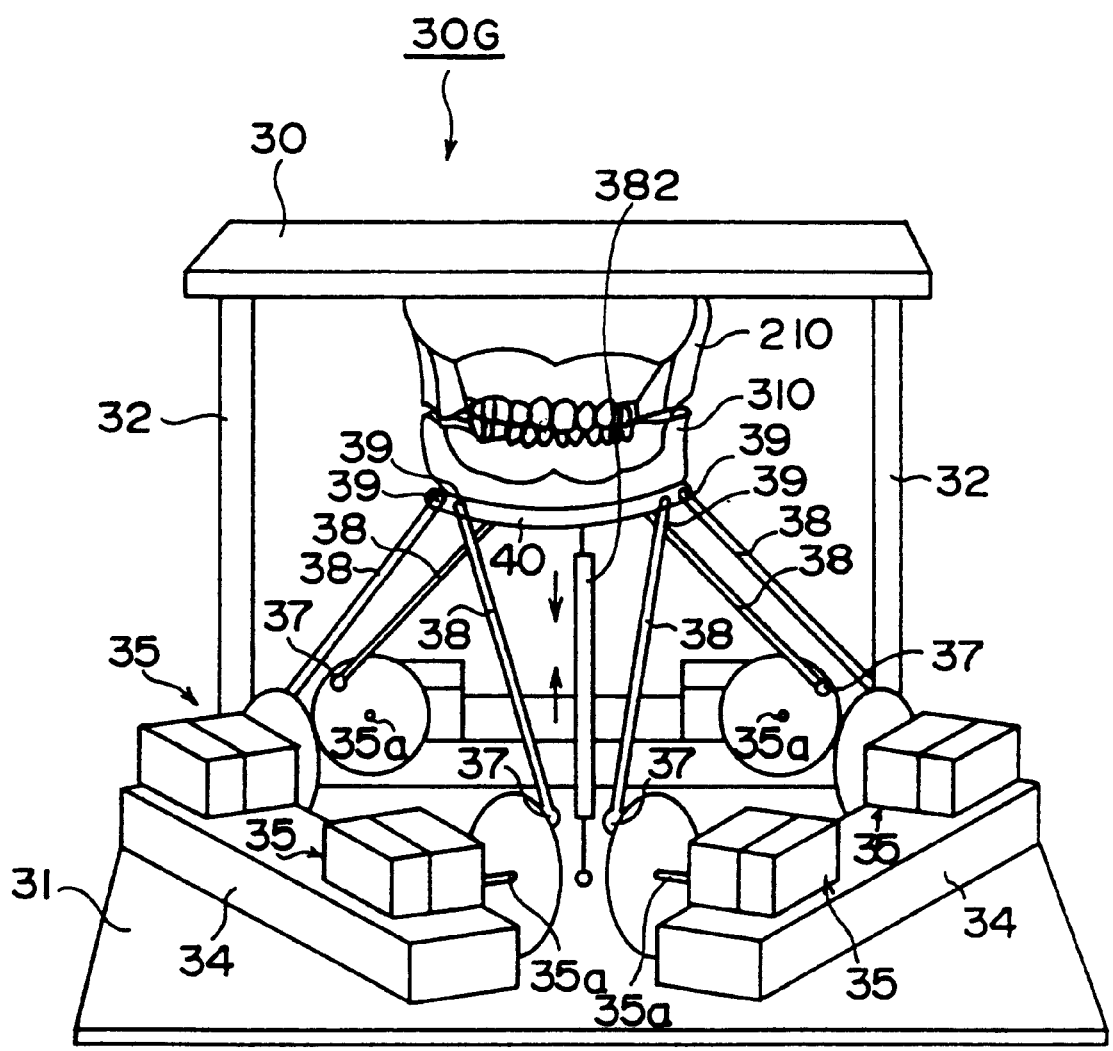
FIG. 41 is a typical illustration useful for understanding a ninth embodiment of a jaw movement reproducing apparatus constituting a jaw movement simulator according to the present invention.

FIG. 41 is a typical illustration useful for understanding a ninth embodiment of a jaw movement reproducing apparatus constituting a jaw movement simulator according to the present invention. There will be described a difference between it and the eighth embodiment shown in FIG. 39.

According to the jaw movement reproducing apparatus 30F shown in FIG. 39, there is provided the tension spring 382 for each of the 6 links 38. On the contrary, according to the jaw movement reproducing apparatus 30G shown in FIG. 41, there is provided only one tension spring 382 between the center of a substrate 31 and the center of the operating plate 40. In this case, it is possible to remove on a batch basis not only backlash of the ball joints, but also backlash of the various parts such as backlash of the rotating shafts 35a of the servo motors 35, etc. However, in this case, the pull strength of the tension spring 382 acts on the servo motor 35 as direct load, and thus there is a need to use a servo motor having a large torque.

Figure 42:
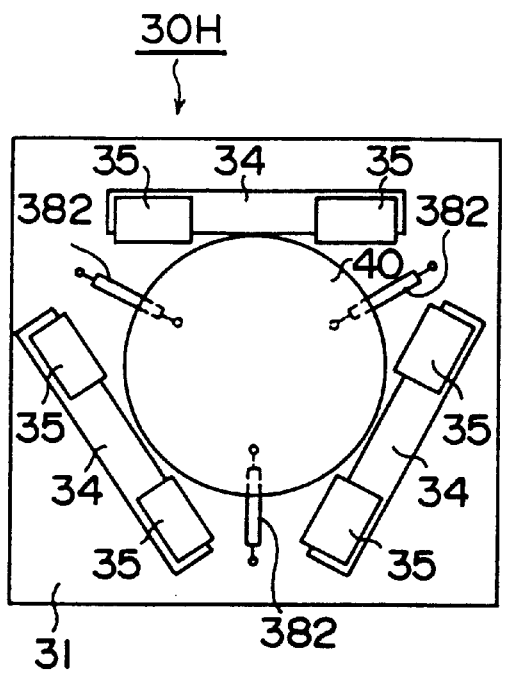
FIG. 42 is a typical illustration useful for understanding a tenth embodiment of a jaw movement reproducing apparatus.

FIG. 42 is a typical illustration useful for understanding a tenth embodiment of a jaw movement reproducing apparatus, and is a schematic plan view showing the state in which the ceiling board 33, the upper jaw model 210 and the lower jaw model 310 in the jaw movement reproducing apparatus shown in FIG. 41 are removed, and looking from the top. There will be described a difference between it and the ninth embodiment shown in FIG. 41.

In a jaw movement reproducing apparatus 30H shown in FIG. 42, there are provided 3 tension springs 382 between the substrate 31 and the operating plate 40. In order to remove on a batch basis not only backlash of the ball joints, but also backlash of the various parts interposed between the substrate 31 and the operating plate 40, it is acceptable that only one tension spring is provided as shown in FIG. 41, or alternatively it is also acceptable that a plurality of tension springs 382 are provided as shown in FIG. 42 so that they share the pull strength between the substrate 31 and the operating plate 40.

Figure 43:
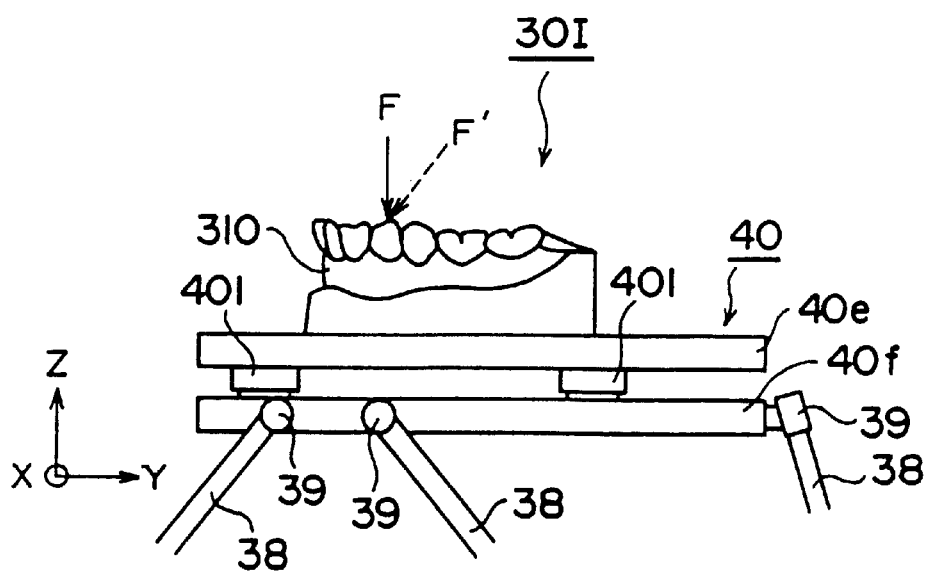
FIG. 43 is a typical illustration useful for understanding an eleventh embodiment of a jaw movement reproducing apparatus, but a part thereof.
Figure 44:
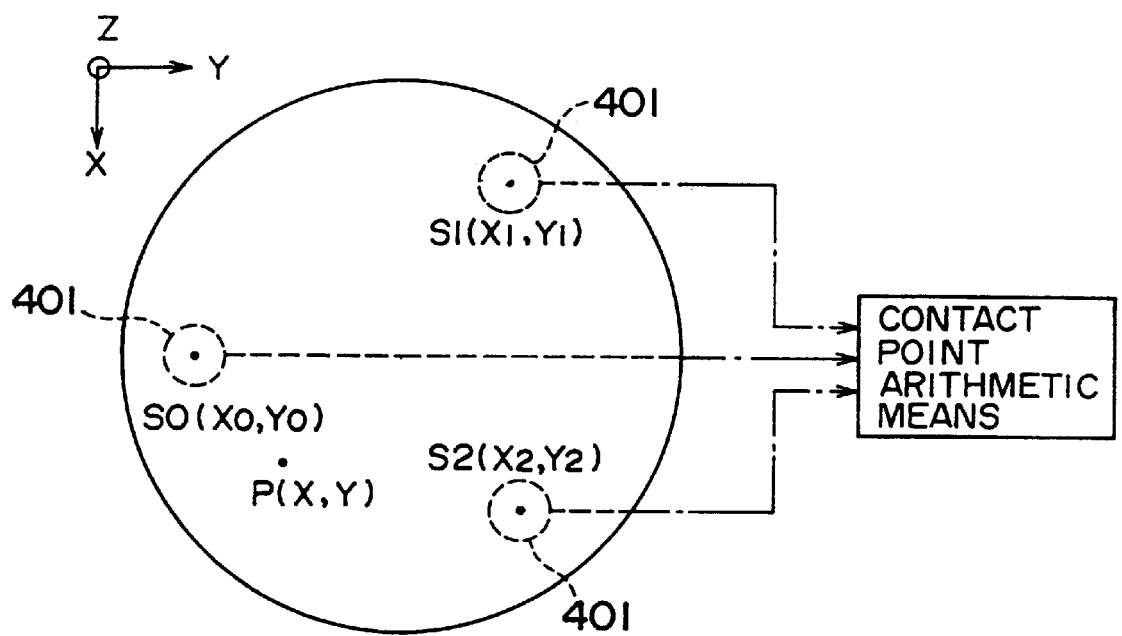
FIG. 44 is a plan view of the operating plate in the eleventh embodiment shown in FIG. 43 looking from the top.

FIG. 43 is a typical illustration useful for understanding an eleventh embodiment of a jaw movement reproducing apparatus, but a part thereof. FIG. 44 is a plan view of the operating plate 40 in the eleventh embodiment shown in FIG. 43, looking from the top According to a jaw movement reproducing apparatus 30I shown in FIG. 43, an operating plate 40 comprises two parallel flat plates 40e and 40f, and there are provided 3 load sensors 401, at positions $(X_0, Y_0)$, $(X_1, Y_1)$ and $(X_2, Y_2)$, respectively, as shown in FIG. 44, between the two flat plates 40e and 40f.

In the lower jaw movement of the human body, it is very important to know a position (an occlusion initial contact position) at which the lower jaw is first in contact with the upper jaw at the time of occlusion). In many cases, however, it is difficult to know the occlusion initial contact position directly from the human body. For this reason, according to the present embodiment, the jaw movement reproducing apparatus 30I having load sensors 401a, 401b and 401c is used to determine the occlusion initial contact position in the manner as will be described below.

It is assumed that the jaw movement reproducing L apparatus 30I is used, and when the lower jaw model 310 is moved to make a performance of shutting mouth, the lower jaw model 310 is in contact with the upper jaw model (not illustrated in FIG. 43), so that a force F, which is shown in FIG. 43 with the arrow of the solid line, is applied to a certain point on the lower jaw model 310. Let us suppose that an approximation such that the operating plate 40 is arranged horizontally at the time when the occlusion initial contact occurs is permitted, and the force F is applied to the lower jaw model 310 vertically. At that time, with respect to the load sensors 401, it is permitted to use load sensors capable of measuring a load of one axis only in the vertical direction.

Providing that loads S 0, S 1, S 2 are applied to the three load sensors 401, respectively, through the occlusion initial contact, from the balance of the force, $$S_0+S_1+S_2=P \quad (79)$$

from the balance of the moment with respect to X axis, $$S_0X_0+S_1X_1+S_2X_2-PX=0 \quad (80)$$

from the balance of the moment with respect to Y axis, $$S_0Y_0+S_1Y_1+S_2Y_2-PY=0 \quad (81)$$

from the equations (79), (80), (81)

$$X=(S_0X_0+S_1X_1+S_2X_2)/(S_0+S_1+S_2)$$

$$Y=(S_0Y_0+S_1Y_1+S_2Y_2)/(S_0+S_1+S_2)$$

In this manner, it is possible to determine the load point positions (X, Y) on the operating plate 40.

Next, there will be explained a case where it is expected that a slant force F' as shown in FIG. 43 with a broken line is applied. At that time, with respect to 3 load sensors 401 shown in FIG. 44, there are adopted three axis load sensors capable of measuring loads in X, Y, Z three axis directions.

[Compute load points when 3 three axis load sensors are used]

Let us consider X Y Z coordinates. 3 pieces of three axis load sensors are mounted in such a manner that their measurement axes are parallel to X Y Z axes, respectively. The positions of the load sensors are expressed as follows in X Y Z coordinates.

$S_0(x_0, y_0, z_0)$ $S_1(x_1, y_1, z_1)$ $S_2(x_2, y_2, z_2)$

Loads of the respective axes of the load sensors are as follows.

$S_0(S_{0x}, S_{0y}, S_{0z})$ $S_1(S_{1x}, S_{1y}, S_{1z})$ $S_2(S_{2x}, S_{2y}, S_{2z})$

It is assumed that load of F' is applied to a point P of the coordinate values (x, y, z), and components of the respective axes of the load F' are expressed by $(F_x, F_y, F_z)$.

From the balance of the force $$F_x=S_{0x}+S_{1x}+S_{2x} \quad (82)$$

$$F_y=S_{0y}+S_{1y}+S_{2y} \quad (83)$$

$$F_z=S_{0z}+S_{1z}+S_{2z} \quad (84)$$

from the balance of the moment with respect to X axis, $$F_zy+S_{0z}y_0+S_{1z}y_1+S_{2z}y_2+F_yz+S_{0y}z_0+S_{1y}z_1+S_{2y}z_2=0 \quad (85)$$

from the balance of the moment with respect to Y axis, $$F_zx+S_{0z}x_0+S_{1z}x_1+S_{2z}x_2+F_xz+S_{0x}z_0+S_{1x}z_1+S_{2x}z_2=0 \quad (86)$$

from the balance of the moment with respect to Z axis, $$\sqrt{(F_x^2+F_y^2)}\sqrt{(x^2+y^2)} + \sqrt{(S_{0x}^2+S_{0y}^2)}\sqrt{(x_0^2+y_0^2)} + \\ \sqrt{(S_{1x}^2+S_{1y}^2)}\sqrt{(x_1^2+y_1^2)} + \sqrt{(S_{2x}^2+S_{2y}^2)}\sqrt{(x_2^2+y_2^2)} = 0 \quad (87)$$

Here, in case of $$A = S_{0z}y_0 + S_{1z}y_1 + S_{2z}y_2 + S_{0y}z_0 + S_{1y}z_1 + S_{2y}z_2$$

$$B = S_{0z}x_0 + S_{1z}x_1 + S_{2z}x_2 + S_{0x}z_0 + S_{1x}z_1 + S_{2x}z_2$$

-continued $$C = \sqrt{(F_x^2 + F_y^2)}$$

$$E = \sqrt{(S_{0x}^2 + S_{0y}^2)} \cdot \sqrt{(x_0^2 + y_0^2)} +$$
$$\sqrt{(S_{1x}^2 + S_{1y}^2)} \cdot \sqrt{(x_1^2 + y_1^2)} +$$
$$\sqrt{(S_{2x}^2 + S_{2y}^2)} \cdot \sqrt{(x_2^2 + y_2^2)}$$

then the equations (85), (86) and (87) are expressed as follows.

$$F_z y + F_y z + A = 0 \qquad (88)$$

$$F_z x + F_x z + B = 0 \qquad (89)$$

$$C\sqrt{(x^2+y^2)} + E = 0 \qquad (90)$$

From the above, it is possible to know the position of the load point, that is, the occlusion initial contact position including the height direction (Z axis direction) of FIG. 43, by determining x, y, z from the above-noted three equations.

Figure 45:
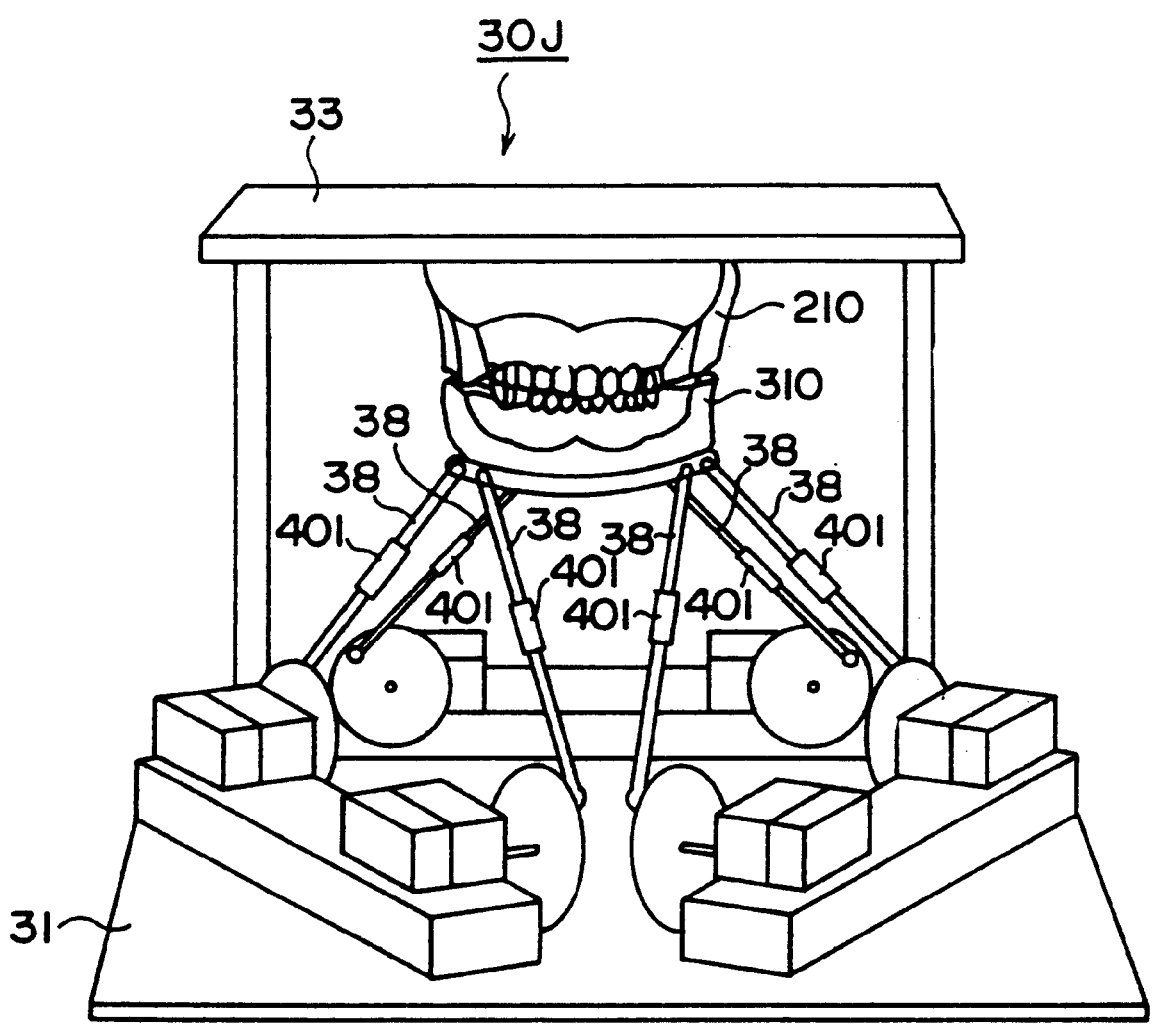
FIG. 45 is a typical illustration useful for understanding a twelfth embodiment of a jaw movement reproducing apparatus.

FIG. 45 is a typical illustration useful for understanding a twelfth embodiment of a jaw movement reproducing apparatus.

In a jaw movement reproducing apparatus 30J shown in FIG. 45, there is provided a load sensor 401 on a middle portion of each of the links 38.

According to the jaw movement reproducing apparatus 30I shown in FIGS. 43 and 44, the load sensors 401 are provided on the operating plate 40. With respect to set up positions of the load sensors 401, however, it is acceptable that the load sensors 401 are mounted on the links 38, for example, as shown in FIG. 36, or alternatively, it is also c acceptable that the load sensors 401 are mounted at the upper jaw model 210 side or the ceiling board 33 side.

As explained above, according to the present invention, it is possible to exactly simulate a jaw movement.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

What is claimed is:

1. A jaw movement simulator in which an upper jaw model, patterned after at least part of an upper jaw and a lower jaw model patterned after at least part of a lower jaw are mounted, and the lower jaw model is relatively moved with the respect to the upper jaw model, the jaw movement simulator comprising:

a substrate;

a lower jaw fixing unit on which the lower jaw model is fixed;

at least one lower jaw fixing unit supporting part for supporting said lower jaw fixing unit in such a manner that a position and a posture of said lower jaw fixing unit in a three-dimensional space are changeable with respect to said substrate;

lower jaw driving means for moving said lower jaw fixing unit supporting parts to alter the position and the posture of said lower jaw fixing unit;

an upper jaw fixing unit on which the upper jaw model is fixed in a predetermined positional relation with respect to the lower jaw model fixed on said lower jaw fixing unit in a predetermined initial position and a predetermined initial posture; and lower jaw control means for controlling said lower jaw driving means in accordance with data representative of relative position and posture of the lower jaw with respect to the upper jaw so that the lower jaw model fixed on said lower jaw fixing unit offers its position and posture according to said data;

a lower jaw model fixing position arithmetic means for determining a fixing position of the lower jaw model for said lower jaw fixing unit, wherein said lower jaw control means controls said lower jaw driving means in accordance with said data and in addition data representative of a fixing position of the lower jaw model, determined by said lower jaw fixing position arithmetic means;

a contact detection probe for detecting that the lower jaw model fixed on said lower jaw fixing unit is in contact with said contact detection probe; and a sensor for detecting a position and a posture of said lower jaw fixing unit at time when the lower jaw model is in contact with said contact detection probe, wherein said lower jaw model fixing position arithmetic means determines the fixing position of the lower jaw model for said lower jaw fixing unit in accordance with the position and the posture detected by said sensor.

2. A jaw movement simulator in which an upper jaw model, patterned after at least part of an upper jaw and a lower jaw model patterned after at least part of a lower jaw, are mounted, and the lower jaw model is relatively moved with the respect to the upper jaw model, the jaw movement simulator comprising:

a substrate;

a lower jaw fixing unit on which the lower jaw model is fixed;

at least one lower jaw fixing unit supporting part for supporting said lower jaw fixing unit in such a manner that a position and a posture of said lower jaw fixing unit in a three-dimensional space are changeable with respect to said substrate;

lower jaw driving means for moving said lower jaw fixing unit supporting parts to alter the position and the posture of said lower jaw fixing unit;

an upper jaw fixing unit on which the upper jaw model is fixed in a predetermined positional relation with respect to the lower jaw model fixed on said lower jaw fixing unit in a predetermined initial position and a predetermined initial posture; and lower jaw control means for controlling said lower jaw driving means in accordance with data representative of relative position and posture of the lower jaw with respect to the upper jaw so that the lower jaw model fixed on said lower jaw fixing unit offers its position and posture according to said data;

a lower jaw model fixing position arithmetic means for determining a fixing position of the lower jaw model for said lower jaw fixing unit, wherein said lower jaw control means controls said lower jaw driving means in accordance with said data and in addition data representative of a fixing position of the lower jaw model, determined by said lower jaw fixing position arithmetic means;

a contact detection probe for detecting that the lower jaw model fixed on said lower jaw fixing unit, wherein said lower jaw control means controls said lower jaw driving means under operation of said handler, and said lower jaw model fixing position arithmetic means determines the fixing position of the lower jaw model for said lower jaw fixing unit in accordance with the position and the posture of said lower jaw fixing unit at time when the lower jaw model is in contact with said contact detection probe.

3. A jaw movement simulator in which an upper jaw model, patterned after at least part of an upper jaw and a lower jaw model patterned after at least part of a lower jaw, are mounted, and the lower jaw model is relatively moved with the respect to the upper jaw model, the jaw movement simulator comprising:

a substrate;

a lower jaw fixing unit on which the lower jaw model is fixed;

at least one lower jaw fixing unit supporting part for supporting said lower jaw fixing unit in such a manner that a position and a posture of said lower jaw fixing unit in a three-dimensional space are changeable with respect to said substrate;

lower jaw driving means for moving the at least one lower jaw fixing unit supporting part to alter the position and the posture of the at least one lower jaw fixing unit;

an upper jaw fixing unit on which the upper jaw model is fixed in a predetermined positional relation with respect to the lower jaw model fixed on said lower jaw fixing unit in a predetermined initial position and a predetermined initial posture; and lower jaw control means for controlling said lower jaw driving means in accordance with data representative of relative position and posture of the lower jaw with respect to the upper jaw so that the lower jaw model fixed on said lower jaw fixing unit offers its position and posture according to said data;

wherein said lower jaw fixing unit has a first member supported by the at least one lower jaw fixing unit supporting p, a second member on which the lower jaw model is fixed, and a rotating joint for rotatably moving said second member in up and down directions with respect to said first member.

4. A jaw movement simulator in which an upper jaw model patterned after at least part of an upper jaw and a lower jaw model patterned after at least part of a lower jaw, are mounted, and the lower jaw model is relatively moved with the respect to the upper jaw model, the jaw movement simulator comprising:

a substrate;

a lower jaw fixing unit on which the lower jaw model is fixed;

at least one lower jaw fixing unit supporting part for supporting said lower jaw fixing unit in such a manner that a position and a posture of said lower jaw fixing unit in a three-dimensional space are changeable with respect to said substrate;

lower jaw driving means for moving said lower jaw fixing unit supporting parts to alter the position and the posture of said lower jaw fixing unit;

an upper jaw fixing unit on which the upper jaw model is fixed in a predetermined positional relation with respect to the lower jaw model fixed on said lower jaw fixing unit in a predetermined initial position and a predetermined initial posture;

lower jaw control means for controlling said lower jaw driving means in accordance with data representative of relative position and posture of the lower jaw with respect to the upper jaw so that the lower jaw model fixed on said lower jaw fixing unit offers its position and posture according to said data; and a tension spring adapted for eliminating or reducing backlash of said lower jaw fixing unit.

5. A jaw movement simulator in which an upper jaw model, patterned after at least part of an upper jaw and a lower jaw model patterned after at least part of a lower jaw, are mounted, and the lower jaw model is relatively moved with the respect to the upper jaw model, the jaw movement simulator comprising:

a substrate;

a lower jaw fixing unit on which the lower jaw model is fixed;

at least one lower jaw fixing unit supporting part for supporting said lower jaw fixing unit in such a manner that a position and a posture of said lower jaw fixing unit in a three-dimensional space are changeable with respect to said substrate;

lower jaw driving means for moving said lower jaw fixing unit supporting parts to alter the position and the posture of said lower jaw fixing unit;

an upper jaw fixing unit on which the upper jaw model is fixed in a predetermined positional relation with respect to the lower jaw model fixed on said lower jaw fixing unit in a predetermined initial position and a predetermined initial posture;

lower jaw control means for controlling said lower jaw driving means in accordance with data representative of relative position and posture of the lower jaw with respect to the upper jaw so that the lower jaw model fixed on said lower jaw fixing unit offers its position and posture according to said data;

a plurality of load sensors for measuring at least three point loads by force due to a first contact of the upper jaw model with the lower jaw model when the upper jaw model fixed on said upper jaw fixing unit and the lower jaw model fixed on said lower jaw fixing unit occlude; and contact point arithmetic means for determining a first contact point at time of occlusion of the upper jaw model and the lower jaw model in accordance with loads measured by said plurality of load sensors.

6. A jaw movement simulation system for reproducing a movement of a jaw of a subject comprising:

a jaw movement image pick-up apparatus for imaging a movement of a jaw of a subject, said jaw movement image pick-up apparatus comprising a plurality of cameras for imaging the subject from different directions;

a head frame to be mounted on a head of the subject or on a portion moving in one united body together with the head, said head frame having at least three different targets, which are not located on a same straight line, the targets visually recognized by the plurality of cameras, said targets being indexes for a coordinate measurement on images through imaging; and a lower jaw frame to be fixed on a lower jaw of the subject, said lower jaw frame having at least three different targets, which are not located on a same straight line, the targets visually recognized by the plurality of cameras, the targets being indexes for a coordinate measurement on images through imaging;

a jaw movement arithmetic unit for detecting the targets on the images obtained when the subject, on whose head said head frame is fixed and on whose lower jaw said lower jaw frame is fixed, is photographed by said plurality of cameras, to determine a first data representative of position and posture of the lower jaw of the subject when the head of the subject is referred, in accordance with positions of the targets on the images;

a jaw movement reproducing unit in which an upper jaw model patterned after at least part of an upper jaw and a lower jaw model patterned after at least part of a lower jaw are mounted, and the lower jaw model is relatively moved with the respect to the upper jaw model, said jaw movement simulator comprising:

a substrate;

a lower jaw fixing unit on which the lower jaw model is fixed;

at least one lower jaw fixing unit supporting part for supporting said lower jaw fixing unit in such a manner that a position and a posture of said lower jaw fixing unit in a three-dimensional space are changeable with respect to said substrate;

lower jaw driving means for moving said lower jaw fixing unit supporting parts to alter the position and the posture of said lower jaw fixing unit; and an upper jaw fixing unit on which the upper jaw model is fixed in a predetermined positional relation with respect to the lower jaw model fixed on said lower jaw fixing unit in a predetermined initial position and a predetermined initial posture; and a jaw movement reproducing control unit for controlling said lower jaw driving means of said jaw movement reproducing unit in accordance with the first data determined by said jaw movement arithmetic unit so that the lower jaw model fixed on said lower jaw fixing unit of said jaw movement reproducing unit reproduces a movement of the lower jaw of the subject, wherein the lower jaw model patterned after at least part of the lower jaw of the subject is mounted on said jaw movement reproducing unit, a reference jig, which has positioning means with respect to said lower jaw fixing unit and at least three different targets, which are not located on a same straight line, said targets being indexes for a coordinate measurement, is fixed on the lower jaw model, the reference jig fixed on the lower jaw model is fixed at a position determined by said positioning means, of said lower jaw fixing unit to fix the lower jaw model on said lower jaw fixing unit, and said lower jaw frame is fixed on the lower jaw model in such a manner that position and posture as to the lower jaw model are substantially the same as those as to the lower jaw of the subject in a case where said lower jaw frame is fixed on the lower jaw of the subject, the lower jaw model is photographed by a plurality of cameras from different directions so that said jaw movement simulation system determines a second data representative of relative position and posture between the lower jaw model and the reference jig fixed on the lower jaw mode, as well as the first data, and said jaw movement reproducing control unit controls said lower jaw driving means of said jaw movement reproducing unit in accordance with the first data and the second data, so that the lower jaw model fixed on said lower jaw fixing unit of said jaw movement reproducing unit reproduces a movement of the lower jaw of the subject.

7. A jaw movement simulation system according to claim 6, wherein the targets of said head frame and the targets of said lower jaw frame are light-emitting elements, and wherein the lower jaw model, with which said reference jig is integrated, is fixed on said lower jaw fixing unit and said lower jaw frame is fixed on the lower jaw model, and the lower jaw model is photographed by a plurality of cameras, a pointer having a plurality of light-emitting elements, in which a positional relationship between the plurality of light-emitting elements and a tip to be in contact with a desired coordinate measurement point is known, is prepared, and said jaw movement simulation system recognizes positions of the light-emitting elements of said lower jaw frame, recognizes positions of the targets of said reference jig by recognition of positions of the light-emitting elements of said pointer by bringing the tip of said pointer into contact with the targets of said reference jig to provide position information of the light-emitting elements of said pointer in form of a parameter, and determines the second data in accordance with positional information as to those recognized positions of the light-emitting elements of said lower jaw frame and positions of the targets of said reference jig.

8. A jaw movement simulation system according to claim 6, wherein the targets of said head frame, the targets of said lower jaw frame, and the targets of said reference jig are light-emitting elements, and wherein the lower jaw model, with which said reference jig is integrated, is fixed on said lower jaw fixing unit and said lower jaw frame is fixed on the lower jaw model, and then the lower jaw model is photographed by a plurality of cameras, whereby said jaw movement simulation system recognizes positions of the light-emitting elements of said lower jaw frame and positions of the light-emitting elements of said reference jig, and determines the second data in accordance with positional information as to those recognized positions of the light-emitting elements of said lower jaw frame and positions of the light-emitting elements of said reference jig.

9. A jaw movement simulation method of reproducing a movement of a jaw of a subject using a jaw movement simulation system comprising:

a jaw movement image pick-up apparatus for imaging a movement of a jaw of a subject, said jaw movement image pick-up apparatus comprising a plurality of cameras for imaging the subject from different directions, a head frame to be mounted on a head of the subject or on a portion moving in one united body together with the head, said head frame having at least three different, which are not located on a same straight line, targets visually recognized by the plurality of cameras, said targets being indexes for a coordinate measurement on images through imaging, a lower jaw frame to be fixed on a lower jaw of the subject, said lower jaw frame having at least three different targets, which are not located on a same straight line, targets visually recognized by the plurality of cameras, said targets being indexes for a coordinate measurement on images through imaging, a lower jaw frame to be fixed on a lower jaw of the subject, said lower jaw frame having at least three different targets, which are not located on a same straight line, targets visually recognized by the plurality of cameras, said targets being indexes for a coordinate measurement on images through imaging, and a pointer having a plurality of targets, in which a positional relationship between the plurality of targets and a tip to be in contact with lower teeth is known;

a jaw movement arithmetic unit for detecting the targets on the images obtained when the subject, on whose head said head frame is fixed and on whose lower jaw said lower jaw frame is fixed, is photographed by said plurality of cameras, to determine a first data representative of position and posture of the lower jaw of the subject when the head of the subject is referred, in accordance with positions of the targets on the images, and in addition determine contact point position information representative of a contact point of said pointer with respect to the lower jaw in accordance with positions of the targets on the images when the tip of said pointer is in contact with lower teeth;

a jaw movement reproducing unit in which a n upper jaw model patterned after at least part of an upper jaw and a lower jaw model patterned after at least part of a lower jaw are mounted, and the lower jaw model is relatively moved with respect to the upper jaw model, said jaw movement simulator comprising: a substrate; a lower jaw fixing unit on which the lower jaw model is fixed; a lower jaw fixing unit supporting parts for supporting said lower jaw fixing unit in such a manner that a position and a posture of said lower jaw fixing unit in a three-dimensional space are changeable with respect to said substrate; lower jaw driving means for moving said lower jaw fixing unit supporting parts to alter the position and the posture of said lower jaw fixing unit; an upper jaw fixing unit on which the upper jaw model is fixed in a predetermined positional relation with respect to the lower jaw model fixed on said lower jaw fixing unit in a predetermined initial position and a predetermined initial posture; and a detachable contact detection probe for detecting a contact of the lower jaw model fixed on the lower jaw fixing unit, in which a positional relationship with said upper jaw fixing unit is defined; and a jaw movement reproducing control unit for controlling said lower jaw driving means of said jaw movement reproducing unit in accordance with the first data determined by said jaw movement arithmetic unit so that the lower jaw model fixed on said lower jaw fixing unit of said jaw movement reproducing unit reproduces a movement of the lower jaw of the subject;

wherein the lower jaw model patterned after at least part of the lower jaw of the subject is mounted on said jaw movement reproducing unit, said lower jaw fixing unit is moved in such a manner that points on denture of the lower jaw model, which points correspond to contact points of lower teeth of the subject with which said pointer jig is in contact when a lower jaw movement of the subject is photographed, is in contact with said contact detection probe attached in a state that a positional relationship with said upper jaw fixing unit is defined, so that an operation for causing said jaw movement simulation system to recognize a position and a posture of said lower jaw fixing unit in a contacting state of said contact detection probe is repeated as to at least three denture of the lower jaw model; and said jaw movement simulation system determines a second data representative of a position and a posture of the lower jaw model fixed on said lower jaw fixing unit with respect to said lower jaw fixing unit in accordance with information representative of the position and the posture of the lower jaw model obtained through said operations and said contact point information; and said jaw movement reproducing control unit controls said lower jaw driving means of said jaw movement reproducing unit in accordance with the first data and the second data, so the lower jaw model fixed on said lower jaw fixing unit of said jaw movement reproducing unit reproduces a movement of the lower jaw of the subject.

10. A jaw movement simulation method of reproducing a movement of a jaw of a subject using a jaw movement simulation system comprising:

a jaw movement image pick-up apparatus for imaging a movement of a jaw of a subject, said jaw movement image pick-up apparatus comprising a plurality of cameras for imaging the subject from different directions, a head frame to be mounted on a head of the subject, said head frame having at least three different targets, which are not located on a same straight line, the targets visually recognized by the plurality of cameras, said targets being indexes for a coordinate measurement on images through imaging, a lower jaw frame to be fixed on a front portion of front teeth of a lower jaw of the subject, said lower jaw frame having at least three different targets, which are not located on a same straight line, the targets visually recognized by the plurality of cameras, said targets being indexes for a coordinate measurement on images through imaging;

a jaw movement arithmetic unit for detecting the targets on a first image obtained when the subject, on whose lower jaw said lower jaw frame is fixed, is photographed by said plurality of cameras, and also detecting the targets on a second image obtained when the subject, on whose lower jaw said lower jaw frame and said transfer frame are fixed, is photographed by said plurality of cameras, to determine a first data representative of position and posture of the lower jaw of the subject when the head the subject is referred, in accordance with positions of the targets on the first and second images;

a jaw movement reproducing unit in which an upper jaw model patterned after at least part of an upper jaw and a lower jaw model patterned after at least part of a lower jaw are mounted, and the lower jaw model is relatively moved with respect to the upper jaw model, said jaw movement simulator comprising:

a substrate;

a lower jaw fixing unit on which the lower jaw model is fixed; a lower jaw fixing unit supporting member for supporting said lower jaw fixing unit in such a manner that a position and a posture of said lower jaw fixing unit in a three-dimensional space are changeable with respect to said substrate;

lower jaw driving means for moving said lower jaw fixing unit supporting parts to alter the position and the posture of said lower jaw fixing unit; and an upper jaw fixing unit on which the upper jaw model is fixed in a predetermined positional relation with respect to the lower jaw model fixed on said lower jaw fixing unit in a predetermined initial posture; and a jaw movement reproducing control unit for controlling said lower jaw driving means of said jaw movement reproducing unit in accordance with the first data determined by said jaw movement arithmetic unit so that the lower jaw model fixed on said lower jaw fixing unit of said jaw movement reproducing unit reproduces a movement of the lower jaw of the subject, wherein the lower jaw model patterned after at least part of the lower jaw of the subject is mounted on said jaw movement reproducing unit, a reference jig, which has positioning means with respect to said lower jaw fixing unit and at least three different targets, which are not located on a same straight line, said targets being indexes for a coordinate measurement, is fixed on the lower jaw model, the reference jig fixed on the lower jaw model is fixed at a position determined by said positioning means, of said lower jaw fixing unit to fix the lower jaw model on said lower jaw fixing unit, and said transfer frame is fixed on the lower jaw model in such a manner that position and posture as to the lower jaw model are substantially the same as those as to the lower jaw of the subject in a case where said transfer frame is fixed on the lower jaw of the subject, the lower jaw model is photographed by a plurality of cameras from different directions so that said jaw movement simulation system determines a second data representative of relative position and posture between the lower jaw model and the reference jig fixed on the lower jaw model, as well as the first data, and said jaw movement reproducing control unit controls said lower jaw driving means of said jaw movement reproducing unit in accordance with the first data and the second data, so that the lower jaw model fixed on said lower jaw fixing unit of said jaw movement reproducing unit reproduces a movement of the lower jaw of the subject.

11. A jaw movement simulation method according to claim 10, wherein the targets of said head frame, the targets of said lower jaw frame, and the targets of said transfer frame are light-emitting elements, and wherein the lower jaw model, with which said reference jig is integrated, is fixed on said lower jaw fixing unit and said transfer frame is fixed on the lower jaw model, and then the lower jaw model is photographed by a plurality of cameras, a pointer having a plurality of light-emitting elements, in which a positional relationship between the plurality of light-emitting elements and a tip to be in contact with a desired coordinate measurement point is known, is prepared, and said jaw movement simulation system recognizes positions of the light-emitting elements of said transfer frame, recognizes positions of the targets of said reference jig by recognition of positions of the light-emitting elements of said pointer by bringing the tip of said pointer into contact with the targets of said reference jig to provide position information of the light-emitting elements of said pointer in form of a parameter, and determines the second data in accordance with positional information as to those recognized positions of the light-emitting elements of said transfer frame and positions of the targets of said reference jig.

12. A jaw movement simulation method according to claim 10, wherein the targets of said head frame, the targets of said lower jaw frame, the targets of said transfer frame, and the targets of said reference jig are light-emitting elements, and wherein the lower jaw model, with which said reference jig is integrated, is fixed on said lower jaw fixing unit and said transfer frame is fixed on the lower jaw model, and then the lower jaw model is photographed by a plurality of cameras, whereby said jaw movement simulation system recognizes positions of the light-emitting elements of said transfer frame and positions of the light-emitting elements of said reference jig, and determines the second data in accordance with positional information as to those recognized positions of the light-emitting elements of said transfer frame and positions of the light-emitting elements of said reference jig.

13. A jaw movement simulation method of reproducing a movement of a jaw of a subject using a jaw movement simulation system comprising:

a jaw movement image pick-up apparatus for imaging a movement of a jaw of a subject using a jaw movement simulation system comprising:

a jaw movement image pick-up apparatus for imaging a movement of a jaw of a subject, said jaw movement image pick-up apparatus comprising a plurality of cameras for imaging the subject from different directions, a head frame to be mounted on a head of the subject, and head frame having at least three different targets, which are not located on a same straight line, the targets visually recognized by the plurality of cameras, said targets being indexes for a coordinate measurement on images through imaging, a lower jaw frame to be fixed on a front portion of front teeth of a lower jaw of the subject, said lower jaw frame having at least three different targets, which are not located on a same straight line, the targets visually recognized by the plurality of cameras, said targets being indexes for a coordinate measurement on images through imaging, and a transfer frame to be fixed on a portion including an upper portion of teeth of the lower jaw of the subject, said transfer frame having at least three different targets, which are not located on a same straight line, the targets visually recognized by the plurality of cameras, said targets being indexes for a coordinate measurement on images through imaging;

a jaw movement arithmetic unit for detecting the targets on a first image obtained when the subject, on whose head said head frame is fixed and on whose lower jaw said lower jaw frame is fixed, is photographed by said plurality of cameras, and also detecting the targets on a second image obtained when the subject, on whose lower jaw said lower jaw frame and said transfer frame are fixed, is photographed by said plurality of cameras, to determine data representative of position and posture of the lower jaw of the subject when the head of the subject is set as a standard, in accordance with positions of the targets on the first and second images;

a jaw movement reproducing unit in which an upper jaw model patterned after at least part of an upper jaw and a lower jaw model patterned after at least part of a lower jaw are mounted, and the lower jaw model is relatively moved with respect to the upper jaw model, said jaw movement simulator comprising:

a substrate;

a lower jaw fixing unit supporting member for supporting said lower jaw fixing unit in such a manner that a position and a posture of said lower jaw fixing unit in a three-dimensional space are changeable with respect to said substrate;

lower jaw driving means for moving said lower jaw fixing unit supporting parts to alter the position and the posture of said lower jaw fixing unit; and an upper jaw fixing unit on which the upper jaw model is fixed in a predetermined positional relation with respect to the lower jaw model fixed on said lower jaw fixing unit in a predetermined initial position and a predetermined initial posture; and a jaw movement reproducing control unit for controlling said lower jaw driving means of said jaw movement reproducing unit in accordance with the data determined by said jaw movement arithmetic unit so that the lower jaw model fixed on said lower jaw fixing unit of said jaw movement reproducing unit reproduces a movement of the lower jaw of the subject, wherein the lower jaw model patterned after at least part of the lower jaw of the subject is mounted on said jaw movement reproducing unit, a transfer jig for fixing a relative positional relationship between said transfer frame and a lower jaw model fixing member on which said lower jaw model is fixed, said lower jaw fixing member on which said lower jaw model is fixed, said lower jaw model fixing member having positioning means with respect to said lower jaw fixing unit, is prepared, said transfer frame is fixed on the lower jaw frame in such a manner that position and attitude as to the lower jaw model are substantially the same as those as to the lower jaw of the subject in a case where said transfer frame is fixed on the lower jaw of the subject, and said transfer frame is fixed on the lower jaw of the subject, and said transfer frame is fixed on said transfer jig, and further a state that said lower jaw model fixing member is fixed on said transfer is produce, and then in this state said lower jaw model is fixed on said lower jaw model fixing member, and said lower jaw model fixing member, on which said lower jaw model is fixed, is fixed on a position of said lower jaw fixing unit, said position being determined by said positioning means, so that the lower jaw model is fixed on said lower jaw fixing unit.

\* \* \* \* \*